United States Patent
Huang et al.

(10) Patent No.: US 9,730,934 B2
(45) Date of Patent: Aug. 15, 2017

(54) QUINAZOLINE DERIVATIVES SUBSTITUTED BY ANILINE, PREPARATION METHOD AND USE THEREOF

(75) Inventors: Zhenhua Huang, Jinan (CN); Yanyan Dong, Jinan (CN)

(73) Assignee: XUANZHU PHARMA CO., LTD., Jinan, Shandong Province (CN)

( * ) Notice: Subject to any disclaimer, the term of this patent is extended or adjusted under 35 U.S.C. 154(b) by 0 days.

(21) Appl. No.: 13/818,367

(22) PCT Filed: Aug. 30, 2011

(86) PCT No.: PCT/CN2011/001466
§ 371 (c)(1),
(2), (4) Date: Apr. 1, 2013

(87) PCT Pub. No.: WO2012/027960
PCT Pub. Date: Mar. 8, 2012

(65) Prior Publication Data
US 2013/0184297 A1    Jul. 18, 2013

(30) Foreign Application Priority Data
Aug. 30, 2010   (CN) .......................... 2010 1 0266177

(51) Int. Cl.

| | | |
|---|---|---|
| *C07D 239/94* | (2006.01) |
| *C07D 239/95* | (2006.01) |
| *C07D 403/04* | (2006.01) |
| *C07D 215/42* | (2006.01) |
| *C07D 215/38* | (2006.01) |
| *C07D 401/12* | (2006.01) |
| *A61K 31/517* | (2006.01) |
| *A61K 31/47* | (2006.01) |
| *C07D 239/86* | (2006.01) |
| *C07D 403/12* | (2006.01) |
| *C07D 403/14* | (2006.01) |
| *C07D 405/12* | (2006.01) |
| *C07D 409/12* | (2006.01) |
| *C07D 413/14* | (2006.01) |
| *C07D 451/02* | (2006.01) |

(Continued)

(52) U.S. Cl.
CPC ............ *A61K 31/517* (2013.01); *A61K 45/06* (2013.01); *C07D 239/86* (2013.01); *C07D 239/94* (2013.01); *C07D 401/12* (2013.01); *C07D 403/12* (2013.01); *C07D 403/14* (2013.01); *C07D 405/12* (2013.01); *C07D 409/12* (2013.01); *C07D 413/14* (2013.01); *C07D 451/02* (2013.01); *C07D 451/06* (2013.01); *C07D 471/04* (2013.01); *C07D 471/08* (2013.01); *C07D 471/10* (2013.01); *C07D 487/04* (2013.01); *C07D 487/08* (2013.01); *C07D 487/10* (2013.01); *C07D 491/08* (2013.01); *C07D 491/107* (2013.01); *C07D 493/08* (2013.01)

(58) Field of Classification Search
USPC ........... 544/283, 284, 293; 514/266.1, 266.2, 514/266.3, 266.4, 313; 546/159
See application file for complete search history.

(56) References Cited

U.S. PATENT DOCUMENTS

| | | |
|---|---|---|
| 6,127,374 A | 10/2000 | Bridges |
| 6,562,818 B1 | 5/2003 | Bridges |

(Continued)

FOREIGN PATENT DOCUMENTS

| | | |
|---|---|---|
| CN | 101356171 A | 1/2009 |
| CN | 102382065 A | 3/2012 |

(Continued)

OTHER PUBLICATIONS

Smaill, J.B. et al., J. Med. Chem. vol. 43, pp. 1380-1397. Published 2000.*

(Continued)

*Primary Examiner* — Timothy Thomas
*Assistant Examiner* — George W Kosturko
(74) *Attorney, Agent, or Firm* — Clark & Elbing LLP

(57) ABSTRACT

The invention relates to quinazoline derivatives substituted by aniline which are represented by the below formula (I), pharmaceutical acceptable salts and stereoisomer thereof, wherein these groups of $R^1$, $R^2$, $R^3$, $R^4$, $R^5$, $R^6$, L and n have the meanings given in the specification. The invention also relates to preparation methods, pharmaceutical compositions, pharmaceutical preparation and the use for preparation of medicine of treating excessive hyperplasia and chronic obstructive pulmonary disease and uses for treating excessive hyperplasia and chronic obstructive pulmonary disease thereof.

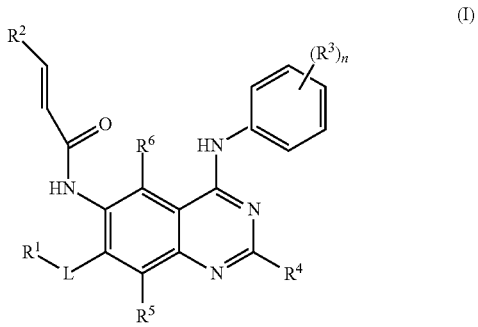

9 Claims, No Drawings

(51) Int. Cl.

| | |
|---|---|
| C07D 451/06 | (2006.01) |
| C07D 471/04 | (2006.01) |
| C07D 471/08 | (2006.01) |
| C07D 471/10 | (2006.01) |
| C07D 487/04 | (2006.01) |
| C07D 487/10 | (2006.01) |
| C07D 491/08 | (2006.01) |
| C07D 491/107 | (2006.01) |
| C07D 493/08 | (2006.01) |
| C07D 487/08 | (2006.01) |
| A61K 45/06 | (2006.01) |

(56) References Cited

U.S. PATENT DOCUMENTS

| | | | |
|---|---|---|---|
| 2002/0082270 A1* | 6/2002 | Himmelsbach | ...... C07D 403/12 514/266.2 |
| 2009/0306044 A1 | 12/2009 | Solca et al. | |
| 2011/0034689 A1 | 2/2011 | Lyssikatos et al. | |

FOREIGN PATENT DOCUMENTS

| | | |
|---|---|---|
| CN | 102452989 A | 5/2012 |
| DE | 10042061 A1 | 3/2002 |
| JP | 2004507533 A | 3/2004 |
| JP | 2006505509 A | 2/2006 |
| JP | 2006517959 A | 8/2006 |
| JP | 2009515851 A | 4/2009 |
| JP | 2009515988 A | 4/2009 |
| JP | 2009523737 A | 6/2009 |
| WO | WO-97/38983 A1 | 10/1997 |
| WO | WO 2004006846 A2 * | 1/2004 ........... C07D 239/94 |
| WO | WO-2012/158979 A1 | 11/2012 |
| WO | WO 2012/159457 A1 | 11/2012 |

OTHER PUBLICATIONS

Chen, "Computational Study of the Binding Mode of Epidermal Growth Factor Receptor Kinase Inhibitors," *Chem. Bio. Drug Des.* 71:434-446 (2008).

International Search Report for International Application No. PCT/CN2011/001466, mailed Dec. 8, 2011 (6 pages).

International Preliminary Report on Patentability for International Application No. PCT/CN2011/001466, issued Mar. 5, 2013 (7 pages).

Written Opinion of the International Searching Authority for International Application No. PCT/CN2011/001466, mailed Dec. 8, 2011 (6 pages).

Communication pursuant to Article 94(3) EPC for European Patent Application No. 11820990.7, dated Mar. 3, 2016 (4 pages).

Decision of Refusal for Japanese Patent Application No. 526299/2013, dated Oct. 28, 2015, mailed Nov. 4, 2015 (12 pages; English language translation provided).

Supplementary European Search Report for European Patent Application No. 11820990.7, dated Feb. 3, 2014 (5 pages).

Notice of Reasons for Refusal for Japanese Patent Application No. 526299/2013, dated Oct. 21, 2014 (English language translation included) (12 pages).

\* cited by examiner

QUINAZOLINE DERIVATIVES SUBSTITUTED BY ANILINE, PREPARATION METHOD AND USE THEREOF

CROSS-REFERENCE TO RELATED APPLICATIONS

This application is the U.S. National Stage filing under 35 U.S.C. §371 of International Application No. PCT/CN2011/001466, filed Aug. 30, 2011, which claims the benefit of Chinese Patent Application No. 201010266177.8, filed Aug. 30, 2010.

TECHNICAL FIELD

The present invention belongs to the field of pharmaceutical technology, more specifically relates to a quinazoline derivative substituted by aniline, a pharmaceutically acceptable salt thereof and a stereoisomer thereof, a preparation method thereof, a pharmaceutical composition containing said compound and a pharmaceutical formulation containing said compound, a use of said compound in treating a hyperplasia disease and a chronic obstructive pulmonary disease, and a use of said compound in the manufacture of a medicament for treating a hyperplasia disease and a chronic obstructive pulmonary disease.

BACKGROUND ART

The protein tyrosine kinase is an enzyme that catalytically transfers the phosphate group from ATP to the tyrosine residue located at the protein substrate, and has a play in the normal cell growth. Many growth factor receptor proteins operate via the tyrosine kinase, and influence the conduction of signal passage and further regulate the cell growth by this process. However, in some circumstances, these receptors become abnormally due to either the mutation or the overexpression, which cause the uncontrolled cell multiplication, cause the tumor growth, and finally initiate the well-known disease, i.e., cancer. The growth factor receptor protein tyrosine kinase inhibitor, via the inhibition of the above phosphorylation process, may treat cancers and other diseases characterized by the uncontrolled or abnormal cell growth.

An epidermal growth factor receptor (EGFR) is a multi-function glycoprotein that is widely distributed on the cell membranes of the tissues of the human body, and is an oncogene analog of avian erythroblastic leukemia viral (v-erb-b). Human EGFR/HER1/ErbB-1 and HER2 (human epidermal growth factor receptor-2)/ErbB-2/Teu/p185, HER3/ErbB-3, HER4/ErbB-4 and the like are grouped into the HER/ErbB family, and belong to protein tyrosine kinases (PTKs). It is indicated in the clinical study that EGFR and the like are expressed in the epithelia-derived tumors such as squamous cell carcinoma of head and neck, mammary cancer, rectal cancer, ovarian cancer, prostate carcinoma, non-small cell lung cancer, and the like. Pan-HER tyrosine kinase inhibitor, via the competitive binding the kinase catalytic sites in the intracellular region against ATP, blocks the autophosphorylation of intramolecular tyrosine, blocks the tyrosine kinase activation, inhibits HER family activation, and therefore inhibits cell cycle progression, accelerates cell apoptosis, and exerts the therapeutic action.

EGFR, after binding the ligand, forms a dimer with a subgroup of HER family, and then combines with ATP to activate the tyrosine kinase activity of the EGFR itself. Therefore, the autophosphorylation occurs in several tyrosine sites of the intracellular kinase region. Pan-HER tyrosine kinase inhibitor, via simultaneity acting on EGFR, and HER2/4, inhibits the activation of HER family, and play a good role in the tumor growth inhibition.

It is indicated in the study that Pan-HER tyrosine kinase irreversible inhibitor has an inhibition effect on HER2/4, besides it effectively inhibits EGFR. The pharmaceutical drugs of this kind, having an irreversible inhibition to both of HER/ErbB families, not only increase the drug activity, but also reduce the drug resistance, and have a substantial inhibition effect on H1975 cell lines which are resistant to erlotinib.

The pharmaceutical drugs that are now commercially available include selective EGFR tyrosine kinase inhibitor gefitinb (Iressa, ZD1839), erlotinib (Tarceva, OSI-774) and double EGFR/HER2 inhibitor Lapatinib (Tykerb, GW572016), and their structures are shown below. These three drugs are all reversible EGF receptor tyrosine phosphorylation kinase inhibitor. It is found in the study that they have good therapeutic response to some tumors initially. However, several months after the treatment, the disease progression appears again and therefore a natural or secondary drug resistance forms.

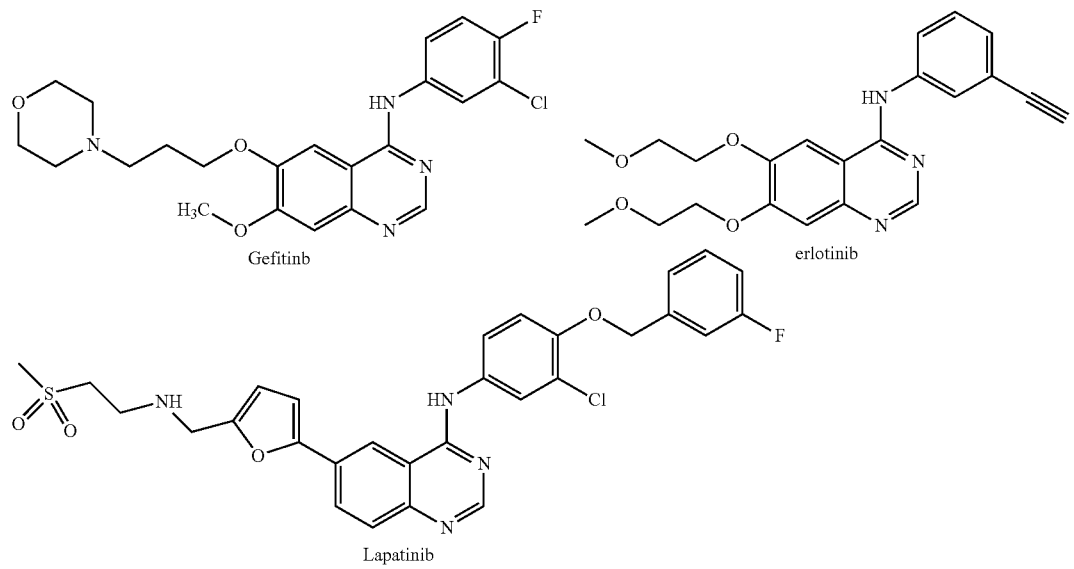

It is reported in the literature (Bioorganic & Medicinal Chemistry (2008) 16 page 3482-3488) that the commercially available drugs such as gefitinb and erlotinib have been widely used clinically. The long-term treatment of the late NSCLC (non-small cell lung cancer) may create an acquired drug-resistance, which has a negative effect on the therapeutical effect.

It is believed that the reversible EFG receptor tyrosine kinase inhibitor competes with ATP for the combination with EFG receptor tyrosine kinase. Due to the relative high concentration of the intracellular ATP (in order of mM), the reversible EGF receptor tyrosine kinase inhibitor, which shows a high activity in an in-vitro assay, is difficult to show the effect in the animal pathologic model. The irreversible EGF receptor tyrosine kinase inhibitor does not compete with ATP, and therefore it is expected that the non-reversible EGF receptor tyrosine kinase inhibitor may have a better in-vivo activity.

WO97/38983 discloses irreversible EGF receptor tyrosine kinase inhibitors. For these inhibitors, one Michael receptor is introduced at 6-position of quinazoline, and therefore a Michael addition reaction can be conducted between this receptor and —SH of the cysteine on the pouch wall of the EGF receptor tyrosine kinase activity center (Cys773). Moreover, the activities of these inhibitors and the complexity of the Michael addition reaction between these inhibitors and —SH of the cysteine are in a positive structure-function correlation.

DE10042061 A1 discloses a 4-phenylaminequinazoline derivative which has a lactone structure at 7-position of quinazoline. It is believed that it has an inhibition activity for the signal transduction mediated by the tyrosine kinase.

It is reported in the reference (Adv Ther (2011) 28(2) p. 1-8) that PF-299 (Pfizer) and Afatinib (BIBW2992) (Boehringer Ingelheim) are in the clinical stage III, and Neratinib (HKI292) is in the clinical stage II. It is believed that these compounds are irreversible tyrosine kinase inhibitor, and can solve the EGFR resistance.

It is reported in the reference (IDrugs (2004) 7(1) p. 58-63) that Canertinib (CI-1033) is in the clinical stage II, and has an activity for some types of tumore, and has no toxicity in the experimental model. Canertinib (CI-1033) has a structure of:

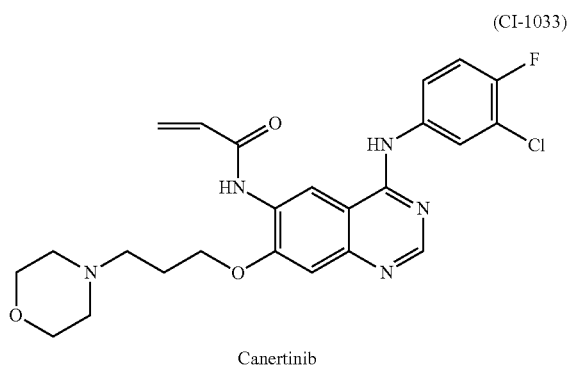

Canertinib

Upon developing the drug having a good antineoplastic effect, being able to reduce the drug resistance and having a good tolerance, the present inventors discover a quinazoline derivative having a Pan-HER irreversible inhibition function.

SUMMARY OF THE INVENTION

Therefore, the present invention provides a compound represented by a general formula (I), a pharmaceutically acceptable salt thereof and a stereoisomer thereof:

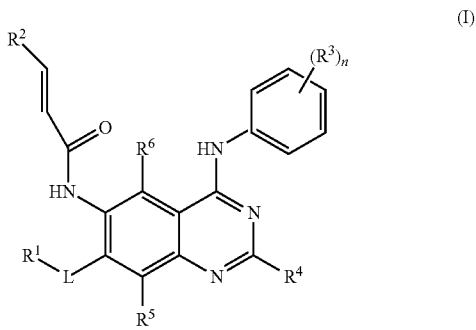

wherein, $R^1$ is selected from the group consisting of the following groups that are unsubstituted or substituted by 1-2 $Q_1$ substituents: a 6-10-membered fused ring-$C_{0-6}$alkyl group, a 7-10-membered spiro ring-$C_{0-6}$alkyl group or a 7-10-membered bridged ring-$C_{0-6}$alkyl group, wherein 1-3 carbon atoms of said fused ring, spiro ring or bridged ring can be replaced with 1-3 hetero atoms and/or groups that can be identical or different and are selected from the group consisting of O, S(O)$_m$, N(H)$_m$, NCH$_3$ and C(O), provided that after the replacement, O and C(O) in the ring are not adjacent to each other, $Q_1$ is selected from the group consisting of halogen, hydroxyl, amino, carboxyl, cyano, a $C_{1-6}$alkyl group, a $C_{1-6}$alkoxyl group, a $C_{1-6}$alkylamino group, a di($C_{1-6}$alkyl) amino group, a $C_{1-6}$alkylcarbonyloxy group, a $C_{1-6}$alkylacylamino group, a $C_{1-6}$alkylsulfonyl group, a $C_{1-6}$alkylsulfinyl group, a $C_{1-6}$alkylsulfonylamino group and a $C_{3-8}$cycloalkyl group;

$R^2$ is selected from the group consisting of hydrogen, a $C_{1-6}$alkyl group or a $C_{1-6}$alkoxyl group that is unsubstituted or substituted by 1-2 $Q_2$ substituents, a formyl group that is substituted by a $Q_2$ substituent or N(H)$_m$, $Q_2$ is selected from the group consisting of halogen, hydroxyl, amino, carboxyl, cyano, a $C_{1-6}$alkyl group, a $C_{1-6}$alkoxyl group, a $C_{1-6}$alkylamino group, a di($C_{1-6}$alkyl) amino group, a $C_{1-6}$alkylcarbonyloxy group, a $C_{1-6}$alkylacylamino group, a $C_{1-6}$alkylsulfonyl group, a $C_{1-6}$alkylsulfinyl group, a $C_{1-6}$alkylsulfonylamino group, a $C_{3-8}$cycloalkyl group, an unsaturated $C_{5-7}$ cyclic hydrocarbyl and a saturated or unsaturated 3-8-membered heterocyclyl, wherein the $C_{3-8}$cycloalkyl, the unsaturated $C_{5-7}$ cyclic hydrocarbyl and the saturated or unsaturated 3-8-membered heterocyclyl can further substituted by 1-2 $Q_3$ substituents, $Q_3$ is selected from the group consisting of halogen, hydroxyl, amino, carboxyl, cyano, a $C_{1-6}$alkyl group, a $C_{1-6}$alkoxyl group, a $C_{1-6}$alkylamino group, a di($C_{1-6}$alkyl) amino group, a $C_{1-6}$alkylcarbonyloxy group, a $C_{1-6}$alkylacylamino group, a $C_{1-6}$alkylsulfonyl group, a $C_{1-6}$alkylsulfinyl group, a $C_{1-6}$alkylsulfonylamino group and a halogen-substituted $C_{1-6}$alkoxy group;

$R^3$ is selected from the group consisting of hydrogen, halogen, hydroxyl, cyano, nitro, a $C_{1-6}$alkyl group, a $C_{1-6}$alkoxyl group, a $C_{1-6}$alkyl group or a $C_{1-6}$alkoxyl group that is substituted by halogen, a $C_{1-6}$alkylcarbonyloxy group, a $C_{1-6}$alkylacylamino group, a $C_{1-6}$alkylsulfonyl group, a $C_{1-6}$alkylsulfinyl group or a $C_{1-6}$alkylsulfonylamino group;

$R^4$, $R^5$ and $R^6$ are each independently selected from the group consisting of hydrogen, halogen, a $C_{1-6}$alkyl group, a $C_{1-6}$alkoxyl group, a $C_{1-6}$alkyl group or a $C_{1-6}$alkoxyl group that is substituted by halogen, a $C_{1-6}$alkylamino group or a di($C_{1-6}$alkyl)amino group;

L is selected from the group consisting of a covalent bond, O, $S(O)_m$, $N(H)_m$, $NCH_3$ or $C(O)$;

n is 1, 2 or 3; and m is 0, 1 or 2.

The present invention also provides a pharmaceutical composition containing a compound represented by the general formula (I), a pharmaceutically acceptable salt thereof or a stereoisomer thereof.

The present invention also provides a pharmaceutical formulation containing a compound represented by the general formula (I), a pharmaceutically acceptable salt thereof or a stereoisomer thereof and a pharmaceutically acceptable carrier.

The present invention also provides a compound represented by the general formula (I), a pharmaceutically acceptable salt thereof or a stereoisomer thereof, or a pharmaceutical composition containing a compound represented by the general formula (I), a pharmaceutically acceptable salt thereof or a stereoisomer thereof as a medicament for treating a hyperplasia disease and a chronic obstructive pulmonary disease.

The present invention also provides a use of a compound represented by the general formula (I), a pharmaceutically acceptable salt thereof or a stereoisomer thereof, or a pharmaceutical composition containing a compound represented by the general formula (I), a pharmaceutically acceptable salt thereof or a stereoisomer thereof for the manufacture of a medicament for treating a hyperplasia disease and a chronic obstructive pulmonary disease.

The present invention also provides a method for treating a hyperplasia disease and a chronic obstructive pulmonary disease, which comprises administering to a subject in need thereof an effective amount of a compound represented by the general formula (I), a pharmaceutically acceptable salt thereof or a stereoisomer thereof, or a pharmaceutical composition containing a compound represented by the general formula (I), a pharmaceutically acceptable salt thereof or a stereoisomer thereof.

The present invention also provides a process for preparing a compound of general formula (I), comprising the steps of:

Reaction Procedure:

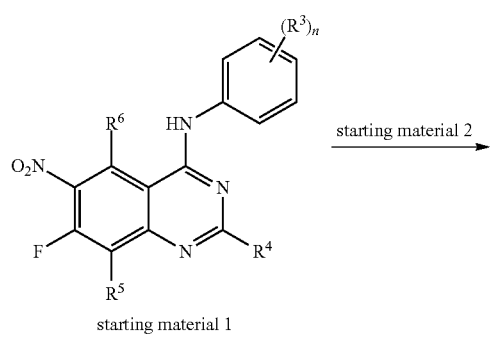

starting material 1

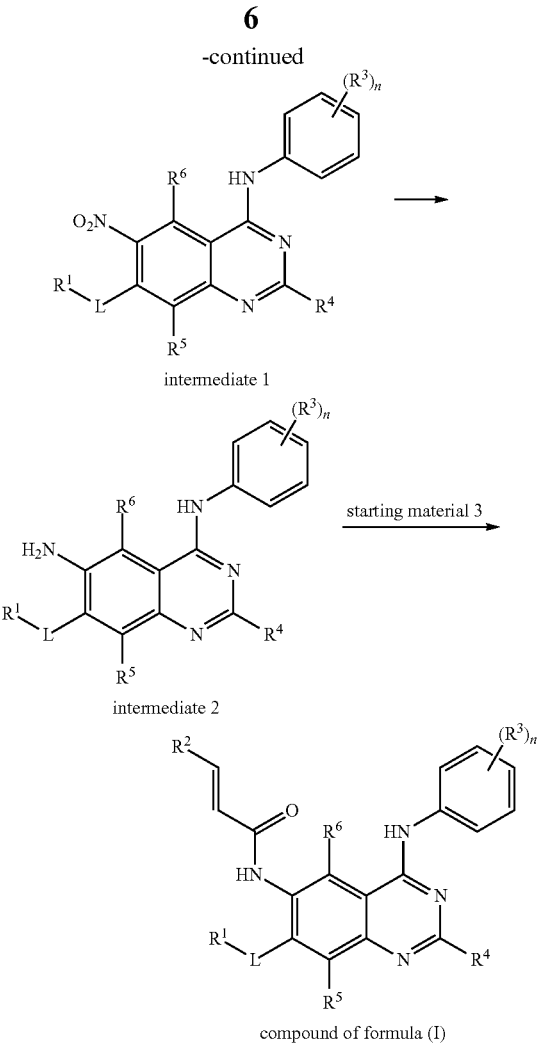

intermediate 1 intermediate 2 compound of formula (I)

wherein, $R^1$, $R^2$, $R^3$, $R^4$, $R^5$, $R^6$, L and n are as defined hereinbefore; the starting material 1 is synthesized according to the methodology provided in US 2005/0250761 A1, the starting material 2=$R^1$-LH; the starting material 3=$R^2$CH=CH—C(O)Cl or $R^2$CH=CH—COOH, (1) Dissolving the starting material 2 in a non-protonic polar organic solvent, and reacting with the starting material 1 in the presence of a base to produce the Intermediate 1;

(2) Reacting the Intermediate 1 with a reducing agent optionally in the presence of an acid to produce the Intermediate 2; and (3) Dissolving the Intermediate 2 in an organic solvent, and reacting with the starting material 3 in the presence of an organic base to produce the compound of formula (I).

As used herein, the term "halo" refers to fluoro, chloro, bromo or iodo.

As used herein, the term "$C_{1-6}$alkyl" refers to a straight or branched alkyl containing 1-6 carbon atoms; and its example includes but is not limited to methyl, ethyl, n-propyl, iso-propyl, n-butyl, iso-butyl, sec-butyl, tert-butyl, n-pentyl, iso-pentyl, 2-methylbutyl, neo-pentyl, 1-ethylpropyl, n-hexyl, iso-hexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, 1-methyl-2-methylpropyl and the like.

As used herein, the term "$C_{1-6}$alkoxy" refers to a "$C_{1-6}$alkyl-O—" group, wherein the $C_{1-6}$alkyl is defined as hereinbefore; and its example includes but is not limited to methoxy, ethoxy, propoxy, isopropoxy, butoxy, isobutoxy, tert-butoxy, sec-butoxy, pentoxy, neo-pentoxy, hexyloxy and the like.

As used herein, the term "$C_{3-8}$cycloalkyl" refers to a monocyclic saturated carbocyclic group containing 3-8, e.g. 3, 4, 5, 6, 7 or 8, preferably 3-6, e.g. 3-5 carbon atoms; and its example includes but is not limited to cyclopropyl, cyclobutyl, 1-methylcyclobutyl, cyclopentyl, cyclohexyl, cycloheptyl, cyclooctyl and the like.

As used herein, the term "$C_{1-6}$alkylamino" refers to a "$C_{1-6}$alkyl-NH—" group, wherein the $C_{1-6}$alkyl is defined as hereinbefore; and its example includes but is not limited to methylamino, ethylamino, propylamino, isopropylamino, butylamino, isobutylamino, tert-butylamino, sec-butylamino, pentylamino, neo-pentylamino, hexylamino and the like.

As used herein, the term "di($C_{1-6}$alkyl)amino" refers to a "$(C_{1-6}alkyl)_2$-N—" group, wherein the two $C_{1-6}$alkyl can be identical or different and are respectively defined as hereinbefore; and its example includes but is not limited to dimethylamino, diethylamino, dipropylamino, dibutylamino and the like.

As used herein, the term "$C_{1-6}$alkylcarbonyloxy", "$C_{1-6}$alkylacylamino", "$C_{1-6}$alkylsulfonyl", "$C_{1-6}$alkylsulfonylamino" and "$C_{1-6}$alkylsulfinyl" respectively refer to "$C_{1-6}$alkyl-C(O)O—", "$C_{1-6}$alkyl-C(O)NH—", "$C_{1-6}$alkyl-SO_2$—", "$C_{1-6}$alkyl-SO$_2$NH—" and "$C_{1-6}$alkyl-SO—" groups, wherein the $C_{1-6}$alkyl is defined as hereinbefore.

As used herein, the term "6-10-membered fused ring" refers to a saturated or unsaturated fused ring system containing 6-10 carbon atoms and formed by the linking of at least two cyclic structures sharing two adjacent atoms with each other, wherein the cyclocarbon atom(s) can be replaced with 1-3 hetero atoms and/or groups that can be identical or different and are selected from the group consisting of O, $S(O)_m$, $N(H)_m$, $NCH_3$ and $C(O)$, provided that after the replacement, O and C(O) in the ring are not adjacent to each other. Its example includes but is not limited to 5,6-dihydroimidazo[1.2-a]pyrazin-7(8H)-yl, 5,6-dihydro-1,7-naphthyridin-7(8H)-yl, 5H-pyrrolo[3.4-b]pyridin-6(7H)-yl, 7,8-dihydropyridino[4.3-d]pyrimidin-6(5H)-yl, 2,3,6,7-tetrahydro-1H-pyrazolo[4.3-c]pyridin-5(4H)-yl, 6,7-dihydrothiazolo[5.4-c]pyridin-5 (4H)-yl, 3-methyl-6,7-dihydro-3H-pyrazolo[4.5-c]pyridin-5(4H)-yl, 2-methylhexahydrocyclopenta[c]pyrrol-5-yl and the like.

As used herein, the term "7-10-membered spiro ring" refers to a saturated or unsaturated fused ring system containing 7-10 carbon atoms and formed by at least two rings sharing the same atom, wherein the cyclocarbon atom(s) can be replaced with 1-3 hetero atoms and/or groups that can be identical or different and are selected from the group consisting of O, $S(O)_m$, $N(H)_m$, $NCH_3$ and $C(O)$, provided that after the replacement, O and C(O) in the ring are not adjacent to each other. Its example includes but is not limited to 6-azaspiro[2.5]octan-6-yl, 7-azaspiro[3.5]nonan-7-yl, 8-azaspiro[4.5]decan-8-yl, 1-methyl-1,7-diazaspiro[4.4]nonan-7-yl, 2-methyl-2,6-diazaspiro[3.4]octan-6-yl, 6-azaspiro[3.4]octan-6-yl, 2-oxa-7-azaspiro[4.5]decan-7-yl, 2-oxa-8-azaspiro[4.5]decan-8-yl, 2-methyl-2,7-diazaspiro[4.5]decane and the like.

As used herein, the term "7-10-membered bridged ring" refers to a saturated or unsaturated fused ring system containing 7-10 carbon atoms and formed by any two rings sharing two atoms not directly linked, wherein the cyclocarbon atom(s) can be replaced with 1-3 hetero atoms and/or groups that can be identical or different and are selected from the group consisting of O, $S(O)_m$, $N(H)_m$, $NCH_3$ and $C(O)$, provided that after the replacement, O and C(O) in the ring are not adjacent to each other. Its example includes but is not limited to (1S,4S)-2-methyl-2-azabicyclo[2.2.1]hexane, 2-azabicyclo[2.2.1]heptane, 8-methylbicyclo[3.2.1]octane, 3-oxa-8-azabicyclo[3.2.1]octane, 2-azabicyclo[2.2.2]octane, 7-azabicyclo[2.2.1]heptane, 3-azabicyclo[3.2.1]octane, 3-azabicyclo[3.3.2]decane, 7-oxabicyclo[2.2.1]heptane, 8-oxabicyclo[3.2.1]octane and the like.

As used herein, the term "unsaturated $C_{5-7}$ cyclic hydrocarbyl" refers to a monocyclic unsaturated carbocyclic group containing 5-7, e.g. 5, 6, or 7 carbon atoms. Its example includes but is not limited to cyclopentenyl, cyclohexenyl, cyclohexadienyl, cycloheptenyl, cycloheptadienyl, cycloheptatrienyl and the like.

As used herein, the term "3-8 membered heterocyclyl" refers to a cyclic system consisted of 3-8, e.g. 3, 4, 5, 6, 7 or 8, preferably 5-8 carbon atoms and heteroatoms selected from the group consisting of nitrogen, oxygen and sulfur, and its example includes but is not limited to the groups formed by the following rings: aziridine, 2H-aziridine, diaziridine, 3H-diazirine, azetidine, 1,2-diazetidine, azete, 3,4-dihydro-1,2-diazete, pyrrole, pyrroline, pyrrolidine, imidazole, 4,5-dihydro-imidazole, imidazolidine, pyrazole, 4,5-dihydro-pyrazole, pyrazolidine, 1,2,3-triazole, 1,2,4-triazole, tetrazole, pyridine, 2-pyridinone, 4-pyridinone, piperidine, pyridazine, pyrimidine, pyrazine, piperazine, 1,2,3-triazine, 1,2,4-triazine, 1,3,5-triazine, 1,2,4,5-tetrazine, azepine, 1,2-diazepine, 1,3-diazepine, 1,4-diazepine, azocine, 1,4-dihydro-1,4-diazocine, oxirane, dioxirane, thiirane, oxetane, 1,2-dioxetane, thietane, 1,2-dithiete, furan, tetrahydrofuran, thiene, 2,5-dihydrothiene, tetrahydrothiene, 1,3-dioxolane, 1,3-dioxol-2-one, 1,2-dithiole, 1,3-dithiolane, 2H-pyran, 2H-pyran-2-one, 3,4-dihydro-2H-pyran, 4H-pyran, tetrahydro pyran, 4H-pyran-4-one, 1,4-dioxine, 1,4-dithiine, 1,4-oxathiine, 1,4-dioxane, 1,3-dioxane, 1,3-oxathiane, oxepine, thiepine, 1,4-dioxocine, oxaziridine, oxazole, 4,5-dihydrooxazole, isoxazole, 4,5-dihydroisoxazole, 2,3-dihydroisoxazole, 1,2,3-oxadiazole, 1,2,5-oxadiazole, thiazole, 4,5-dihydrothiazole, isothiazole, 1,2,3-thiadiazole, 1,2,4-thiadiazole, 1,3,4-thiadiazole, 2H-1,2-oxazine, 4H-1,2-oxazine, 6H-1,2-oxazine, 2H-1,3-ox azine, 4H-1,3-oxazine, 5,6-dihydro-4H-1,3-oxazine, 6H-1,3-ox azine, 2H-1,4-oxazine, 4H-1,4-oxazine, 2H-1,3-thiazine, 4H-1,3-thiazine, 5,6-dihydro-4H-1,3-thiazine, 6H-1,3-thiazine, 2H-1,4-thiazine, 4H-1,4-thiazine, morpholine and the like.

The present compound of formula (I) can be used in its free form or the form of its pharmaceutically acceptable salt. The pharmaceutically acceptable salt of the formula (I) compound of the present invention comprises the salts formed at the site of the basic group such as amino and the salts formed at the site of the acidic group such as hydroxyl and carboxyl. The salt formed at the site of the basic group includes a salt that is formed with an inorganic acid, such as hydrochloride, hydrobromide, sulfate and the like; a salt that is formed with an organic carboxylic acid, such as tartrate, formate, acetate, lactate, citrate, trichloroacetate, trifluoroacetate and the like; a salt that is formed with sulfonic acid, such as mesylate, benzenesulfonate, para-tosylate, naphthalenesulfonate, and the like. The salt form at the site of the acidic group includes a salt that is formed with an alkali metal such as sodium, potassium and the like; a salt that is formed with an alkaline earth metal such as calcium, magnesium and the like; an ammonium salt; a salt that is formed with a nitrogen-containing organic base, said organic base includes, but is not limited to trimethylamine, triethylamine, tributylamine, pyridine N,N-dimethylphenylamine, N-methylpiperidine, N-methylmorpholine, diethylamide, dicyclohexyl amine, procaine, dibenzylamine, N-benzyl-β-phenylethylamine, 1-diphenylhydroxylmethylamine, N,N'-dibenzyl ethylene diamine and the like.

The present compound of formula (I) includes any mixture of all of possible optical isomers/diastereoisomers and pure or partially pure compounds. The present invention comprises all stereoisomeric forms of these compounds.

The present compound of formula (I) contains olefinic double bonds. Unless otherwise specified, the present invention includes its cis-isomer and its trans-isomer.

The present compound of formula (I) can be present in a form of tautomer. Each of tautomers and a mixture thereof are comprised in the scope of the present invention.

In one preferable embodiment of the present compound of the general formula (I), $R^1$ is selected from the group consisting of the following groups that are unsubstituted or substituted by 1-2 $Q_1$ substituents: a 6-10-membered saturated fused ring-$C_{0-4}$alkyl group, a 7-10-membered saturated spiro ring-$C_{0-4}$alkyl group or a 7-10-membered saturated bridged ring-$C_{0-4}$alkyl group, wherein 1-3 carbon atoms of said fused ring, spiro ring or bridged ring can be replaced with 1-3 hetero atoms and/or groups that can be identical or different and are selected from the group consisting of O, $S(O)_m$, $N(H)_m$, $NCH_3$ and $C(O)$, provided that after the replacement, O and C(O) in the ring are not adjacent to each other, $Q_1$ is selected from the group consisting of halogen, hydroxyl, amino, carboxyl, cyano, a $C_{1-4}$alkyl group, a $C_{1-4}$alkoxyl group, a $C_{1-4}$alkylamino group, a di($C_{1-4}$alkyl)amino group, a $C_{1-4}$alkylcarbonyloxy group, a $C_{1-4}$alkylacylamino group, a $C_{1-4}$alkylsulfonyl group, a $C_{1-4}$alkylsulfinyl group, $C_{1-4}$alkylsulfonylamino and $C_{3-6}$cycloalkyl;

$R^2$ is selected from the group consisting of hydrogen, a $C_{1-4}$alkyl group or a $C_{1-4}$alkoxyl group that is unsubstituted or substituted by 1-2 $Q_2$ substituents, a formyl group that is substituted by a $Q_2$ substituent or $N(H)_m$, $Q_2$ is selected from the group consisting of halogen, hydroxyl, amino, cyano, a $C_{1-4}$alkyl group, a $C_{1-4}$alkoxyl group, a $C_{1-4}$alkylamino group, a di($C_{1-4}$alkyl)amino group, a $C_{1-4}$alkylcarbonyloxy group, a $C_{1-4}$alkylacylamino group, a $C_{1-4}$alkylsulfonyl group, a $C_{1-4}$alkylsulfinyl group, a $C_{1-4}$alkylsulfonylamino group, a $C_{3-6}$cycloalkyl group, an unsaturated $C_{5-7}$ cyclic hydrocarbyl and a saturated or unsaturated 5-8-membered heterocyclyl group, wherein the $C_{3-6}$cycloalkyl, the unsaturated $C_{5-7}$ cyclic hydrocarbyl and the saturated or unsaturated 5-8-membered heterocyclyl can be further substituted by 1-2 $Q_3$ substituents, $Q_3$ is selected from the group consisting of halogen, hydroxyl, amino, cyano, a $C_{1-4}$alkyl group, a $C_{1-4}$alkoxyl group, a $C_{1-4}$alkylamino group, a di($C_{1-4}$alkyl)amino group, a $C_{1-4}$alkylcarbonyloxy group, a $C_{1-4}$alkylacylamino group, a $C_{1-4}$alkylsulfonyl group, a $C_{1-4}$alkylsulfinyl group, a $C_{1-4}$alkylsulfonylamino group and a halogen-substituted $C_{1-4}$alkoxy group;

$R^3$ is selected from the group consisting of halogen, cyano, nitro, a $C_{1-4}$alkyl group, a $C_{1-4}$alkoxyl group, a $C_{1-4}$alkyl group or a $C_{1-4}$alkoxyl group that is substituted by halogen, a $C_{1-4}$alkylcarbonyloxy group, a $C_{1-4}$alkylacylamino group, a $C_{1-4}$alkylsulfonyl group, a $C_{1-4}$alkylsulfinyl group or a $C_{1-4}$alkylsulfonylamino group;

$R^4$, $R^5$ and $R^6$ are each independently selected from the group consisting of hydrogen, halogen, a $C_{1-4}$alkyl group, a $C_{1-4}$alkoxyl group, a $C_{1-4}$alkyl group or a $C_{1-4}$alkoxyl group that is substituted by halogen, a $C_{1-4}$alkylamino group or a di($C_{1-4}$alkyl)amino group;

L is selected from the group consisting of a covalent bond, O, $S(O)_m$ or $N(H)_m$;

n is 1, 2 or 3; and m is 0, 1 or 2.

In another preferable embodiment of the present compound of the general formula (I), $R^1$ is selected from the group consisting of the following groups that are unsubstituted or substituted by 1-2 $Q_1$ substituents;

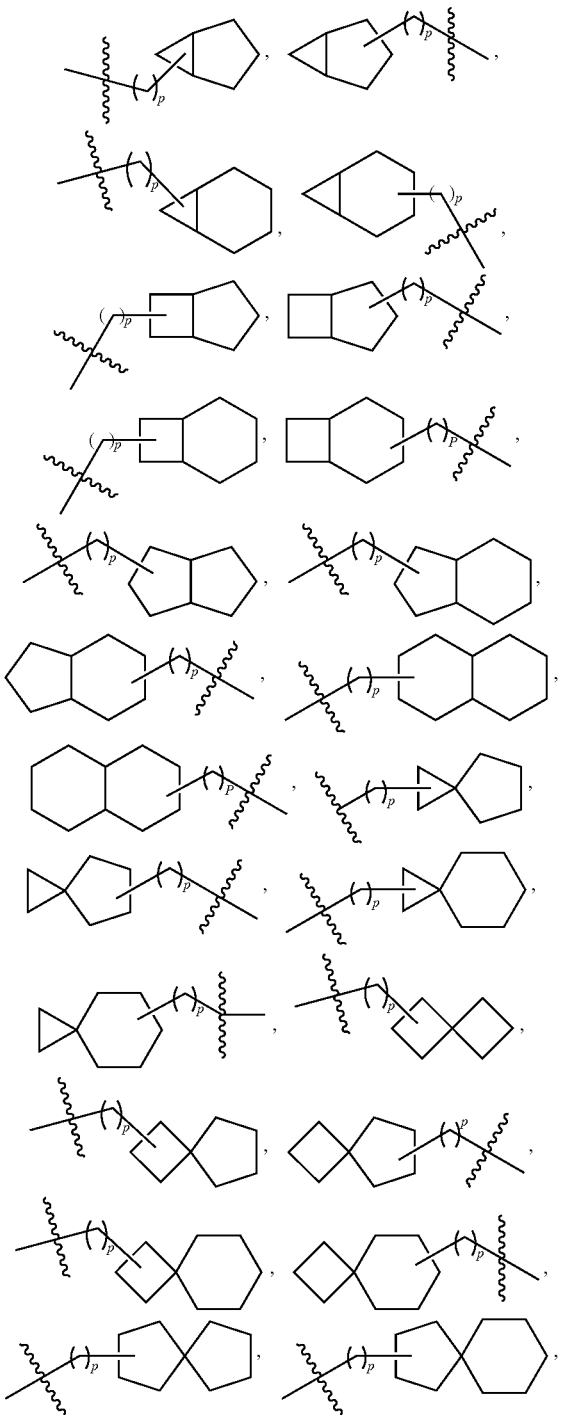

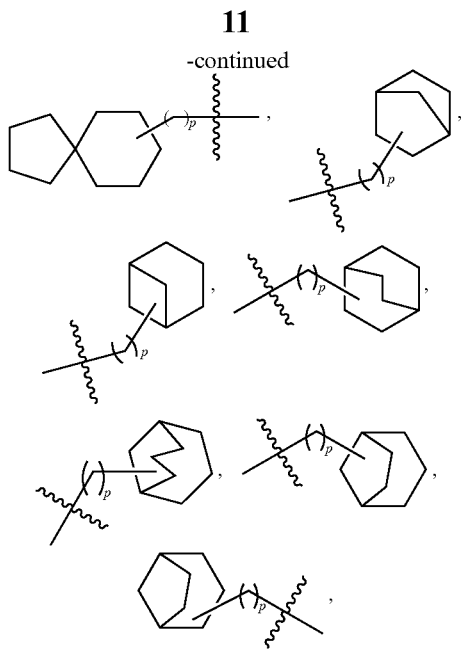

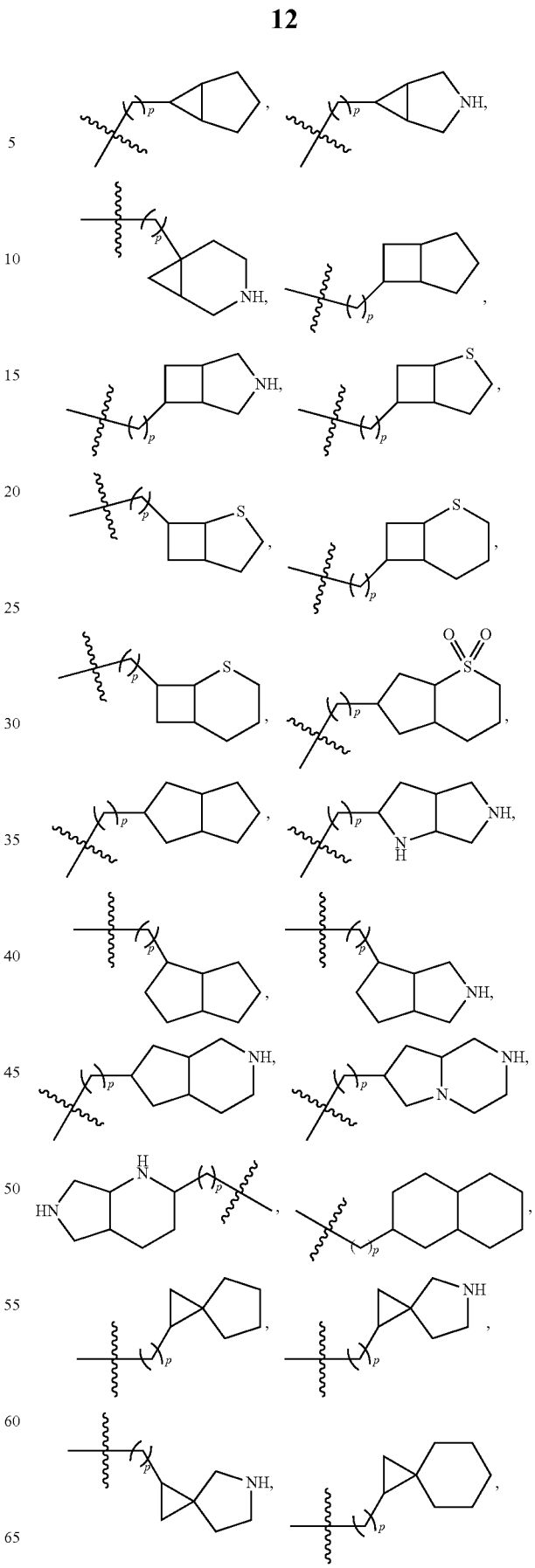

wherein 1-3 carbon atoms on the ring can be replaced with 1-3 hetero atoms and/or groups that can be identical or different and are selected from the group consisting of O, $S(O)_m$, $N(H)_m$, $NCH_3$ and $C(O)$, provided that after the replacement, O and C(O) in the ring are not adjacent to each other, p is 0, 1 or 2, $Q_1$ is selected from the group consisting of halogen, hydroxyl, amino, carboxyl, a $C_{1-4}$alkyl group, a $C_{1-4}$alkoxyl group, a $C_{1-4}$alkylamino group, a di($C_{1-4}$alkyl)amino group and a $C_{3-6}$cycloalkyl group;

$R^2$ is selected from the group consisting of hydrogen, a $C_{1-4}$alkyl group that is unsubstituted or substituted by 1-2 $Q_2$ substituents, a formyl group that is substituted by a $Q_2$ substituent or $N(H)_m$, $Q_2$ is selected from the group consisting of halogen, hydroxyl, amino, a $C_{1-4}$alkyl group, a $C_{1-4}$alkoxyl group, a $C_{1-4}$alkylamino group, a di($C_{1-4}$alkyl)amino group, a $C_{1-4}$alkylcarbonyloxy group, a $C_{1-4}$alkylacylamino group, a $C_{1-4}$alkylsulfonyl group, a $C_{1-4}$alkylsulfonylamino group, a $C_{3-5}$cycloalkyl group and a saturated or unsaturated 5-8-membered heterocyclyl group, wherein the $C_{3-5}$cycloalkyl, the saturated or unsaturated 5-8-membered heterocyclyl can be substituted by 1-2 $Q_3$ substituents, $Q_3$ is selected from the group consisting of halogen, hydroxyl, amino, a $C_{1-4}$alkyl group, a $C_{1-4}$alkoxyl group, a $C_{1-4}$alkylamino group, a di($C_{1-4}$alkyl)amino group, a $C_{1-4}$alkylcarbonyloxy group, a $C_{1-4}$alkylacylamino group, a $C_{1-4}$alkylsulfonyl group, a $C_{1-4}$alkylsulfonylamino group and a halogen-substituted $C_{1-4}$alkoxy group;

$R^3$ is selected from the group consisting of fluoro, chloro, bromo, a $C_{1-4}$alkyl group or a $C_{1-4}$alkoxy group;

$R^4$, $R^5$ and $R^6$ are each independently selected from the group consisting of hydrogen, fluoro or chloro;

L is selected from the group consisting of a covalent bond, O, $S(O)_m$ or $N(H)_m$;

n is 1, 2 or 3; and m is 0, 1 or 2.

In another preferable embodiment of the present compound of the general formula (I), $R^1$ is selected from the group consisting of the following groups that are unsubstituted or substituted by 1-2 $Q_1$ substituents:

-continued

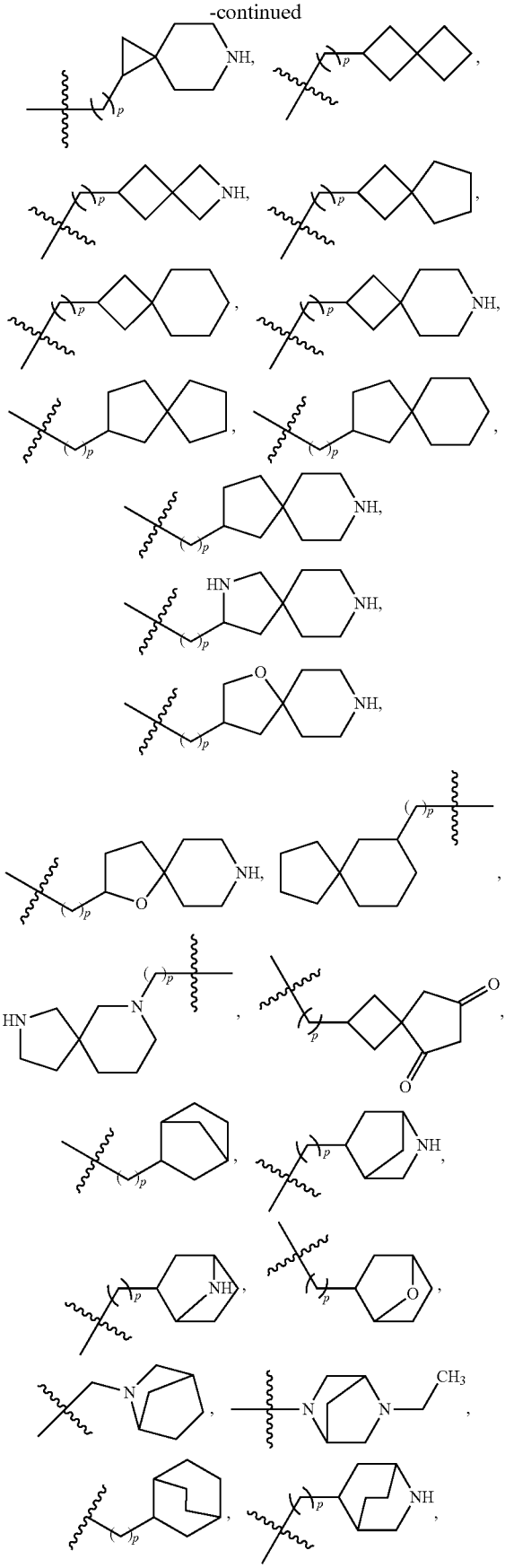

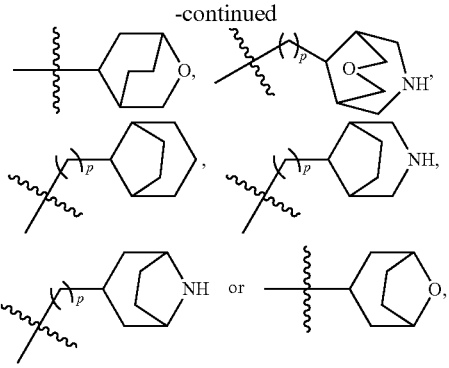

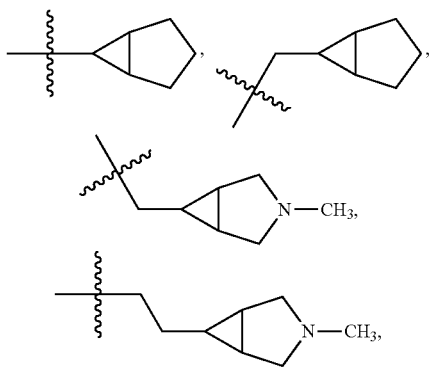

p is 0, 1 or 2, $Q_1$ is selected from the group consisting of halogen, amino, a $C_{1-4}$alkyl group, a $C_{1-4}$alkylamino group and a di($C_{1-4}$alkyl)amino group;

$R^2$ is selected from the group consisting of hydrogen, methyl that is unsubstituted or substituted by 1-2 $Q_2$ substituents or ethyl that is unsubstituted or substituted by 1-2 $Q_2$ substituents, a formyl group that is substituted by a $Q_2$ substituent or $N(H)_m$, $Q_2$ is selected from the group consisting of:

(1) halogen, hydroxyl, amino, a $C_{1-4}$alkoxyl group, a $C_{1-4}$alkylamino group, a di($C_{1-4}$alkyl)amino group, acetoxyl, acetamido, methylsulfonyl and methylsulfonylamino, (2) cyclopropyl, cyclopentyl, piperidinyl, piperazinyl, morpholinyl, pyrrolidinyl, furyl, thienyl, pyrrolyl, imidazolyl, thiazolyl, isothiazolyl, oxazolyl, pyridyl, pyrazinyl and pyrimidinyl, these $Q_2$ groups can be further substituted by 1-2 $Q_3$ substituents, $Q_3$ is selected from the group consisting of halogen, hydroxyl, amino, a $C_{1-4}$alkyl group, a $C_{1-4}$alkoxyl group, a $C_{1-4}$alkylamino group, a di($C_{1-4}$alkyl)amino group, a halogen-substituted $C_{1-4}$alkoxyl, acetoxyl, acetamido, methylsulfonyl and methylsulfonylamino;

$R^3$ is selected from the group consisting of fluoro or chloro;

$R^4$, $R^5$ and $R^6$ are hydrogen;

L is selected from the group consisting of a covalent bond or O;

n is 2; and m is 0, 1 or 2.

In another preferable embodiment of the present compound of the general formula (I), $R^1$ is selected from the group consisting of:

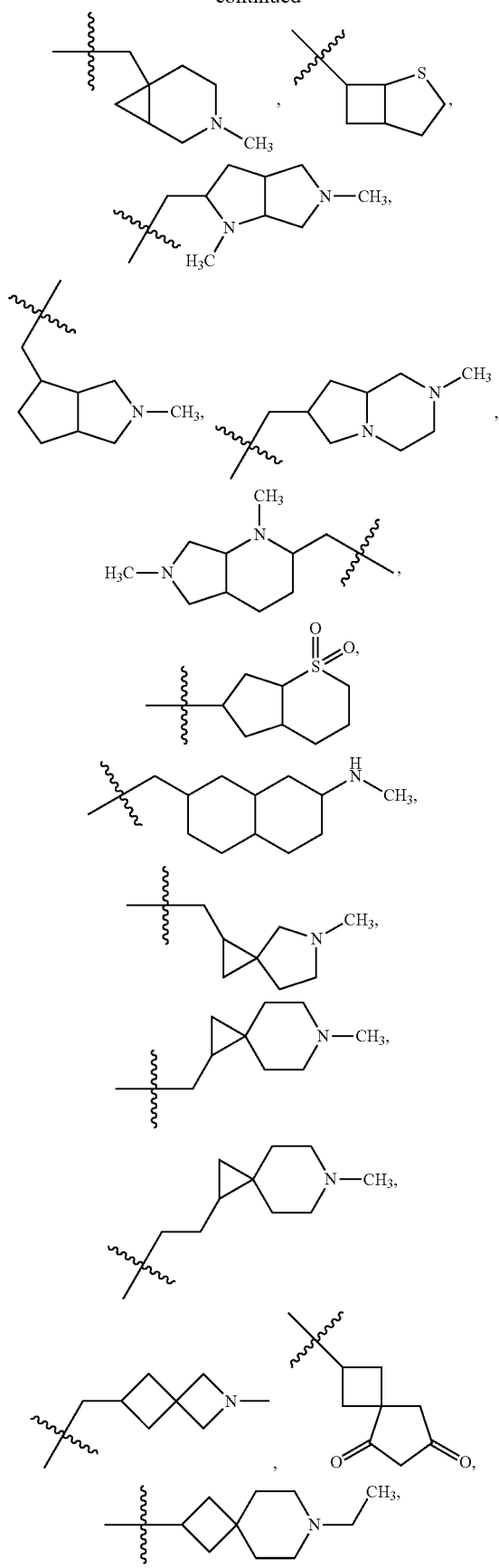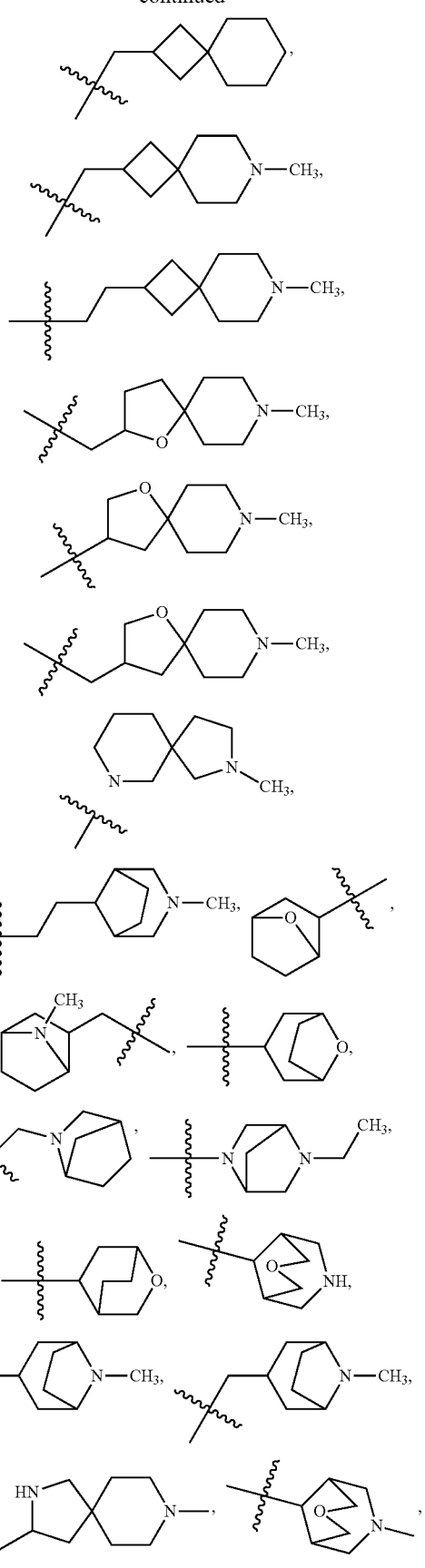

-continued

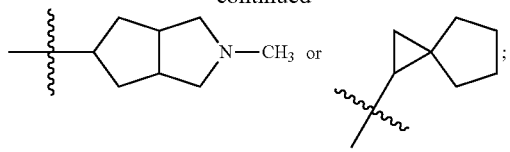

R² is selected from the group consisting of hydrogen, methyl that is unsubstituted or substituted by 1-2 Q₂ substituents or ethyl that is unsubstituted or substituted by 1-2 Q₂ substituents, Q₂ is selected from the group consisting of:
(1) methoxy and a di($C_{1-4}$alkyl)amino group,
(2) piperidinyl, piperazinyl, morpholinyl, pyrrolidinyl, furyl, cyclopropyl, cyclopentyl, pyrrolyl, pyridyl, pyrimidinyl and thiazolyl, these Q₂ groups can be further substituted by 1-2 Q₃ substituents, Q₃ is selected from the group consisting of halogen, hydroxy, amino, a $C_{1-4}$alkyl group, a $C_{1-4}$alkoxyl group, a $C_{1-4}$alkylamino group, a di($C_{1-4}$alkyl)amino group and a halogen-substituted $C_{1-4}$alkoxy group;

R³ is selected from the group consisting of fluoro or chloro;
R⁴, R⁵ and R⁶ are hydrogen;
L is selected from the group consisting of a covalent bond or O; and
n is 2.

In another preferable embodiment of the present compound of the general formula (I), R¹ is selected from the group consisting of:

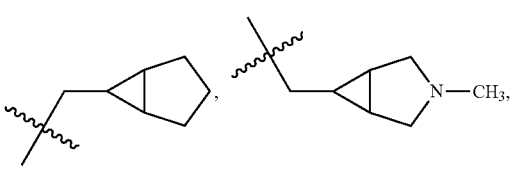

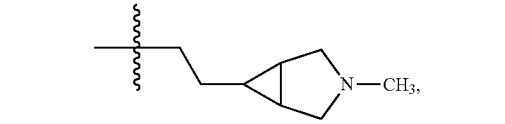

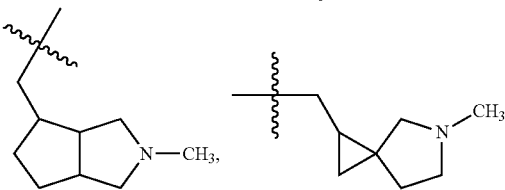

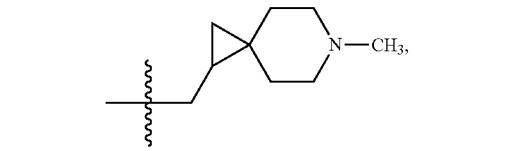

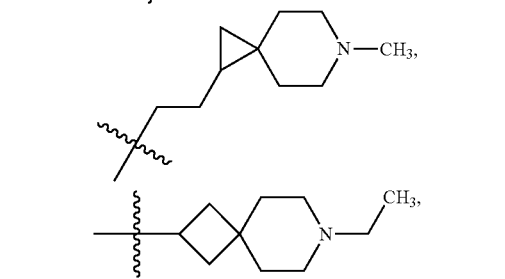

-continued

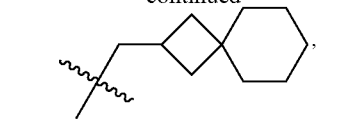

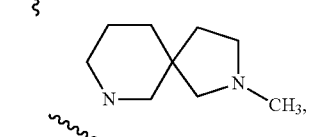

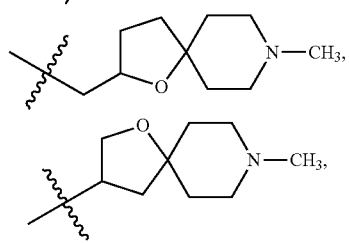

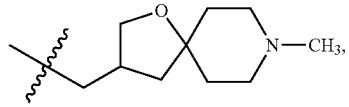

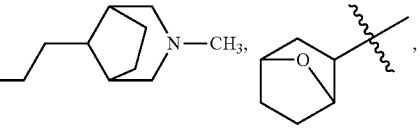

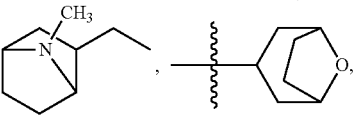

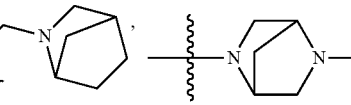

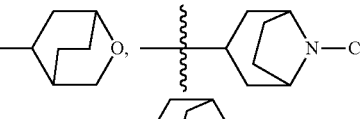

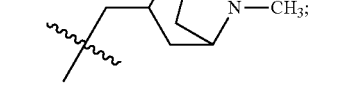

R² is selected from the group consisting of hydrogen, methyl that is unsubstituted or substituted by 1-2 Q₂ substituents or ethyl that is unsubstituted or substituted by 1-2 Q₂ substituents, Q₂ is selected from the group consisting of methoxy, dimethylamino, diethylamino, piperidinyl, piperazinyl and morpholinyl;

R³ is selected from the group consisting of fluoro or chloro;
R⁴, R⁵ and R⁶ are hydrogen;

L is selected from the group consisting of a covalent bond or O; and
n is 2.

The particularly preferable compound according to the present invention includes the following compounds and their pharmaceutically acceptable salts and stereoisomers:

| Compound | Name | Structure |
|---|---|---|
| 1 | (E)-N-[7-(8-oxabicyclo[3.2.1]octan-3-yloxy)-4-(3-chloro-4-fluorophenylamino)quinazolin-6-yl]-4-(piperidin-1-yl)-2-butenamide | 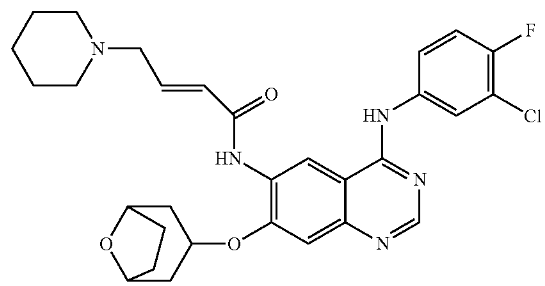 [SMILES: O=C(/C=C/CN1CCCCC1)Nc1cc2c(Nc3ccc(F)c(Cl)c3)ncnc2cc1OC1CC2CCC(C1)O2] |
| 2 | (E)-N-[7-(7-oxabicyclo[2.2.1]heptan-2-yloxy)-4-(3-chloro-4-fluorophenylamino)quinazolin-6-yl]-4-(piperidin-1-yl)-2-butenamide | 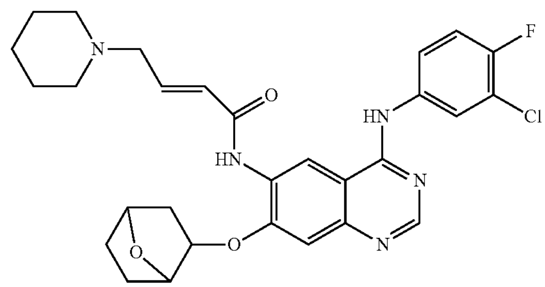 [SMILES: O=C(/C=C/CN1CCCCC1)Nc1cc2c(Nc3ccc(F)c(Cl)c3)ncnc2cc1OC1CC2CCC1O2] |
| 3 | (E)-N-[4-(3-chloro-4-fluorophenylamino)-7-(2-methyl-2,7-diazaspiro[4.5]decan-7-yl)quinazolin-6-yl]-4-(piperidin-1-yl)-2-butenamide | 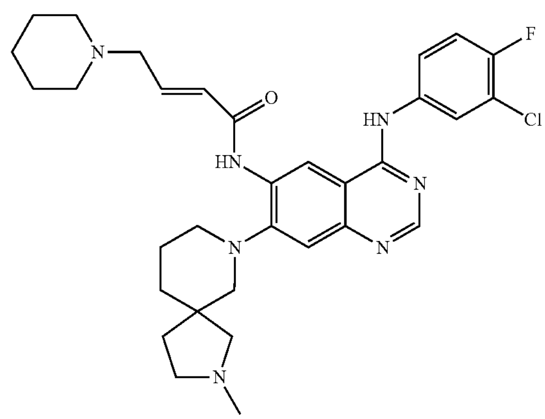 [SMILES: CN1CCC2(CCCN(c3cc4ncnc(Nc5ccc(F)c(Cl)c5)c4cc3NC(=O)/C=C/CN3CCCCC3)C2)C1] |
| 4 | N-[4-(3-chloro-4-fluorophenylamino)-7-(8-methyl-8-azabicyclo[3.2.1]octan-3-yloxy)quinazolin-6-yl]-acrylamide | 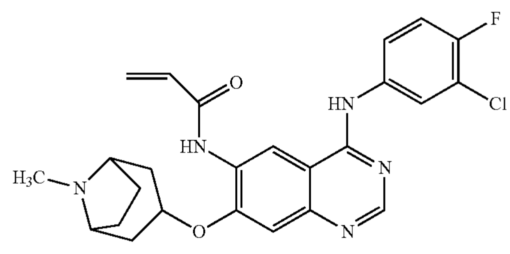 [SMILES: C=CC(=O)Nc1cc2c(Nc3ccc(F)c(Cl)c3)ncnc2cc1OC1CC2CCC(C1)N2C] |
| 5 | N-[4-(3-chloro-4-fluorophenylamino)-7-(8-methyl-1-oxa-8-azaspiro[4.5]decan-3-yloxy)quinazolin-6-yl]-acrylamide | 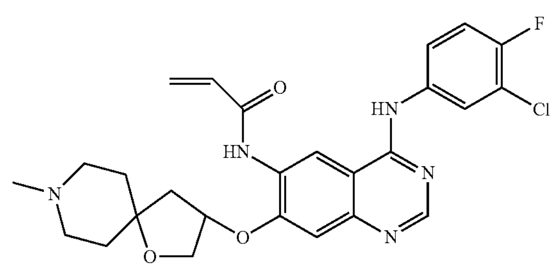 [SMILES: C=CC(=O)Nc1cc2c(Nc3ccc(F)c(Cl)c3)ncnc2cc1OC1COC2(CCN(C)CC2)C1] |

-continued

| Compound | Name | Structure |
|---|---|---|
| 6 | N-[4-(3-chloro-4-fluorophenylamino)-7-((8-methyl-1-oxa-8-azaspiro[4.5]decan-3-yl)methoxy)quinazolin-6-yl]-acrylamide | 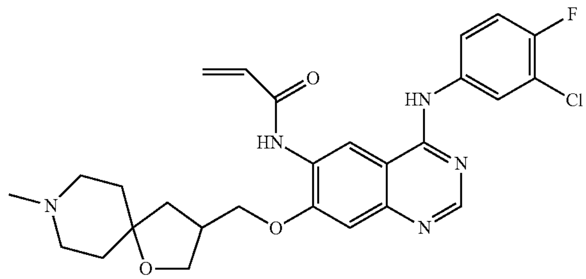 [SMILES: C=CC(=O)Nc1cc2c(Nc3ccc(F)c(Cl)c3)ncnc2cc1OCC1COC2(CCN(C)CC2)C1] |
| 7 | N-[4-(3-chloro-4-fluorophenylamino)-7-(8-methyl-1-oxa-8-azaspiro[4.5]decan-2-ylmethoxy)quinazolin-6-yl]-acrylamide | 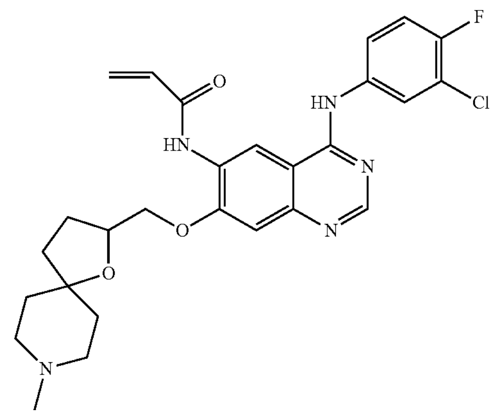 [SMILES: C=CC(=O)Nc1cc2c(Nc3ccc(F)c(Cl)c3)ncnc2cc1OCC1CCC2(CCN(C)CC2)O1] |
| 8 | N-[4-(3-chloro-4-fluorophenylamino)-7-(2-((1R,5S,6S)-3-methyl-3-azabicyclo[3.1.0]hexan-6-yl)ethoxy)quinazolin-6-yl]-acrylamide | 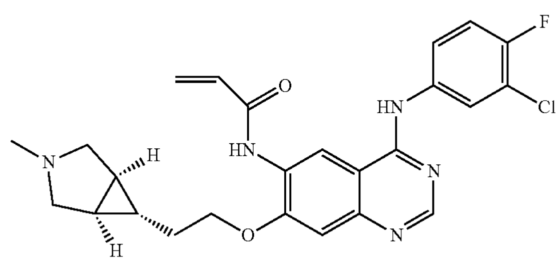 [SMILES: C=CC(=O)Nc1cc2c(Nc3ccc(F)c(Cl)c3)ncnc2cc1OCC[C@@H]1[C@H]2CN(C)C[C@@H]12] |
| 9 | N-[4-(3-chloro-4-fluorophenylamino)-7-((2-methyloctahydrocyclopenta[c]pyrrol-4-yl)methoxy)quinazolin-6-yl]-acrylamide | 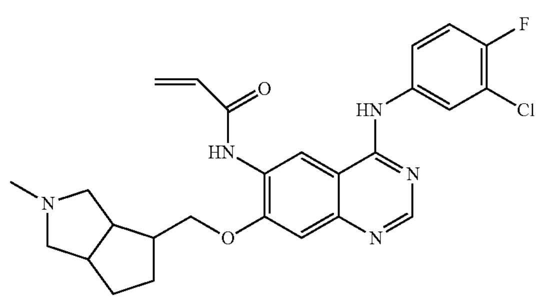 [SMILES: C=CC(=O)Nc1cc2c(Nc3ccc(F)c(Cl)c3)ncnc2cc1OCC1CCC2CN(C)CC12] |
| 10 | N-[4-(3-chloro-4-fluorophenylamino)-7-((7-methyl-7-azabicyclo[2.2.1]heptan-2-yl)methoxy)quinazolin-6-yl]-acrylamide | 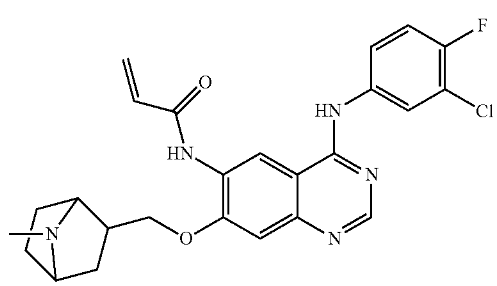 [SMILES: C=CC(=O)Nc1cc2c(Nc3ccc(F)c(Cl)c3)ncnc2cc1OCC1CC2CCC1N2C] |

-continued

| Compound | Name | Structure |
|---|---|---|
| 11 | N-[4-(3-chloro-4-fluorophenylamino)-7-(2-(3-methyl-3-azabicyclo[3.2.1]octan-8-yl)ethoxy)quinazolin-6-yl]-acrylamide | 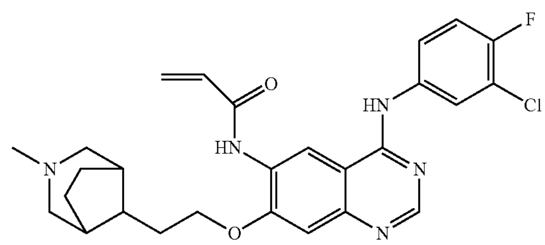 [SMILES: C=CC(=O)Nc1cc2c(Nc3ccc(F)c(Cl)c3)ncnc2cc1OCCC1C2CCC1CN(C)C2] |
| 12 | N-[4-(3-chloro-4-fluorophenylamino)-7-((5-methyl-5-azaspiro[2.4]heptan-1-yl)methoxy)quinazolin-6-yl]-acrylamide | 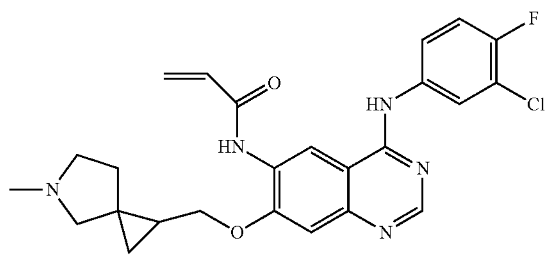 [SMILES: C=CC(=O)Nc1cc2c(Nc3ccc(F)c(Cl)c3)ncnc2cc1OCC1CC12CCN(C)C2] |
| 13 | N-[4-(3-chloro-4-fluorophenylamino)-7-((6-methyl-6-azaspiro[2.5]octan-1-yl)methoxy)quinazolin-6-yl]-acrylamide | 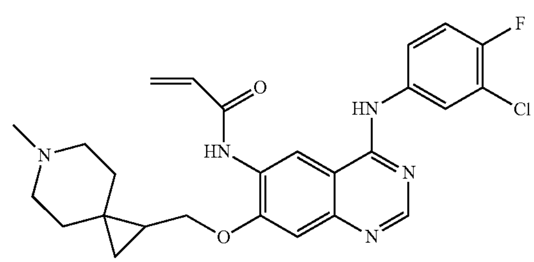 [SMILES: C=CC(=O)Nc1cc2c(Nc3ccc(F)c(Cl)c3)ncnc2cc1OCC1CC12CCN(C)CC2] |
| 14 | N-[4-(3-chloro-4-fluorophenylamino)-7-(2-(6-methyl-6-azaspiro[2.5]octan-1-yl)ethoxy)quinazolin-6-yl]-acrylamide | 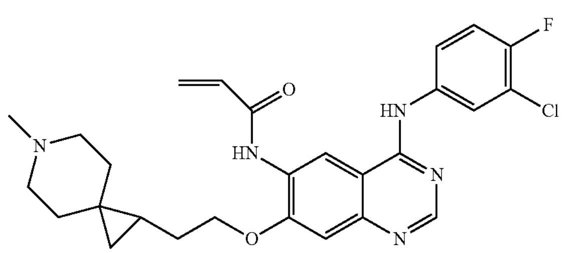 [SMILES: C=CC(=O)Nc1cc2c(Nc3ccc(F)c(Cl)c3)ncnc2cc1OCCC1CC12CCN(C)CC2] |
| 15 | (E)-N-[4-(3-chloro-4-fluorophenylamino)-7-(2-((1R,5S,6S)-3-methyl-3-azabicyclo[3.1.0]hexan-6-yl)ethoxy)quinazolin-6-yl]-2-butenamide | 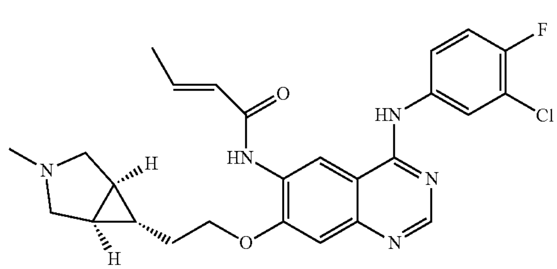 [SMILES: C/C=C/C(=O)Nc1cc2c(Nc3ccc(F)c(Cl)c3)ncnc2cc1OCC[C@@H]1[C@H]2CN(C)C[C@@H]12] |

-continued

| Compound | Name | Structure |
|---|---|---|
| 16 | (E)-N-[4-(3-chloro-4-fluorophenylamino)-7-((7-methyl-7-azaspiro[3.5]nonan-2-yl)methoxy)quinazolin-6-yl]-2-butenamide | 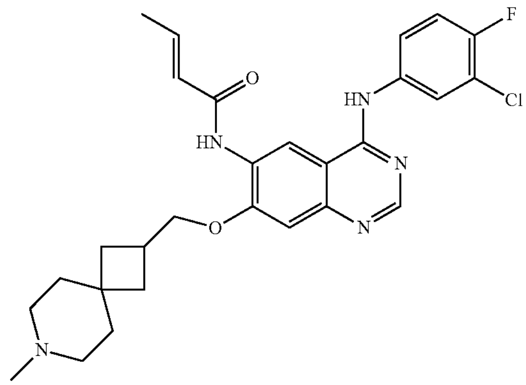 [SMILES: C/C=C/C(=O)Nc1cc2c(Nc3ccc(F)c(Cl)c3)ncnc2cc1OCC1CC2(CCN(C)CC2)C1] |
| 17 | (E)-N-[4-(3-chloro-4-fluorophenylamino)-7-((7-methyl-7-azaspiro[3.5]nonan-2-yl)methoxy)quinazolin-6-yl]-2-pentenamide | 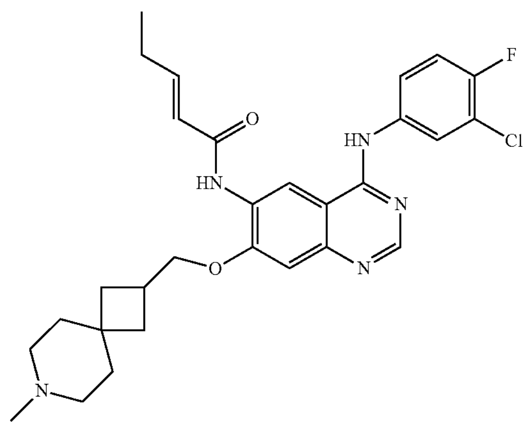 [SMILES: CC/C=C/C(=O)Nc1cc2c(Nc3ccc(F)c(Cl)c3)ncnc2cc1OCC1CC2(CCN(C)CC2)C1] |
| 18 | N-[4-(3-chloro-4-fluorophenylamino)-7-((7-methyl-7-azaspiro[3.5]nonan-2-yl)methoxy)quinazolin-6-yl]-acrylamide | 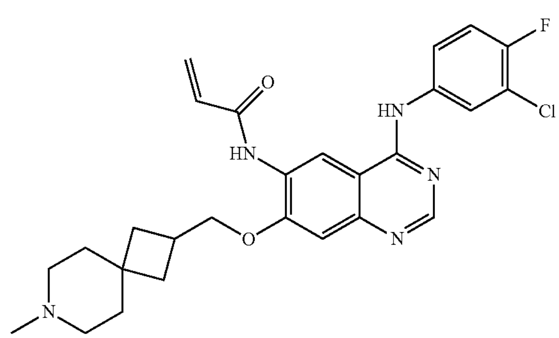 [SMILES: C=CC(=O)Nc1cc2c(Nc3ccc(F)c(Cl)c3)ncnc2cc1OCC1CC2(CCN(C)CC2)C1] |
| 19 | N-[4-(3-chloro-4-fluorophenylamino)-7-(2-(7-methyl-7-azaspiro[3.5]nonan-2-yl)ethoxy)quinazolin-6-yl]-acrylamide | 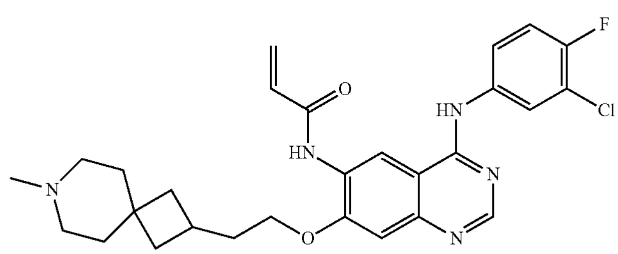 [SMILES: C=CC(=O)Nc1cc2c(Nc3ccc(F)c(Cl)c3)ncnc2cc1OCCC1CC2(CCN(C)CC2)C1] |

-continued

| Compound | Name | Structure |
|---|---|---|
| 20 | (E)-N-(4-(3-chloro-4-fluorophenylamino)-7-((7-methyl-7-azaspiro[3.5]nonan-2-yl)methoxy)quinazolin-6-yl)-4-dimethylamino-2-butenamide | 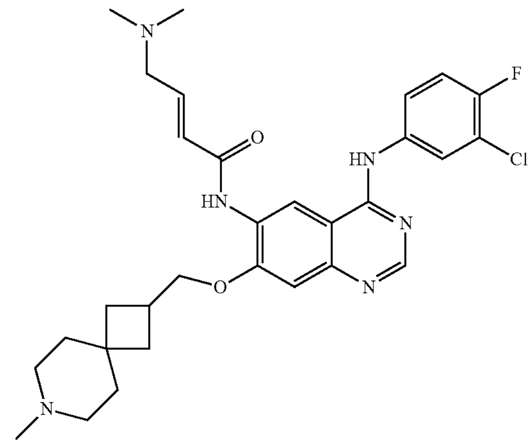 [SMILES: CN(C)C/C=C/C(=O)Nc1cc2c(Nc3ccc(F)c(Cl)c3)ncnc2cc1OCC1CC2(CCN(C)CC2)C1] |
| 21 | (E)-N-[4-(3-chloro-4-fluorophenylamino)-7-((2-(3-methyl-3-aza-bicyclo[3.1.0]-6-hexyl)-ethoxy)quinazolin-6-yl)-4-dimethylamino]-crotonamide | 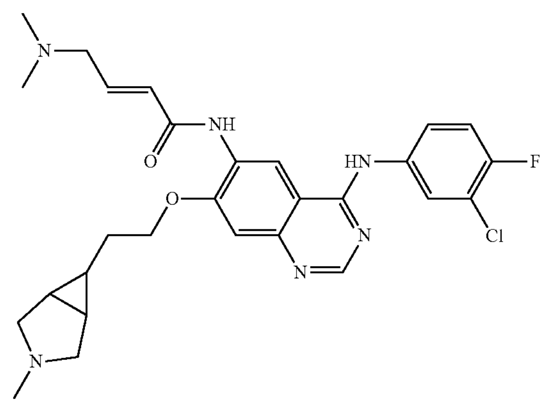 [SMILES: CN(C)C/C=C/C(=O)Nc1cc2c(Nc3ccc(F)c(Cl)c3)ncnc2cc1OCCC1C2CN(C)CC12] |
| 22 | (E)-N-[4-(3-chloro-4-fluorophenylamino)-7-(((spiro[3.5]octan-2-yl)methoxy)quinazolin-6-yl)-4-dimethylamino]-crotonamide | 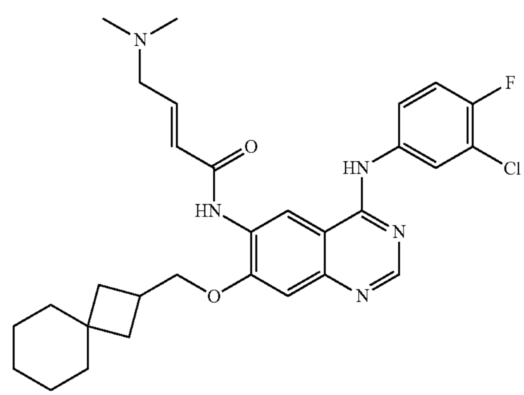 [SMILES: CN(C)C/C=C/C(=O)Nc1cc2c(Nc3ccc(F)c(Cl)c3)ncnc2cc1OCC1CC2(CCCCC2)C1] |
| 23 | (E)-N-(7-(bicyclo[3.1.0]hexan-6-ylmethoxy)-4-(3-chloro-4-fluorophenylamino)quinazolin-6-yl)-4-(dimethylamino)but-2-enamide | 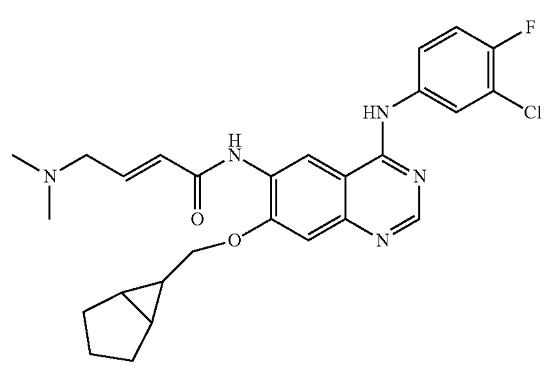 [SMILES: CN(C)C/C=C/C(=O)Nc1cc2c(Nc3ccc(F)c(Cl)c3)ncnc2cc1OCC1C2CCCC21] |

In an embodiment of the preparation of the present compound of the general formula (I), the present compound of the general formula (I) can be prepared by the following specific steps:

Reaction Procedure:

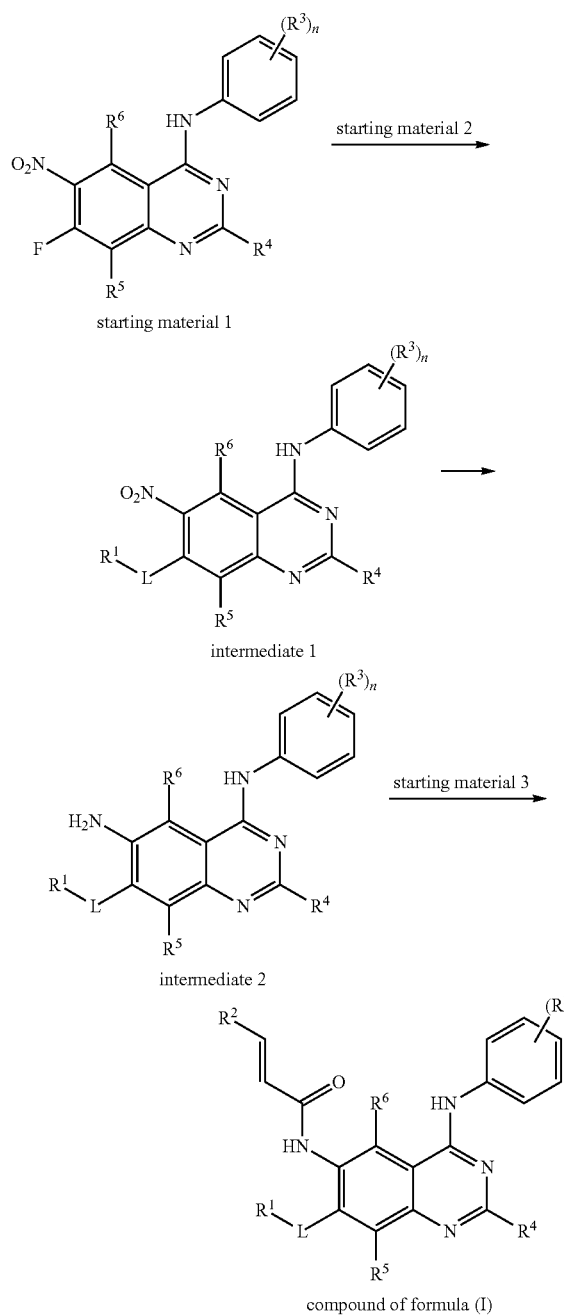

starting material 1 intermediate 1 intermediate 2 compound of formula (I)

In the above Reaction Procedure, $R^1$, $R^2$, $R^3$, $R^4$, $R^5$, $R^6$, L and n are as defined hereinbefore; the starting material 1 is synthesized according to the methodology provided in US 2005/0250761 A1, the starting material 2=$R^1$-LH; the starting material 3=$R^2$CH=CH—C(O)Cl or $R^2$CH=CH—COOH.

1. Preparation of Intermediate 1

(1) Starting material 2 is dissolved in a non-protonic polar solvent (e.g. THF (tetrahydrofuran), DMF (dimethylformamide), acetonitrile or dioxane). To the mixture is added an alkali (e.g. NaH, potassium carbonate, triethylamine or DIEA (diisopropylethylamine)) in batch under stirring. Then to the mixture is added the solid of Starting material 1. The reaction is carried out at room temperature or under heating to reflux for several hours.

(2) The reaction is cooled to room temperature. Water is added. The mixture is filtered. The filtered cake is dried in vacuum to produce the Intermediate 1. Alternatively, the reaction is cooled to room temperature. Water is added. The mixture is extracted with an organic solvent (e.g. ethyl acetate, dichloromethane or chloroform). Then the organic layer is evaporated to dryness to produce the Intermediate 1.

2. Preparation of Intermediate 2

(1) Intermediate 1 is added in batch to a solvent (e.g. ethanol or THF and the like) optionally containing an acid (e.g. acetic acid or diluted hydrochloric acid and the like). Then an reducing agent (e.g. Fe powder, Zn powder, Pd/C or Raney-Ni and the like) is added. The reaction is carried out at room temperature or under heating.

(2) After the completion of reaction, the reaction mixture is cooled to room temperature, and extracted with an organic solvent (e.g. dichloromethane, ethyl acetate or chloroform and the like). The organic layer is evaporated to dryness. The resulting crude product can be purified by a column chromatography (a silica gel column or a preparative chromatography column) to produce Intermediate 2.

3. Preparation of Compound of Formula (I)

(1) Intermediate 2 is dissolved in an organic solvent (e.g. THF, dichloromethane, acetonitrile or DMF and the like). To the mixture are successively added an organic base (e.g. triethylamine or DIEA and the like) and Starting material 3. The mixture is stirred at room temperature for several hours to react. Alternatively Intermediate 2, Starting material 3 and an organic base (e.g. DIEA or triethylamine and the like) are dissolved in an organic solvent (e.g. dichloromethane, DMF, THF, acetonitrile or DMF and the like). An condensing agent (e.g. HATU (2-(7-azobenzotriazol-1-yl)-N,N,N',N'-tetramethyluronium hexafluorophosphate), EDC (1-ethyl-3-(3-dimethylaminopropyl)carbodiimide) or DCC (N,N'-dicyclohexylcarbodiimide) and the like) are added.

(2) Water is added to the reaction mixture, and the mixture is extracted with an organic solvent (e.g. dichloromethane, ethyl acetate or chloroform and the like). The organic layers are combined. The resulting residue is purified by a column chromatography (a silica gel column or a preparative chromatography column) to produce Compound of formula (I).

The present compound of general formula (I) and a pharmaceutically acceptable salt and a stereoisomer thereof can be administered to a mammal, e.g. human orally, parenterally (intravenously, intramuscularly, subcutaneously or rectally and the like), pulmonarily, and locally. The daily dosage of the present compound can be about 1 to about 1000 mg.

The present compound of formula (I) or a pharmaceutically acceptable salt, or a stereoisomer thereof can be administered alone or in combination with other therapeutical agents, in particular a second therapeutical agent selected from the group consisting of an antineoplastic agent and an immunosuppressive agent. Said second therapeutical agent is selected from the group consisting of antimetabolite, including but not limited to e.g. capecitabine, gemcitabine and the like; a growth factor inhibitor, including but not limited to e.g. pazopanib, imatinib and the like; an antibody, including but not limited to e.g. herceptin, bevacizumab and the like; a mitotic inhibitor, including but not limited to e.g. paclitaxel, vinorelbine, docetaxel, doxorubicin and the like; antineoplastic hormone, including but not limited to e.g. letrozole, tamoxifen, fulvestrant and the like; alkylating agent, including but not limited to e.g. cyclophosphamide, carmustine and the like; a metal platinum, including but not limited to e.g. carboplatin, cisplatin, oxaliplatin and the like; topoisomerase inhibitor, including but not limited to e.g. topotecan and the like; immunosuppressant, including but not limited to e.g. everolimus and the like. All of components to be administered can be administered at the same time or successively and separately in a form of the single formulation or in a combination of the divided formulations.

The present compound of formula (I), a pharmaceutically acceptable salt thereof or a stereoisomer thereof can be used to treat a hyperplasia disease and a chronic obstructive pulmonary disease. The hyperplasia disease includes cancerous disease and non-cancerous disease. The cancerous disease is selected from the group consisting of cerebroma, lung cancer, nonsmall-cell lung cancer, squamous cell, bladder carcinoma, gastric cancer, ovarian cancer, peritoneal cancer, pancreatic cancer, mammary cancer, head and neck cancer, cervical cancer, endometrial cancer, colorectal cancer, liver cancer, renal carcinoma, adenocarcinoma of esophagus, esophageal squamous cell cancer, solid tumor, non-Hodgkin lymphoma, central nervous system tumor (glioma, gliobastona multiforme, glioma sarcomatosum), prostate carcinoma or thyroid carcinoma; the non-cancerous disease is for example benign hyperplasia of skin or prostate.

The present invention also provides a pharmaceutical composition, containing the present compound of general formula (I) or a pharmaceutically acceptable salt, or a stereoisomer thereof as described above and one or more pharmaceutically acceptable carriers and/or diluents. Said composition can be prepared by mixing the present compound of general formula (I) or a pharmaceutically acceptable salt, or a stereoisomer thereof and one or more conventional pharmaceutically acceptable carrier and/or diluent. Said composition can be prepared into any clinically or pharmaceutically acceptable dosage form to administer orally, parenteral, pulmonary or locally to the patient in need thereof.

For the oral administration, the present compound of general formula (I) or a pharmaceutically acceptable salt, or a stereoisomer thereof can be formulated into a conventional solid preparation, such as tablet, capsule, pill, granule, powder and the like; or the oral liquid preparation, such as an oral solution, an oral suspension, a syrup and the like. For preparing the oral preparation, suitable filler, binder, disintegrant, lubricant, diluent and the like can be added. Conventional filler includes starch, sugar powder, calcium phosphate, calcium sulfate dihydrate, dextrin, microcrystalline cellulose, lactose, pregelatinized starch, mannitol and the like. Conventional binder includes sodium carboxymethylcellulose, PVP-K30, hydroxypropyl cellulose, starch paste, methyl cellulose, ethyl cellulose, hypromellose, gelatinized starch and the like. Conventional disintegrant includes dry starch, polyvinylpolypyrrolidone (cPVP), croscarmellose sodium, sodium carboxymethyl starch, low-substituted hydroxypropyl cellulose and the like. Conventional lubricant includes magnesium stearate, talc powder, sodium dodecylsulfate, gum acacia and the like. Conventional diluent includes water, ethanol, glycerin and the like.

For the parenteral administration, according to the conventional method, the present compound of general formula (I) or a pharmaceutically acceptable salt, or a stereoisomer thereof can be formulated into an injectable preparation, including an injection solution, a sterile injection powder and a concentrated injection solution. For preparing the injectable preparation, a conventional method in the pharmaceutical production can be used, and an aqueous solvent or a nonaqueous solvent can be used. The most commonly used aqueous solvent is water for injection. 0.9% aqueous NaCl solution or other suitable aqueous solution can also be used. The most commonly used nonaqueous solvent is vegetable oil, such as soy oil for injection. The aqueous solution of ethanol, propylene glycol, polyethylene glycol or the like can also be used. For preparing the injectable preparation, an additive can be optionally added, depending on the nature of drug. The additive includes an osmotic regulator, a pH-value regulator, a solubilizer, a filler, an antioxidant, a bacteriostatic agent, an emulsifier, a suspending agent or the like.

For the rectal, pulmonary or local administration, the present compound of general formula (I) or a pharmaceutically acceptable salt, or a stereoisomer thereof can be formulated into a suppository, an inhalant, a spraying agent, an ointment, a cream, a gel, a powder, a lotion, a drop, a transdermal patch and the like according to the conventional method.

It is demonstrated that the present invention has an excellent antineoplastic effect. The present invention is therefore expected to have a good therapeutic effect on a hyperplasia disease and a chronic obstructive pulmonary disease and reduce the formation of drug resistance. In addition, it is easy to prepare the present compound; the present invention has a stable quality, and therefore the present invention is apt to be produced on the industrial scale.

BEST MODE OF CARRYING OUT THE INVENTION

The following examples are intended to illustrate the invention and are not to be construed as being limitations thereon. All of the technical solutions that can be accomplished based on the above disclosure fall in the scope of the present invention.

In the examples, the used starting materials are commercially available, for example, from Jingyan Chemicals (Shanghai); Titan chemical (Shanghai); Darui (Shanghai); Ouhechem (Beijing); Tetranov Biopharm (Zhengzhou); Guanghan Bio-Tech (Sichuan); Accela ChemBio (Shanghai); Alfa Aesar (Tianjin); TCI (Shanghai), J&K (Beijing); and Bepharm (Shanghai).

For convenience, the following well-known abbreviations are used hereinafter to describe the compounds.
DMF: dimethylformamide
THF: tetrahydrofuran
DIPEA/DIEA: diisopropylethylamine
EA: ethyl acetate
EtOH: ethanol
DCM: dichloromethane
MeOH: methanol
HATU: 2-(7-azobenzotriazol-1-yl)-N,N,N',N'-tetramethyluronium hexafluorophosphate
DCC: N,N-dicyclohexylcarbodiimide
EDC: 1-ethyl-3-(3-dimethylaminopropyl)carbodiimide
DMAP: 4-dimethylaminopyridine

I. PREPARATION EXAMPLES FOR THE PRESENT COMPOUND

N-(4-(3-chloro-4-fluorophenyl))-7-fluoro-6nitroquinazolin-4-amine, as the starting material for the present compound, was prepared according to US 2005/0250761 A1:

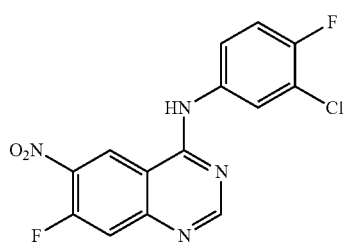 [SMILES: O=[N+]([O-])c1cc2c(Nc3ccc(F)c(Cl)c3)ncnc2cc1F]

The steps were as follows:
Reaction Procedures:

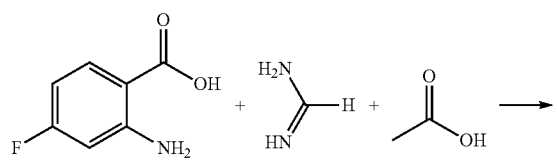

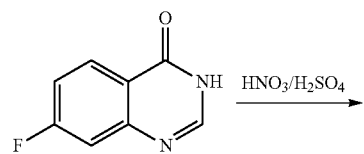

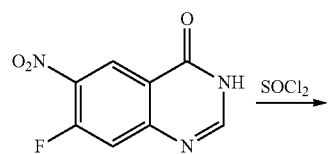

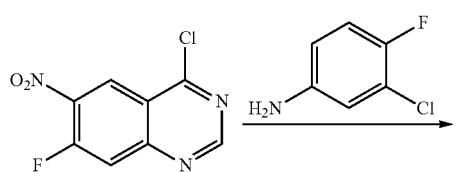

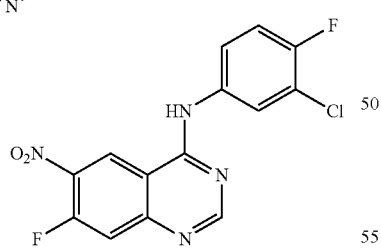

2-amino-4-fluorobenzoic acid, acetic acid and formamidine were reacted under heating to reflux in the presence of 2-methoxyethanol to produce 7-fluoro-3H-quinazolin-4-one. The resulting product was nitrified to produce 7-fluoro-6-nitro-3H-quinazolin-4-one, which was treated with thionyl chloride to produce 4-chloro-6-nitro-7-fluoro-3H-quinazoline. The resulting product was dissolved in isopropanol, 4-fluoro-3-chlorophenylamine was added to produce N-(4-(3-chloro-4-fluorophenyl))-7-fluoro-6nitroquinazolin-4-amine.

Example 1 Preparation of (E)-N-[7-(8-oxabicyclo[3.2.1]octan-3-yloxy)-4-(3-chloro-4-fluorophenylamino)quinazolin-6-yl]-4-(piperidin-1-yl)-2-butenamide (Compound 1)

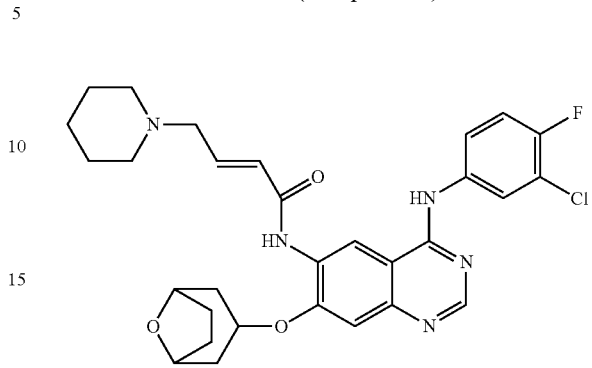

(1) Preparation of 7-(8-oxabicyclo[3.2.1]octan-3-yloxy)-N-(4-(3-chloro-4-fluorophenyl))-6-nitroquinazolin-4-amine

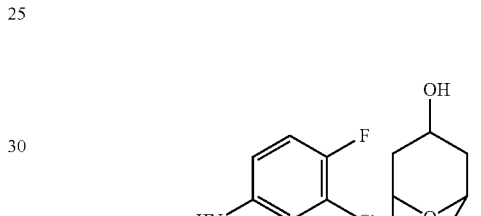

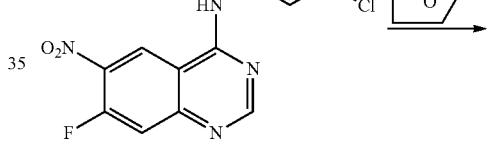

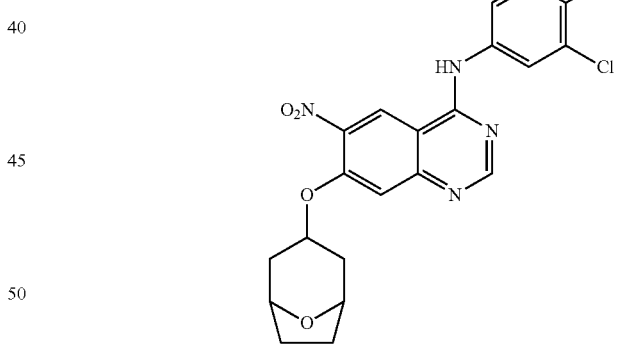

To a round-bottom flask containing NaH (468 mg, 12 mmol) was added DMF (20 mL) under an ice bath, and then was added dropwise a solution of 8-oxabicyclo[3.2.1]octan-3-ol (1.0 g, 7.8 mmol) in DMF (2 mL). The mixture was stirred for 30 min. Then N-(4-(3-chloro-4-fluorophenyl))-7-fluoro-6-nitroquinazolin-4-amine (1.75 g, 5.2 mmol) was added in batch thereto. The mixture was warmed up spontaneously to room temperature and reacted overnight. Water (60 mL-80 mL) was added. The precipitate was formed and filtered by suction to produce a solid, which was dried in vacuum to produce 7-(8-oxabicyclo[3,2,1]octan-3-yloxy)-N-(4-(3-chloro-4-fluorophenyl))-6-nitroquinazolin-4-amine (2.3 g) in a yield of 100%.

(2) Preparation of 7-(8-oxabicyclo[3.2.1]octan-3-yloxy)-N-(4-(3-chloro-4-fluorophenyl))quinazolin-4,6-diamine

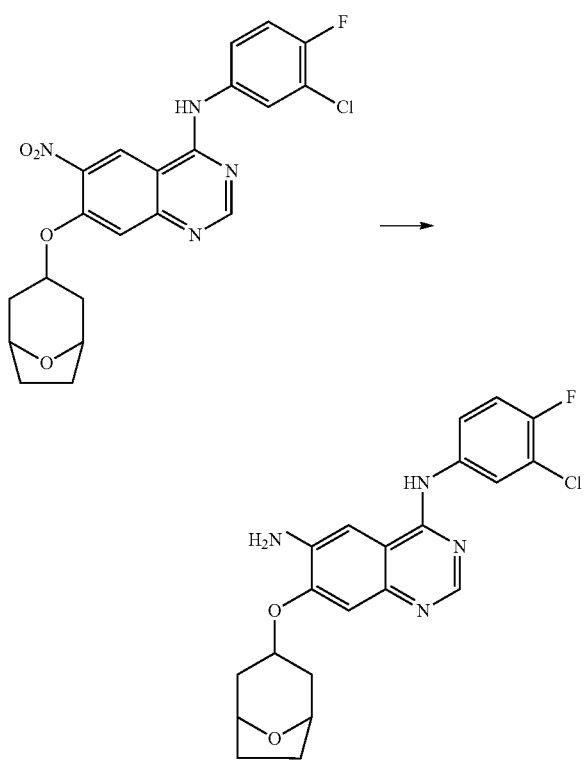

7-(8-oxabicyclo[3.2.1]octan-3-yloxy)-N-(4-(3-chloro-4-fluorophenyl))-6-nitroquinazolin-4-amine (2.3 g, 5.2 mmol) was dissolved in a mixed solution (120 mL) of glacial acetic acid and ethanol (glacial acetic acid/ethanol=1/3). Then Fe powder (2.04 g, 36.4 mmol) was added. The mixture was warmed up spontaneously to room temperature and reacted overnight. The reaction was filtered by suction, and ethanol was removed in vacuum. An appropriate amount of water was added. The mixture was neutralized with a saturated sodium bicarbonate solution until the mixture became neutral. The mixture was extracted with ethyl acetate. The organic layer was concentrated to produce a crude product, which was purified by a silica gel column chromatography (eluted with DCM/methanol=10/1) to produce 7-(8-oxabicyclo[3.2.1]octan-3-yloxy)-N-(4-(3-chloro-4-fluorophenyl))quinazolin-4,6-diamine 500 mg) in a yield of 23%.

(3) Preparation of (E)-N-[7-(8-oxabicyclo[3.2.1]octan-3-yloxy)-4-(3-chloro-4-fluorophenylamino)quinazolin-6-yl]-4-bromo-2-butenamide

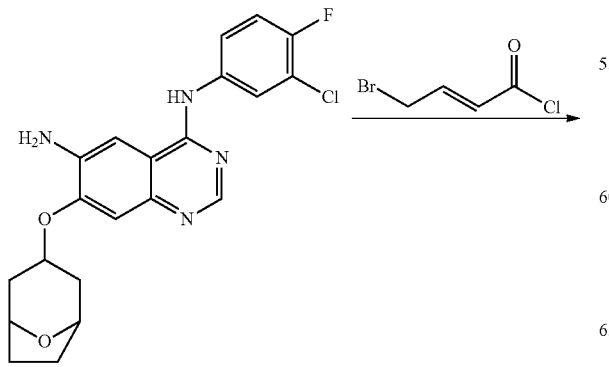

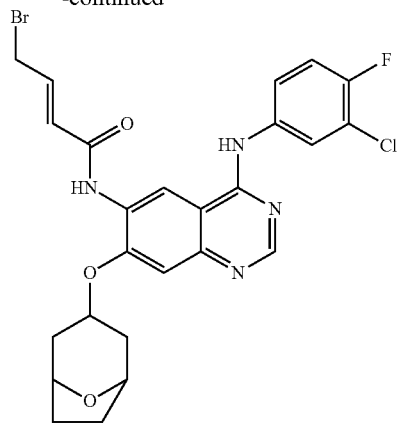

7-(8-oxabicyclo[3.2.1]octan-3-yloxy)-N-(4-(3-chloro-4-fluorophenyl))quinazolin-4,6-diamine (500 mg, 1.2 mmol) was dissolved in dichloromethane (20 mL). To the mixture were successively added triethylamine (976 mg) and 4-bromo-2-butenoyl chloride (275 mg, 1.5 mmol). The mixture was stirred at room temperature for 12 h. An appropriate amount of water was added to the reaction. The reaction was extracted with ethyl acetate. The organic layer was dried over anhydrous sodium sulphate and concentrated to produce a crude product, which was directly used in the next step without purification.

(4) Preparation of (E)-N-[7-(8-oxabicyclo[3.2.1]octan-3-yloxy)-4-(3-chloro-4-fluorophenylamino)quinazolin-6-yl]-4-(piperidin-1-yl)-2-butenamide

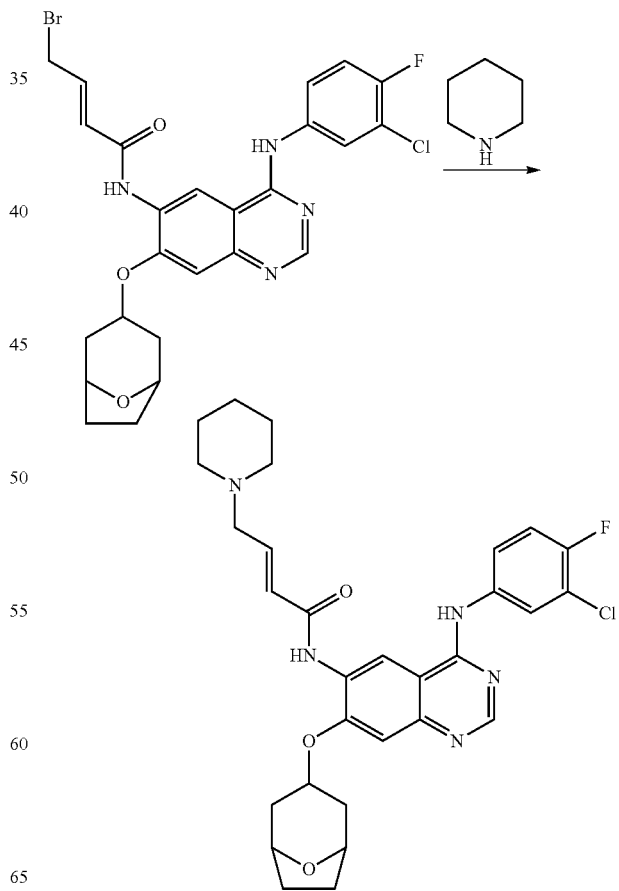

The product from the previous step, (E)-N-[7-(8-oxabicyclo[3.2.1]octan-3-yloxy)-4-(3-chloro-4-fluorophenylamino)quinazolin-6-yl]-4-bromo-2-butenamide was dissolved in acetonitrile (20 mL). Piperidine (205 mg, 2.4 mmol) and cesium carbonate (787 mg, 2.4 mmol) were added. The reaction was conducted at 40° C. for 12 h under stirring. An appropriate amount of water was added to the reaction. The reaction was extracted with dichloromethane. The organic layer was dried over anhydrous sodium sulphate, concentrated, and purified by a silica gel column chromatography (eluted with dichloromethane/methanol=5/1) to produce (E)-N-[7-(8-oxabicyclo[3.2.1]octan-3-yloxy)-4-(3-chloro-4-fluorophenylamino)quinazolin-6-yl]-4-(piperidin-1-yl)-2-butenamide 20 mg) in a yield of 3%.

Molecular formula: $C_{30}H_{33}ClFN_5O_3$

Mass spectrum (m/e): 566.3 (M+1) 283.6 (M/2)

$^1$HNMR: (400 MHz, CDCl$_3$) δ9.13 (s, 1H), 8.67 (s, 1H), 8.10 (s, 1H), 8.00 (d, 1H), 7.54 (m, 2H), 7.18 (t, 1H), 7.07 (m, 1H), 6.22 (d, 1H), 4.98 (m, 1H), 4.60 (m, 2H), 3.25 (m, 2H), 2.51 (m, 4H), 2.23 (m, 4H), 1.88-2.03 (m, 10H).

Example 2 Preparation of (E)-N-[7-(7-oxabicyclo[2.2.1]heptan-2-yloxy)-4-(3-chloro-4-fluorophenylamino)quinazolin-6-yl]-4-(piperidin-1-yl)-2-butenamide (Compound 2)

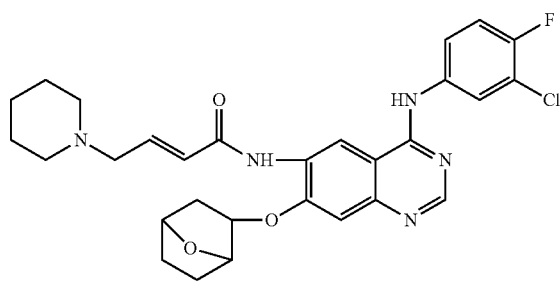 [SMILES: O=C(/C=C/CN1CCCCC1)Nc1cc2c(Nc3ccc(F)c(Cl)c3)ncnc2cc1OC1CC2CCC1O2]

(1) Preparation of 7-(7-oxabicyclo[2.2.1]heptan-2-yloxy)-N-(4-(3-chloro-4-fluorophenyl))-6-nitroquinazolin-4-amine

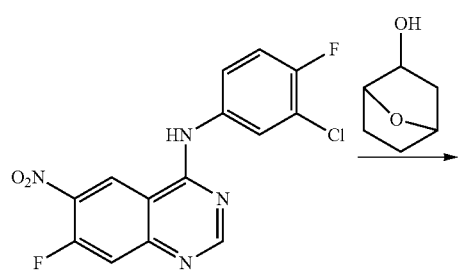

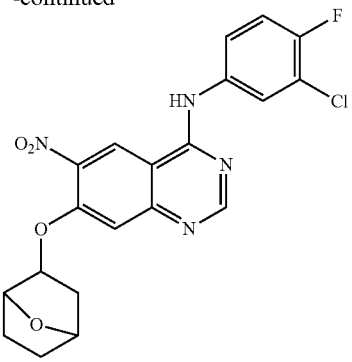

To a round-bottom flask containing NaH (531 mg, 22 mmol) was added DMF (20 mL) under an ice bath, and then was added dropwise a solution of 7-oxabicyclo[2.2.1]heptan-2-ol (1.0 g, 8.8 mmol) in DMF (2 mL). The mixture was stirred for 30 min. Then N-(4-(3-chloro-4-fluorophenyl))-7-fluoro-6-nitroquinazolin-4-amine (1.98 g, 5.9 mmol) was added in batch. The mixture was warmed up spontaneously to room temperature and reacted overnight. Water (60 mL-80 mL) was added. The precipitate was formed and filtered by suction to produce a filtered cake, which was dried in vacuum to produce 7-(7-oxabicyclo[2.2.1]heptan-2-yloxy)-N-(4-(3-chloro-4-fluorophenyl))-6-nitroquinazolin-4-amine (2.5 g) in a yield of 100%.

(2) Preparation of 7-(7-oxabicyclo[2.2.1]heptan-2-yloxy)-N-(4-(3-chloro-4-fluorophenyl))quinazolin-4,6-diamine

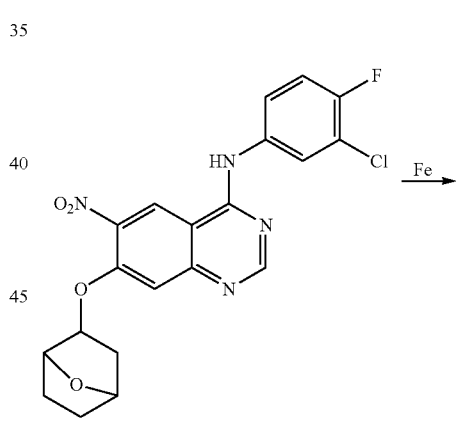

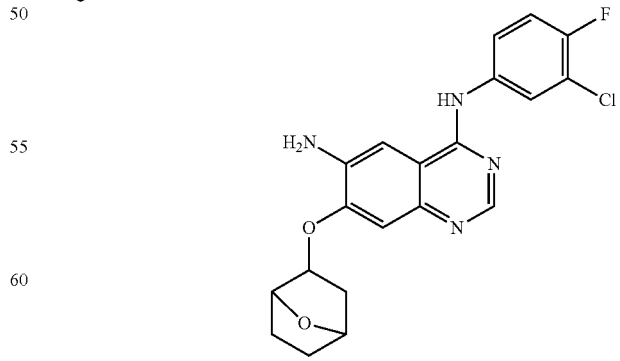

7-(7-oxabicyclo[2.2.1]heptan-2-yloxy)-N-(4-(3-chloro-4-fluorophenyl))-6-nitroquinazolin-4-amine (2.5 g, 5.8 mmol) was dissolved in a mixed solution (120 mL) of glacial acetic acid and ethanol (glacial acetic acid/ethanol=1/3). Then Fe powder (2.28 g, 40.7 mmol) was added. The mixture was warmed up spontaneously to room temperature and reacted overnight. The reaction was filtered by suction, and ethanol was removed in vacuum. An appropriate amount of water was added. The mixture was neutralized with a saturated sodium bicarbonate solution until the mixture became neutral. The mixture was extracted with ethyl acetate. The organic layer was concentrated to produce a crude product, which was purified by a silica gel column chromatography (eluted with DCM/methanol=10/1) to produce 7-(7-oxabicyclo[2.2.1]heptan-2-yloxy)-N-(4-(3-chloro-4-fluorophenyl))quinazolin-4,6-diamine 600 mg) in a yield of 25%.

(3) Preparation of (E)-N-[7-(7-oxabicyclo[2.2.1]heptan-2-yloxy)-4-(3-chloro-4-fluorophenylamino)quinazolin-6-yl]-4-bromo-2-butenamide

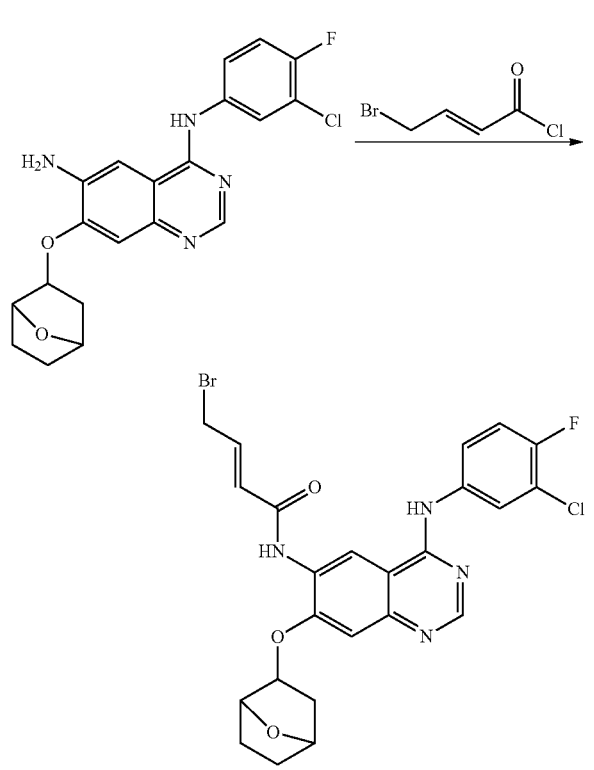

7-(7-oxabicyclo[2.2.1]heptan-2-yloxy)-N-(4-(3-chloro-4-fluorophenyl))quinazolin-4,6-diamine (600 mg, 1.5 mmol) was dissolved in dichloromethane (20 mL). To the mixture were successively added triethylamine (1.21 g) and 4-bromo-2-butenoyl chloride (366 mg, 2.0 mmol). The mixture was stirred at room temperature for 12 h. An appropriate amount of water was added to the reaction. The reaction was extracted with ethyl acetate. The organic layer was dried over anhydrous sodium sulphate and concentrated to produce a crude product, which was directly used in the next step without purification.

(4) Preparation of (E)-N-[7-(7-oxabicyclo[2.2.1]heptan-2-yloxy)-4-(3-chloro-4-fluorophenylamino)quinazolin-6-yl]-4-(piperidin-1-yl)-2-butenamide

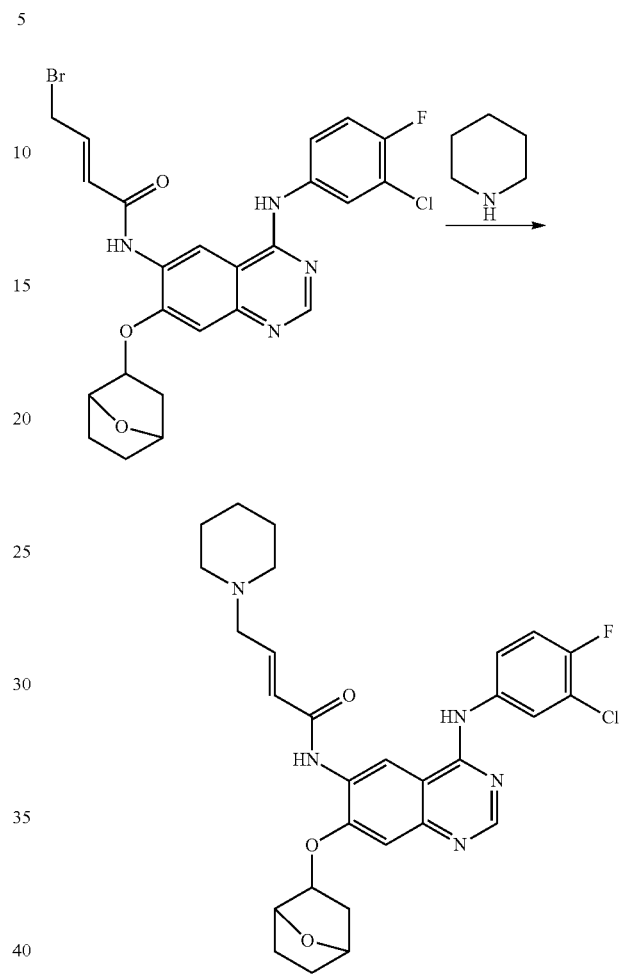

The product from the previous step, (E)-N-[7-(7-oxabicyclo[2.2.1]heptan-2-yloxy)-4-(3-chloro-4-fluorophenylamino)quinazolin-6-yl]-4-bromo-2-butenamide was dissolved in acetonitrile (20 mL). Piperidine (255 mg, 3.0 mmol) and cesium carbonate (978 mg, 3.0 mmol) were added. The reaction was conducted at 40° C. for 12 h under stirring. An appropriate amount of water was added to the reaction. The reaction was extracted with dichloromethane. The organic layer was dried over anhydrous sodium sulphate, concentrated, and purified by a silica gel column chromatography (eluted with dichloromethane/methanol=5/1) to produce (E)-N-[7-(7-oxabicyclo[2.2.1]heptan-2-yloxy)-4-(3-chloro-4-fluorophenylamino)quinazolin-6-yl]-4-(piperidin-1-yl)-2-butenamide (25 mg) in a yield of 3%.

Molecular formula: $C_{29}H_{31}ClFN_5O_3$

Mass spectrum (m/e): 552.2 (M+1)

$^1$HNMR: (400 MHz, CDCl$_3$) δ9.13 (s, 1H), 8.65 (s, 1H), 8.20 (s, 1H), 7.97 (d, 1H), 7.72 (s, 1H), 7.54 (m, 1H), 7.18 (m, 2H), 6.23 (d, 1H), 4.80 (m, 2H), 4.64 (m, 1H), 3.23 (m, 2H), 2.49 (m, 4H), 2.20 (m, 2H), 1.88-2.03 (m, 10H).

Example 3 Preparation of (E)-N-[4-(3-chloro-4-fluorophenylamino)-7-(2-methyl-2,7-diazaspiro[4.5]decan-7-yl)quinazolin-6-yl]-4-(piperidin-1-yl)-2-butenamide (Compound 3)

(2) Preparation of N-(4-(3-chloro-4-fluorophenyl))-7-(2-methyl-2,7-diazaspiro[4.5]decan-7-yl)quinazolin-4,6-diamine

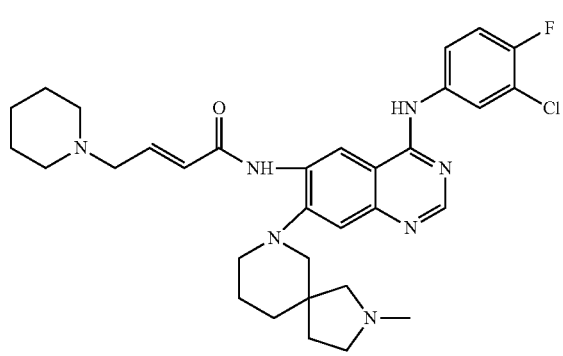 [SMILES: CN1CCC2(CCCN(c3cc4ncnc(Nc5ccc(F)c(Cl)c5)c4cc3NC(=O)/C=C/CN3CCCCC3)C2)C1]

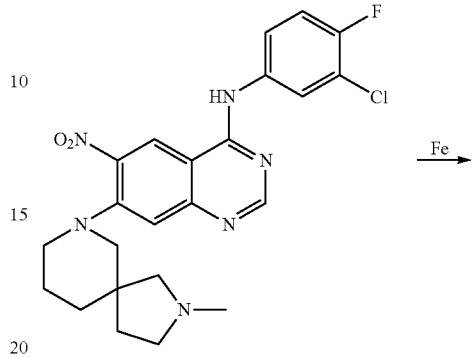

(1) Preparation of N-(4-(3-chloro-4-fluorophenyl))-7-(2-methyl-2,7-diazaspiro[4.5]decan-7-yl)-6-nitro-quinazolin-4-amine

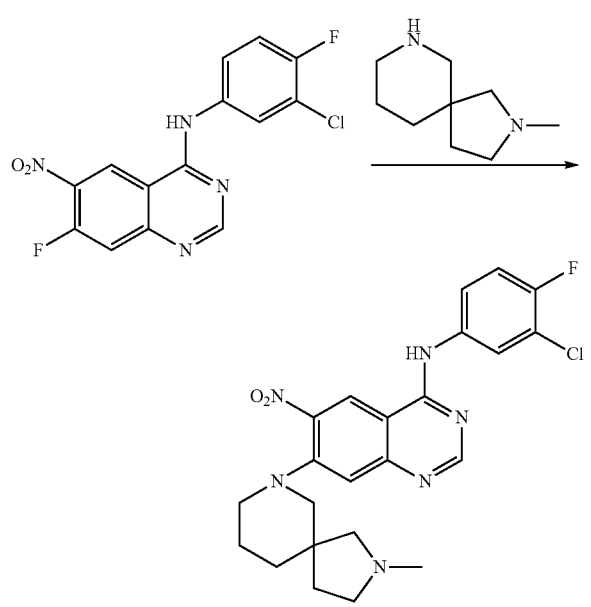

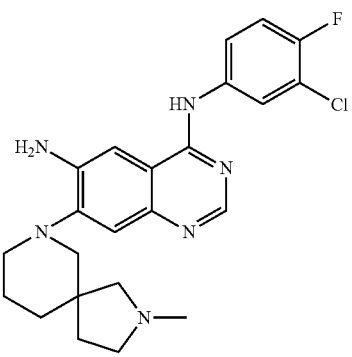

N-(4-(3-chloro-4-fluorophenyl))-7-(2-methyl-2,7-diazaspiro[4.5]decan-7-yl)-6-nitroquinazolin-4-amine (600 mg, 1.3 mmol) was dissolved in ethanol (9 mL) and acetic acid (3 mL). The mixture was added to 80° C. and reacted for 2 h. After the completion of reaction, the solvent was evaporated off, and the residual material was extracted with ethyl acetate. The extracted liquid was dried over anhydrous sodium sulphate and concentrated to dryness to produce N-(4-(3-chloro-4-fluorophenyl))-7-(2-methyl-2,7-diazaspiro[4,5]decan-7-yl)quinazolin-4,6-diamine (500 mg) in a yield of 87%.

(3) Preparation of (E)-N-[4-(3-chloro-4-fluorophenylamino)-7-(2-methyl-2,7-diazaspiro[4.5]decan-7-yl)quinazolin-6-yl]-4-bromo-2-butenamide

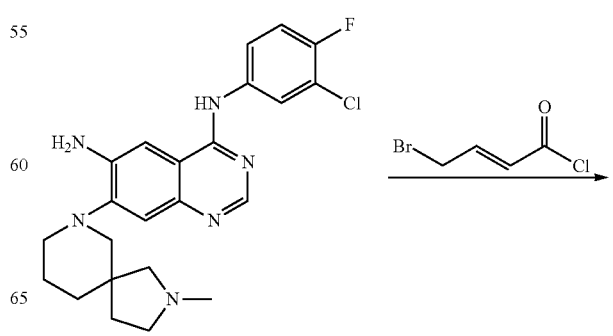

2-methyl-2,7-diazaspiro[4.5]decane (500 mg, 3.2 mmol), potassium carbonate (1.0 g, 7.2 mmol) and N-(4-(3-chloro-4-fluorophenyl))-7-fluoro-6-nitroquinazolin-4-amine (560 mg, 1.7 mmol) were dissolved in acetonitrile (20 mL). The mixture was added to 82° C. and reacted for 4 h. The reaction was cooled to room temperature. Water (30 mL) was added. The reaction was extracted with ethyl acetate. The organic layer was dried over anhydrous sodium sulphate, filtered, and concentrated. The concentrate was purified by a silica gel column chromatography (eluted with dichloromethane/methanol=40/1) to produce N-(4-(3-chloro-4-fluorophenyl))-7-(2-methyl-2,7-diazaspiro[4.5]decan-7-yl)-6-nitroquinazolin-4-amine (600 mg) in a yield of 75%.

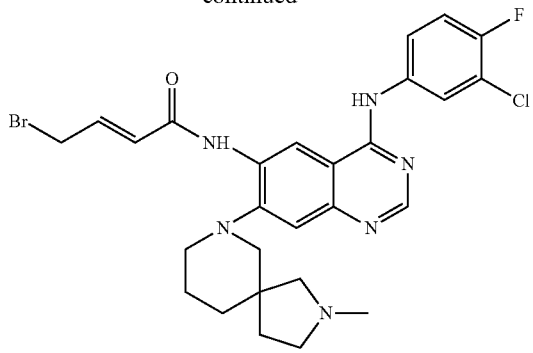

N-(4-(3-chloro-4-fluorophenyl))-7-(2-methyl-2,7-diazaspiro[4.5]decan-7-yl)quinazolin-4,6-diamine (500 mg, 1.1 mmol) and (E)-4-bromo-2-butenoyl chloride (1.1 g, 6 mmol) was dissolved in THF (20 mL). To the mixture was successively added DIPEA (2 mL). The mixture was stirred at room temperature for 1 h. To the solution was added water (30 mL). The solution was extracted with ethyl acetate. The organic layers were combined and dried over anhydrous sodium sulphate, and evaporated to dryness. The resulting solid was purified by a silica gel column chromatography (eluted with dichloromethane/methanol=60/1) to produce (E)-N-[4-(3-chloro-4-fluorophenylamino)-7-(2-methyl-2,7-diazaspiro[4.5]decan-7-yl)quinazolin-6-yl]-4-bromo-2-butenamide (230 mg) in a yield of 36%.

(4) Preparation of (E)-N-[4-(3-chloro-4-fluorophenylamino)-7-(2-methyl-2,7-diazaspiro[4.5]decan-7-yl)quinazolin-6-yl]-4-(piperidin-1-yl)-2-butenamide

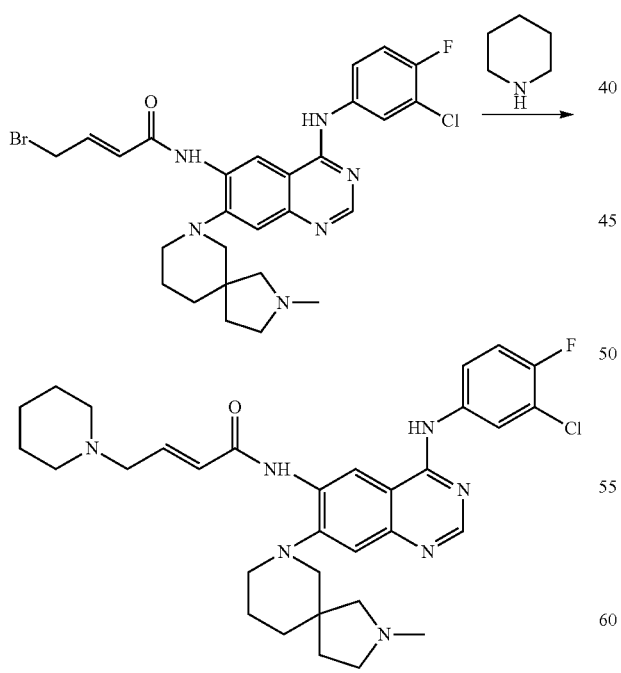

(E)-N-[4-(3-chloro-4-fluorophenylamino)-7-(2-methyl-2,7-diazaspiro[4.5]decan-7-yl)quinazolin-6-yl]-4-bromo-2-butenamide (240 mg, 0.4 mmol), piperidine (70 mg, 0.8 mmol) and potassium carbonate (110 mg, 0.8 mmol) were dissolved in acetonitrile (20 mL). The mixture was reacted at 50° C. for 8 h. After the completion of reaction, to the reaction mixture was added an appropriate amount of water. The reaction was extracted with ethyl acetate. The organic layer was dried over anhydrous sodium sulphate and filtered. The filtrate was concentrated. The concentrate was purified by a silica gel column chromatography (eluted with dichloromethane/methanol=15/1) to produce (E)-N-[4-(3-chloro-4-fluorophenylamino)-7-(2-methyl-2,7-diazaspiro[4.5]decan-7-yl)quinazolin-6-yl]-4-(piperidin-1-yl)-2-butenamide (18 mg) in a yield of 8%.

Molecular formula: $C_{32}H_{39}ClFN_7O$

Mass spectrum (m/e): 592.3 (M+1), 296.6 (M/2)

$^1$HNMR: (400 MHz, CDCl$_3$) δ9.00 (s, 1H), 8.74 (s, 1H), 8.65 (s, 1H), 8.06 (s, 1H), 7.99 (d, 1H), 7.58 (s, 1H), 7.58 (s, 1H), 7.08 (m, 2H), 6.16 (d, 1H), 3.21 (d, 2H), 2.90-3.20 (m, 7H), 2.46-2.78 (m, 5H), 2.38 (s, 3H), 1.28-1.79 (m, 12H).

Example 4 Preparation of N-[4-(3-chloro-4-fluorophenylamino)-7-(8-methyl-8-azabicyclo[3.2.1]octan-3-yloxy)quinazolin-6-yl]-acrylamide (Compound 4)

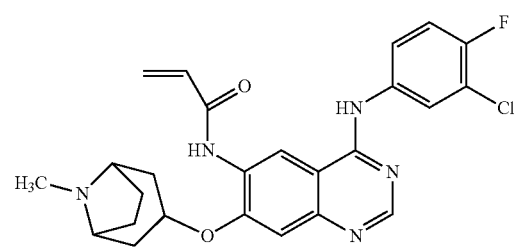 [SMILES: C=CC(=O)Nc1cc2c(Nc3ccc(F)c(Cl)c3)ncnc2cc1OC1CC2CCC(C1)N2C]

(1) Preparation of N-(4-(3-chloro-4-fluorophenyl))-7-(8-methyl-8-azabicyclo[3.2.1]octan-3-yloxy)-6-nitroquinazolin-4-amine

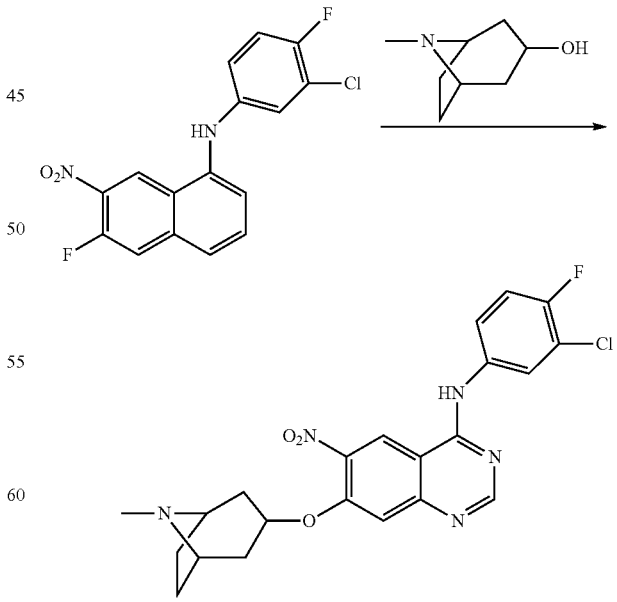

8-methyl-8-azabicyclo[3.2.1]octan-3-ol (0.7 g, 5 mmol) was dissolved in DMF (20 mL). 60% sodium hydride (0.4 g, 10 mmol) was added in batch in an ice bath under an atmosphere of N₂. The mixture was moved to an atmosphere of room temperature and stirred for 1 h. N-(4-(3-chloro-4-fluorophenyl))-7-fluoro-6-nitroquinazolin-4-amine (1.12 g, 3.3 mmol) was added. The mixture was stirred at 50° C. overnight. After the completion of reaction, water (50 mL) was added. The mixture was extracted with EA. The organic layer was rotary-evaporated to dryness under a reduced pressure to produce N-(4-(3-chloro-4-fluorophenyl))-7-(8-methyl-8-azabicyclo[3.2.1]octan-3-yloxy)-6-nitroquinazolin-4-amine (560 mg) in a yield of 37%.

(2) Preparation of N-(4-(3-chloro-4-fluorophenyl))-7-(8-methyl-8-azabicyclo[3.2.1]octan-3-yloxy)quinazolin-4,6-diamine

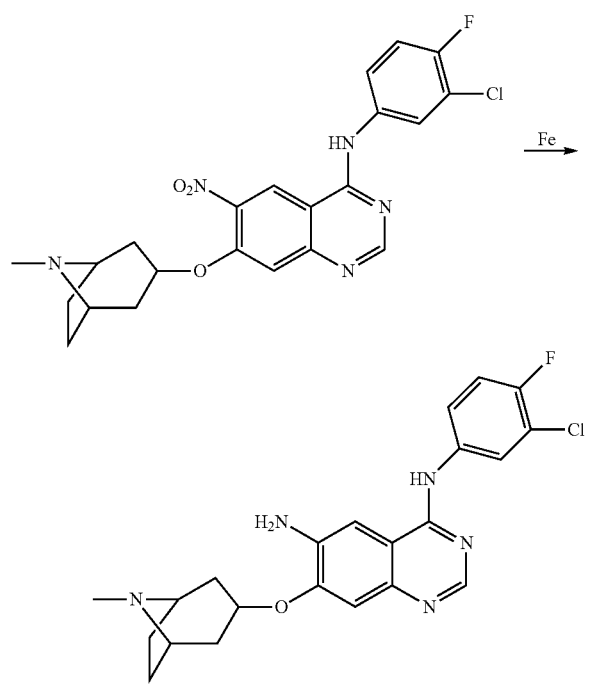

N-(4-(3-chloro-4-fluorophenyl))-7-(8-methyl-8-azabicyclo[3.2.1]octan-3-yloxy)-6-nitroquinazolin-4-amine (560 mg, 1.22 mmol) was dissolved in a mixed solvent (20 mL) of acetic acid and ethanol (CH₃COOH/EtOH=1/3). Then Fe powder (343 mg, 6.12 mmol) was added. The mixture was warmed up to 70° C. and stirred for 1 h. After the completion of reaction, the mixture was rotary-evaporated under a reduced pressure to remove EtOH. Water (30 mL) was added. The mixture was extracted with EA, and adjusted with 1 mol/L NaOH solution until the mixture became basic. The mixture was extracted with EA. The organic layer was rotary-evaporated to dryness under a reduced pressure to produce N-(4-(3-chloro-4-fluorophenyl))-7-(8-methyl-8-azabicyclo[3.2.1]octan-3-yloxy)quinazolin-4,6-diamine (360 mg) in a yield of 69%.

(3) Preparation of N-[4-(3-chloro-4-fluorophenylamino)-7-(8-methyl-8-azabicyclo[3.2.1]octan-3-yloxy)quinazolin-6-yl]-acrylamide

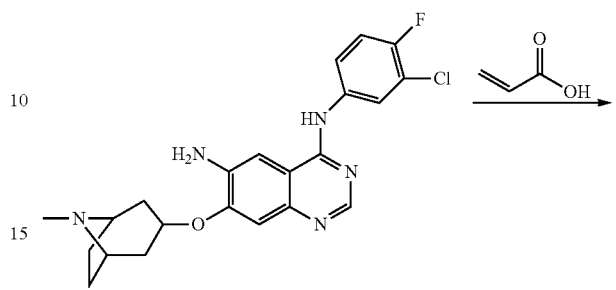

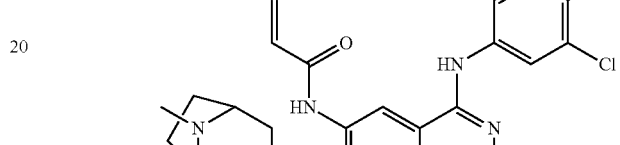

Acrylic acid (243 mg, 3.37 mmol) was dissolved in DMF (10 mL). To the resulting mixture was added DMAP (162 mg, 1.35 mmol), N-(4-(3-chloro-4-fluorophenyl))-7-(8-methyl-8-azabicyclo[3.2.1]octan-3-yloxy)quinazolin-4,6-diamine (360 mg, 0.84 mmol) and EDC (193 mg, 1.01 mmol) under an ice bath. The mixture was stirred at room temperature overnight. After the completion of reaction, water (50 mL) was added. The mixture was extracted with EA. The organic layer was rotary-evaporated to dryness under a reduced pressure. The residue was washed with diethyl ether to produce N-[4-(3-chloro-4-fluorophenylamino)-7-(8-methyl-8-azabicyclo[3.2.1]octan-3-yloxy)quinazolin-6-yl]-acrylamide (54 mg) in a yield of 13%.

Molecular formula: $C_{25}H_{25}ClFN_5O_2$

Mass spectrum (m/e): 482.2 (M+1), 241.6 (M/2)

¹HNMR: (400 MHz, DMSO-$d_6$) δ9.78 (s, 1H), 9.55 (s, 1H), 8.72 (s, 1H), 8.52 (s, 1H), 8.14 (d, 1H), 7.80 (d, 1H), 7.41 (t, 1H), 7.11 (s, 1H), 6.58 (m, 1H), 6.30 (d, 1H), 5.80 (d, 1H), 4.83 (m, 1H), 3.03 (m, 2H), 2.12 (s, 3H), 2.10 (m, 2H), 1.88 (m, 6H).

Example 5 Preparation of N-[4-(3-chloro-4-fluorophenylamino)-7-(8-methyl-1-oxa-8-azaspiro[4.5]decan-3-yloxy)quinazolin-6-yl]-acrylamide (Compound 5)

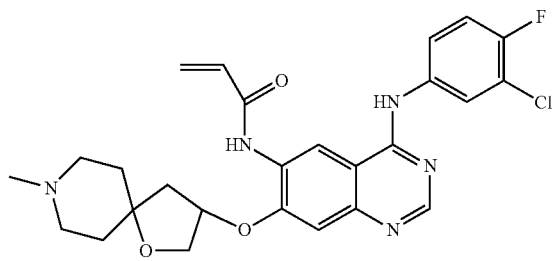 [SMILES: C=CC(=O)Nc1cc2c(Nc3ccc(F)c(Cl)c3)ncnc2cc1OC1COC2(CCN(C)CC2)C1]

(1) Preparation of N-(4-(3-chloro-4-fluorophenyl))-7-(8-methyl-1-oxa-8-azaspiro[4.5]decan-3-yloxy)-6-nitroquinazolin-4-amine

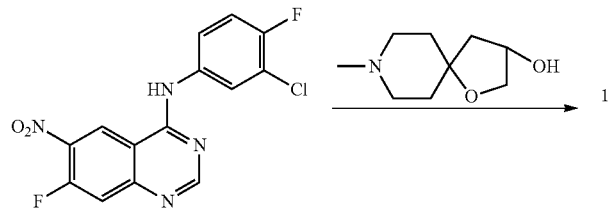

8-methyl-1-oxa-8-azaspiro[4.5]decan-3-ol (0.4 g, 2.5 mmol) was dissolved in DMF (60 mL). 60% sodium hydride (0.4 g, 10 mmol) was added in batch in an ice bath under an atmosphere of $N_2$. The mixture was moved to an atmosphere of room temperature and stirred for 1 h. N-(4-(3-chloro-4-fluorophenyl))-7-fluoro-6-nitroquinazolin-4-amine (1.12 g, 3.3 mmol) was added. The mixture was stirred at 50° C. overnight. After the completion of reaction, water (50 mL) was added. The mixture was extracted with EA. The organic layer was rotary-evaporated to dryness under a reduced pressure to produce N-(4-(3-chloro-4-fluorophenyl))-7-(8-methyl-1-oxa-8-azaspiro[4.5]decan-3-yloxy)-6-nitroquinazolin-4-amine (1.0 g) in a yield of 82%.

(2) Preparation of N-(4-(3-chloro-4-fluorophenyl))-7-(8-methyl-1-oxa-8-azaspiro[4.5]decan-3-yloxy)quinazolin-4,6-diamine

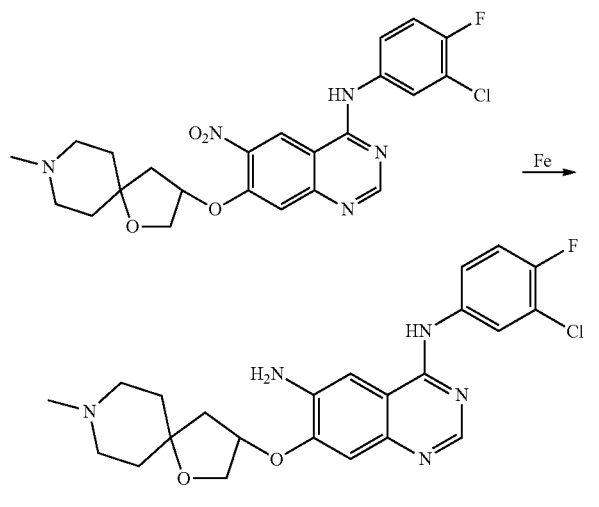

N-(4-(3-chloro-4-fluorophenyl))-7-(8-methyl-1-oxa-8-azaspiro[4.5]decan-3-yloxy)-6-nitroquinazolin-4-amine (1.0 g, 2.05 mmol) was dissolved in a mixed solvent (80 mL) of acetic acid and ethanol ($CH_3COOH/EtOH=1/3$). To the mixture was added Fe powder (1.5 g, 26 mmol). The mixture was warm up to 70° C. and stirred for 1 h. After the completion of reaction, the mixture was rotary-evaporated under a reduced pressure to remove EtOH. Water (30 mL) was added. The mixture was adjusted with 1 mol/L NaOH solution until it became basic. The mixture was extracted with EA. The organic layer was rotary-evaporated to dryness under a reduced pressure to produce N-(4-(3-chloro-4-fluorophenyl))-7-(8-methyl-1-oxa-8-azaspiro[4.5]decan-3-yloxy)quinazolin-4,6-diamine (400 mg) in a yield of 43%.

(3) Preparation of N-[4-(3-chloro-4-fluorophenylamino)-7-(8-methyl-1-oxa-8-azaspiro[4.5]decan-3-yloxy)quinazolin-6-yl]-acrylamide

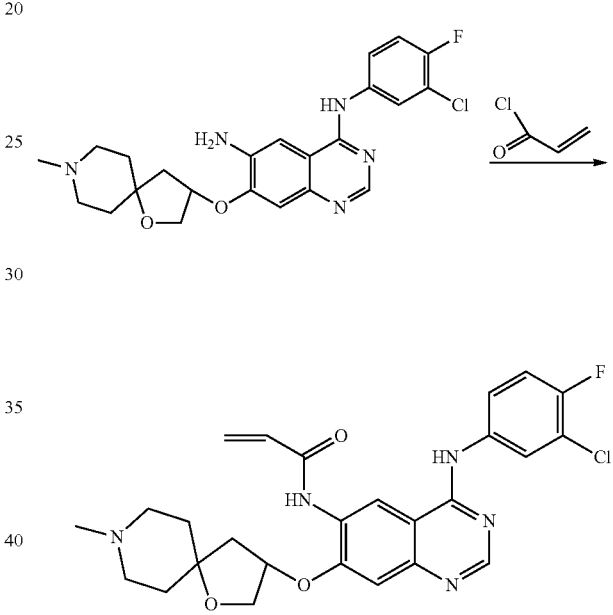

N-(4-(3-chloro-4-fluorophenyl))-7-(8-methyl-1-oxa-8-azaspiro[4.5]decan-3-yloxy)quinazolin-4,6-diamine (400 mg, 0.9 mmol) was dissolved in DCM (20 mL). To the resulting mixture were added triethylamine (0.3 mL) and acryloyl chloride (81 mg, 0.9 mmol). The mixture was stirred at room temperature for 30 min. After the completion of reaction, water (50 mL) was added. The mixture was extracted with EA. The organic layer was rotary-evaporated to dryness under a reduced pressure. The residue was purified by a silica gel column chromatography (eluted with dichloromethane/methanol=5/1) to produce N-[4-(3-chloro-4-fluorophenylamino)-7-(8-methyl-1-oxa-8-azaspiro[4.5]decan-3-yloxy)quinazolin-6-yl]-acrylamide (100 mg) in a yield of 22%.

Molecular formula: $C_{26}H_{27}ClFN_5O_3$

Mass spectrum (m/e): 512.2 (M+1), 256.6 (M/2)

$^1$HNMR: (400 MHz, $CDCl_3$) δ9.15 (s, 1H), 8.64 (s, 1H), 7.98 (s, 1H), 7.96 (d, 1H), 7.55 (m, 2H), 7.16 (t, 1H), 7.12 (s, 1H), 6.50 (d, 1H), 6.35 (m, 1H), 5.92 (d, 1H), 5.20 (m, 1H), 4.23 (m, 2H), 3.07 (m, 1H), 2.96 (m, 2H), 2.64 (s, 3H), 2.38 (m, 4H), 2.04 (d, 1H), 1.84 (d, 1H), 1.44 (t, 1H).

Example 6 Preparation of N-[4-(3-chloro-4-fluorophenylamino)-7-((8-methyl-1-oxa-8-azaspiro[4.5]decan-3-yl)methoxy)quinazolin-6-yl]-acrylamide (Compound 6)

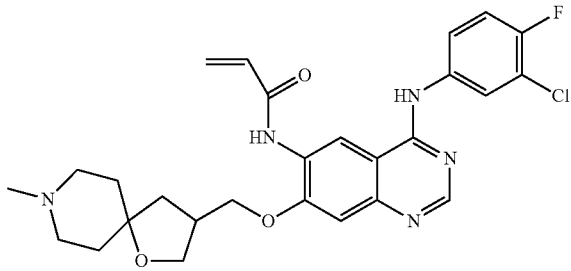 [SMILES: C=CC(=O)Nc1cc2c(Nc3ccc(F)c(Cl)c3)ncnc2cc1OCC1COC2(CCN(C)CC2)C1]

(1) Preparation of N-(4-(3-chloro-4-fluorophenyl))-7-((8-methyl-1-oxa-8-azaspiro[4.5]decan-3-yl)methoxy)-6-nitroquinazolin-4-amine

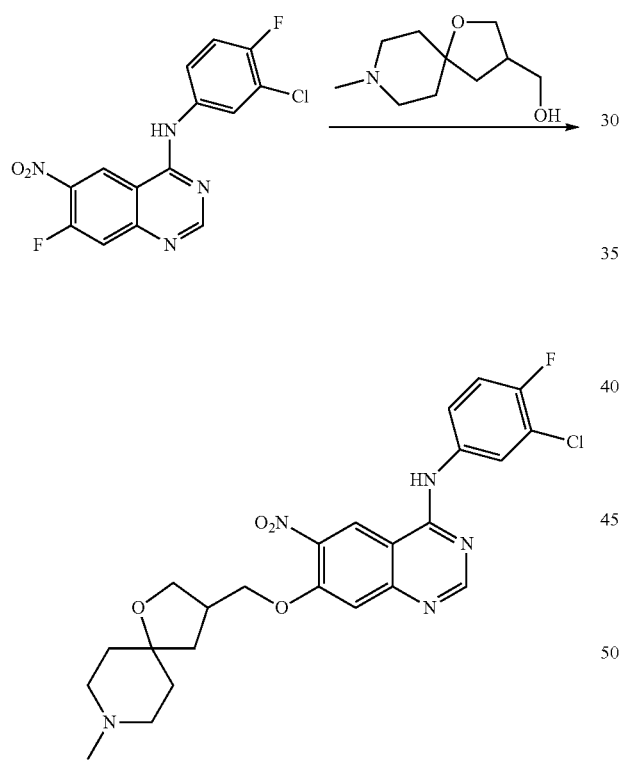

(8-methyl-1-oxa-8-azaspiro[4.5]decan-3-yl)methanol (300 mg, 1.08 mmol) was dissolved in DMF (20 mL). 60% sodium hydride (97 mg, 2.43 mmol) was added in batch in an ice bath under an atmosphere of N2. The mixture was moved to an atmosphere of room temperature and stirred for 1 h. N-(4-(3-chloro-4-fluorophenyl))-7-fluoro-6-nitroquinazolin-4-amine (362 mg, 1.08 mmol) was added. The mixture was stirred at 50° C. overnight. After the completion of reaction, a large quantity of water was added. The mixture was filtered, and the filtered cake was dried in vacuum to produce N-(4-(3-chloro-4-fluorophenyl))-7-((8-methyl-1-oxa-8-azaspiro[4.5]decan-3-yl)methoxy)-6-nitroquinazolin-4-amine (516 mg) in a yield of 95%.

(2) Preparation of N-(4-(3-chloro-4-fluorophenyl))-7-((8-methyl-1-oxa-8-azaspiro[4.5]decan-3-yl)methoxy)quinazolin-4,6-diamine

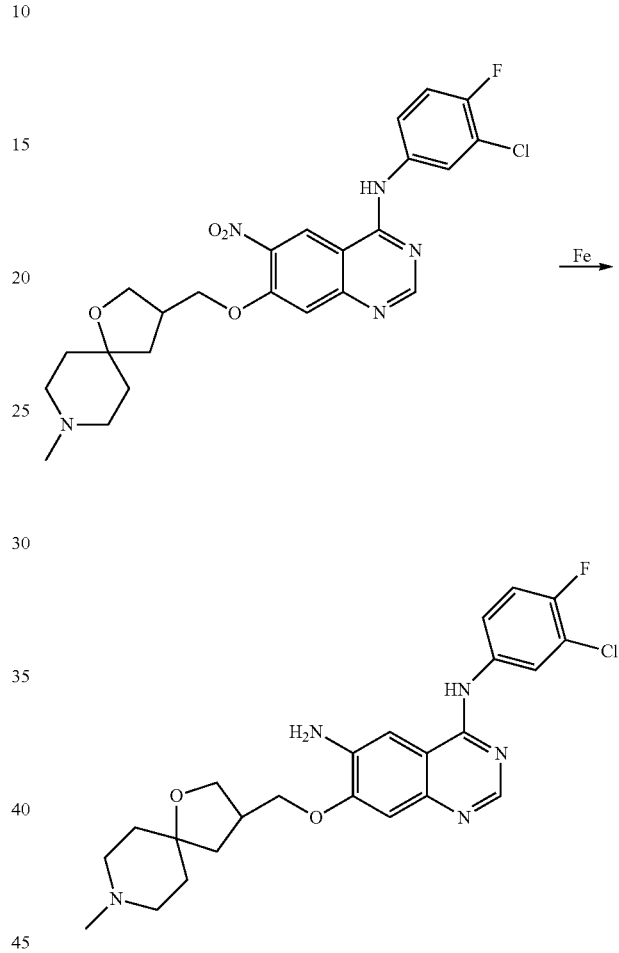

N-(4-(3-chloro-4-fluorophenyl))-7-((8-methyl-1-oxa-8-azaspiro[4.5]decan-3-yl)methoxy)-6-nitroquinazolin-4-amine (516 mg, 1.03 mmol) was dissolved in a mixed solvent (60 mL) of acetic acid and ethanol ($CH_3COOH/EtOH=1/3$). To the mixture was added Fe powder (346 mg, 6.18 mmol). The mixture was stirred at room temperature for 12 h. After the completion of reaction, the mixture was rotary-evaporated under a reduced pressure to remove EtOH. Water (30 mL) was added. The mixture was adjusted with 1 mol/L NaOH solution until it became basic. The mixture was extracted with EA. The organic layer was concentrated, and the resulting residue was purified by a silica gel column chromatography (eluted with dichloromethane/methanol=10/1) to produce N-(4-(3-chloro-4-fluorophenyl))-7-((8-methyl-1-oxa-8-azaspiro[4.5]decan-3-yl)methoxy)quinazolin-4,6-diamine (100 mg) in a yield of 21%.

(3) Preparation of N-[4-(3-chloro-4-fluorophenylamino)-7-((8-methyl-1-oxa-8-azaspiro[4.5]decan-3-yl)meth oxy)quinazolin-6-yl]-acrylamide

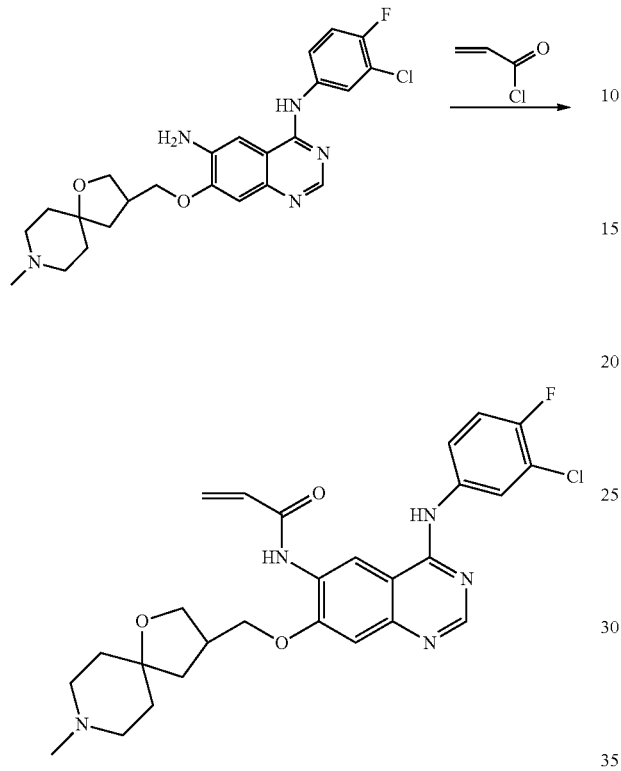

In a reaction flask, N-(4-(3-chloro-4-fluorophenyl))-7-((8-methyl-1-oxa-8-azaspiro[4.5]decan-3-yl)methoxy)quinazolin-4,6-diamine (100 mg, 0.21 mmol) was dissolved in dichloromethane (10 mL). The mixture was cooled down to 0° C. Triethylamine (42 mg, 0.42 mmol) was added to the reaction flask. Acryloyl chloride (17 mg, 0.19 mmol) was dissolved in DCM (1 mL). The resulting solution was slowly added to the reaction flask. The mixture was reacted at room temperature for 30 min. The reaction was washed with distilled water (10 mL) triple, and distillated at a reduced pressure to remove dichloromethane to produce a crude yellow powdery product, which was purified by a silica gel column chromatography (eluted with DCM/MeOH=15/1) to produce a pale-yellow powdery solid N-[4-(3-chloro-4-fluorophenylamino)-7-((8-methyl-1-oxa-8-azaspiro[4.5]decan-3-yl)meth oxy)quinazolin-6-yl]-acrylamide (15 mg) in a yield of 14%.

Molecular formula: $C_{27}H_{29}ClFN_5O_3$

Mass spectrum (m/e): 526.2 (M+1), 263.6 (M/2)

$^1$HNMR: (400 MHz, CDCl$_3$) δ9.10 (s, 1H), 8.63 (s, 1H), 8.32 (s, 1H), 7.86 (d, 1H), 7.74 (s, 1H), 7.48 (d, 1H), 7.15 (s, 1H), 7.10 (m, 1H), 6.48 (d, 1H), 6.38 (m, 1H), 5.86 (d, 1H), 4.18 (t, 2H), 4.08 (t, 1H), 3.87 (t, 1H), 2.91 (s, H), 2.60 (m, 4H), 2.36 (m, 3H), 2.13 (t, 1H), 1.80-2.11 (m, 4H), 1.60 (m, 1H).

Example 7 Preparation of N-[4-(3-chloro-4-fluorophenylamino)-7-(8-methyl-1-oxa-8-azaspiro[4.5]decan-2-ylmethoxy)quinazolin-6-yl]-acrylamide (Compound 7)

(1) Preparation of N-(4-(3-chloro-4-fluorophenyl))-7-(8-methyl-1-oxa-8-azaspiro[4.5]decan-2-ylmethoxy)-6-nitroquinazolin-4-amine

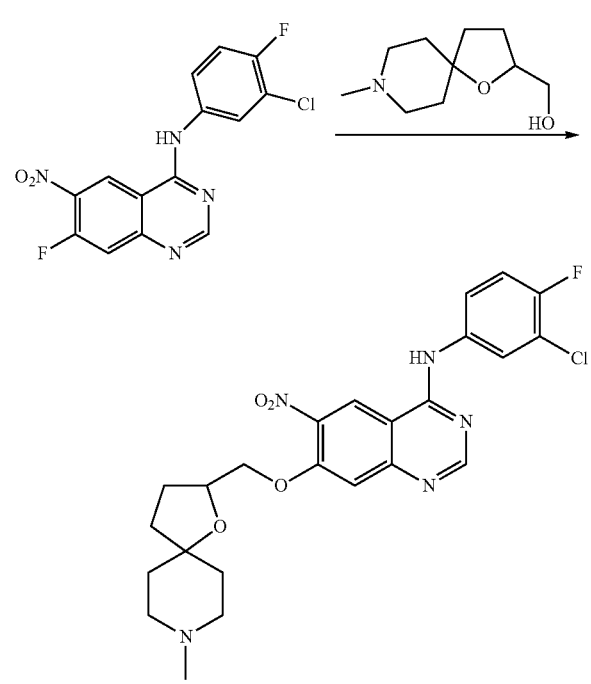

8-methyl-1-oxa-8-azaspiro[4.5]decan-2-ylmethanol (280 mg, 1.5 mmol) was dissolved in DMF (20 mL). 60% sodium hydride (1.1 g, 27 mmol) was added in batch in an ice bath under an atmosphere of N$_2$. The mixture was moved to an atmosphere of room temperature and stirred for 1 h. N-(4-(3-chloro-4-fluorophenyl))-7-fluoro-6-nitroquinazolin-4-amine (508 mg, 1.5 mmol) was added. The mixture was stirred at 50° C. overnight. After the completion of reaction, water (50 mL) was added. The mixture was extracted with EA. The organic layer was rotary-evaporated to dryness under a reduced pressure to produce N-(4-(3-chloro-4-fluorophenyl))-7-(8-methyl-1-oxa-8-azaspiro[4.5]decan-2-ylmethoxy)-6-nitroquinazolin-4-amine (380 mg) in a yield of 50%.

(2) Preparation of N-(4-(3-chloro-4-fluorophenyl))-7-(8-methyl-1-oxa-8-azaspiro[4.5]decan-2-ylmethoxy)quinazolin-4,6-diamine

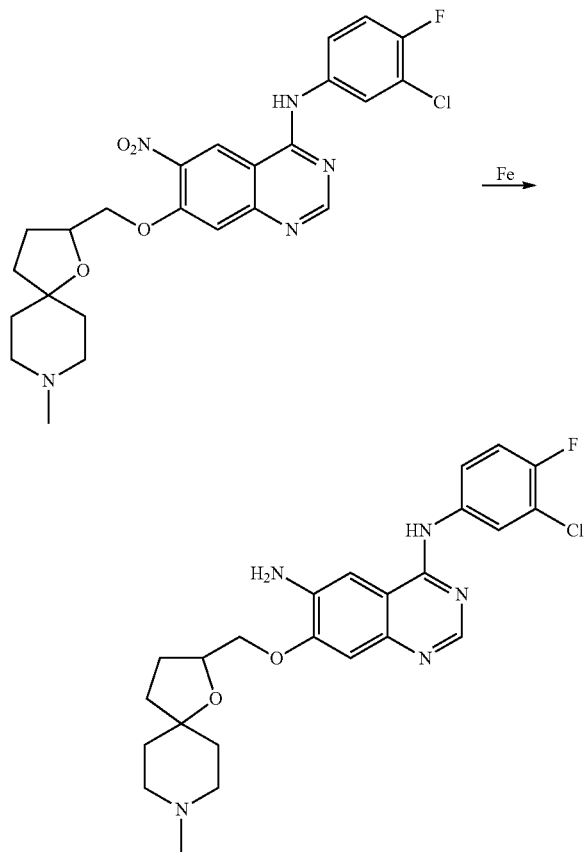

N-(4-(3-chloro-4-fluorophenyl))-7-8-methyl-1-oxa-8-azaspiro[4.5]decan-2-ylmethoxy)-6-nitroquinazolin-4-amine (380 mg, 0.76 mmol) was dissolved in a mixed solvent (8 mL) of acetic acid and ethanol (CH$_3$COOH/EtOH=1/3). To the mixture was added Fe powder (343 mg, 6.12 mmol). The mixture was warm up to 70° C. and stirred for 1 h. After the completion of reaction, the mixture was rotary-evaporated under a reduced pressure to remove EtOH. Water (30 mL) was added. The mixture was adjusted with 1 mol/L NaOH solution until it became basic. The mixture was extracted with EA. The organic layer was rotary-evaporated to dryness under a reduce pressure. The resulting residue was purified by a silica gel column chromatography (eluted with dichloromethane/methanol=15/1) to produce N-(4-(3-chloro-4-fluorophenyl))-7-(8-methyl-1-oxa-8-azaspiro[4.5]decan-2-ylmethoxy)quinazolin-4,6-diamine (180 mg) in a yield of 50%.

(3) Preparation of N-[4-(3-chloro-4-fluorophenylamino)-7-(8-methyl-1-oxa-8-azaspiro[4.5]decan-2-ylmethoxy)quinazolin-6-yl]-acrylamide

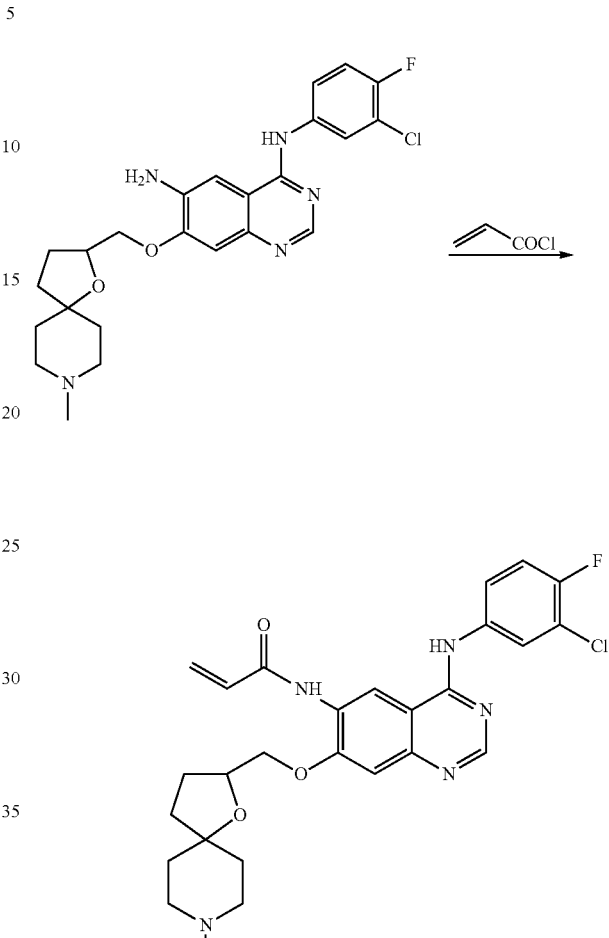

N-(4-(3-chloro-4-fluorophenyl))-7-(8-methyl-1-oxa-8-azaspiro[4.5]decan-2-ylmethoxy)quinazolin-4,6-diamine (175 mg, 0.38 mmol) was dissolved in dichloromethane (30 mL). Triethylamine (77 mg) was added. Acryloyl chloride (31 mg, 0.34 mmol) was added dropwise under an ice bath. The mixture was stirred at room temperature for 0.5 h. After the completion of reaction, water (50 mL) was added. The mixture was extracted with EA. The organic layer was rotary-evaporated to dryness under a reduced pressure. The resulting residue was purified by a silica gel column chromatography (eluted with dichloromethane/methanol=20/1) to produce N-[4-(3-chloro-4-fluorophenylamino)-7-(8-methyl-1-oxa-8-azaspiro[4.5]decan-2-ylmethoxy)quinazolin-6-yl]-acrylamide (14 mg) in a yield of 8%.

Molecular formula: $C_{27}H_{29}ClFN_5O_3$

Mass spectrum (m/e): 526.2 (M+1), 263.7 (M/2)

$^1$HNMR (400 MHz, CDCl$_3$) δ8.92 (s, 1H), 8.55 (s, 1H), 7.98 (d, 1H), 7.62 (d, 1H), 7.20 (s, 1H), 7.13 (t, 1H), 6.47 (d, 2H), 5.86 (d, 1H), 4.47 (m, 1H), 4.24 (d, 1H), 4.10 (t, 1H), 3.05 (m, 4H), 2.49 (s, 3H), 1.78-1.97 (m, 8H).

Example 8 Preparation of N-[4-(3-chloro-4-fluorophenylamino)-7-(2-((1R,5S,6S)-3-methyl-3-azabicyclo[3.1.0]hexan-6-ylethoxy)quinazolin-6-yl]-acrylamide (Compound 8)

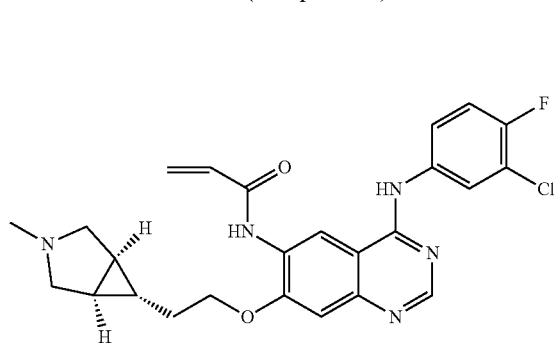

(1) Preparation of N-(4-(3-chloro-4-fluorophenyl))-7-(2-((1R,5S,6S)-3-methyl-3-azabicyclo[3.1.0]hexan-6-ylethoxy)-6-nitroquinazolin-4-amine

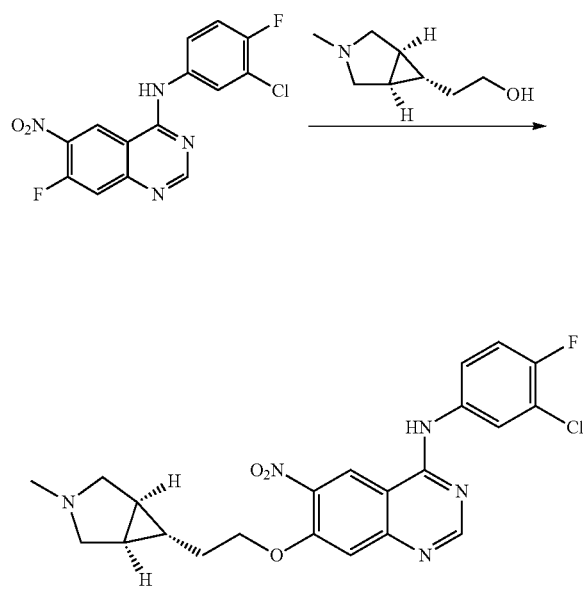

2-((1R,5S,6S)-3-methyl-3-azabicyclo[3.1.0]hexan-6-ylethanol (0.2 g, 1.4 mmol) was dissolved DMF (10 mL). 60% sodium hydride (1.12 g, 2.8 mmol) was added in batch in an ice bath under an atmosphere of N₂. The mixture was moved to an atmosphere of room temperature and stirred for 30 min. N-(4-(3-chloro-4-fluorophenyl))-7-fluoro-6-nitroquinazolin-4-amine (470 mg, 1.4 mmol) was added. The mixture was stirred at 50° C. overnight. After the completion of reaction, water (50 mL) was added. The mixture was extracted with EA. The organic layer was rotary-evaporated to dryness under a reduced pressure to produce N-(4-(3-chloro-4-fluorophenyl))-7-2-((1R,5S,6S)-3-methyl-3-azabicyclo[3.1.0]hexan-6-yl ethoxy)-6-nitroquinazolin-4-amine (500 mg) in a yield of 78%.

(2) Preparation of N-(4-(3-chloro-4-fluorophenyl))-7-(2-((1R,5S,6S)-3-methyl-3-azabicyclo[3.1.0]hexan-6-ylethoxy)quinazolin-4,6-diamine

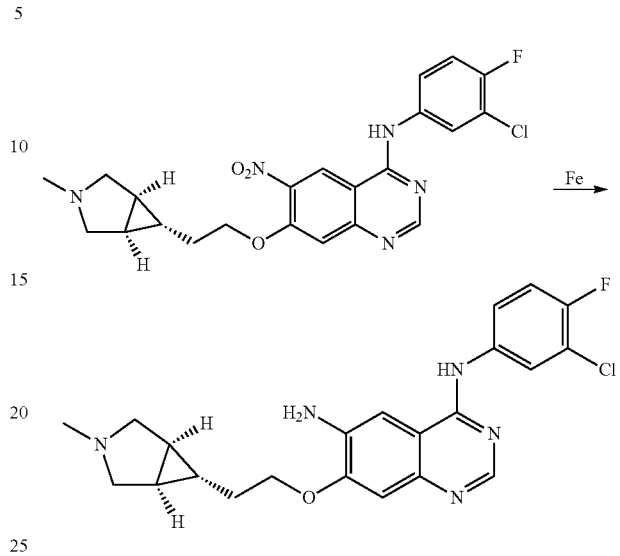

N-(4-(3-chloro-4-fluorophenyl))-7-2-((1R,5S,6S)-3-methyl-3-azabicyclo[3.1.0]hexan-6-yl ethoxy)-6-nitroquinazolin-4-amine (500 mg, 1.1 mmol) was dissolved in a mixed solvent of EtOH (10 mL) and CH₃COOH (3 mL). To the mixture was added Fe powder (343 mg, 6.12 mmol). The reaction was conducted at room temperature 12 h under stirring. After the completion of reaction, the mixture was rotary-evaporated under a reduced pressure to remove EtOH. Water (30 mL) was added. The mixture was adjusted with 1 mol/L NaOH solution until it became basic. The mixture was extracted with EA. The organic layer was rotary-evaporated to dryness under a reduced pressure. The resulting residue was purified by a silica gel column chromatography (eluted with dichloromethane/methanol=10/1) to produce N-(4-(3-chloro-4-fluorophenyl))-7-(2-((1R,5S,6S)-3-methyl-3-azabicyclo[3.1.0]hexan-6-ylethoxy)quinazolin-4,6-diamine (200 mg) in a yield of 43%.

(3) Preparation of N-[4-(3-chloro-4-fluorophenylamino)-7-(2-((1R,5S,6S)-3-methyl-3-azabicyclo[3.1.0]hexan-6-ylethoxy)quinazolin-6-yl]-acrylamide

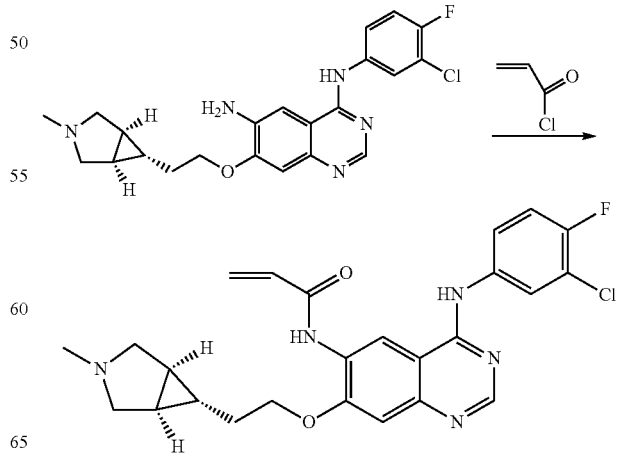

N-(4-(3-chloro-4-fluorophenyl))-7-(2-((1R,5S,6S)-3-methyl-3-azabicyclo[3.1.0]hexan-6-ylethoxy)quinazolin-4,6-diamine (200 mg, 0.47 mmol) was dissolved in dichloromethane (20 mL). Triethylamine (200 mg) and acryloyl chloride (43 mg, 0.47 mmol) were added under an ice bath. The mixture was stirred at room temperature for 30 min. After the completion of reaction, water (50 mL) was added. The mixture was extracted with EA. The organic layer was rotary-evaporated to dryness under a reduced pressure. The resulting residue was purified by a silica gel column chromatography (eluted with dichloromethane/methanol=5/1) to produce N-[4-(3-chloro-4-fluorophenylamino)-7-(2-((1R,5S,6S)-3-methyl-3-azabicyclo[3.1.0]hexan-6-ylethoxy)quinazolin-6-yl]-acrylamide 40 mg) in a yield of 18%.

Molecular formula: $C_{25}H_{25}ClFN_5O_2$

Mass spectrum (m/e): 482.2 (M+1), 241.6 (M/2)

$^1$HNMR (400 MHz, CDCl$_3$) δ9.15 (s, 1H), 8.94 (s, 1H), 8.60 (s, 1H), 7.89 (s, 1H), 7.83 (d, 1H), 7.58 (d, 1H), 7.22 (t, 1H), 7.05 (m, 1H), 6.49 (d, 1H), 5.86 (d, 1H), 4.38 (t, 2H), 3.78 (d, 2H), 3.10 (d, 2H), 2.80 (s, 3H), 2.39 (m, 1H), 1.83 (m, 2H), 1.74 (m, 2H).

Example 9 Preparation of N-[4-(3-chloro-4-fluorophenylamino)-7-((2-methyloctahydrocyclopenta[c]pyrrol-4-yl)methoxy)quinazolin-6-yl]-acrylamide (Compound 9)

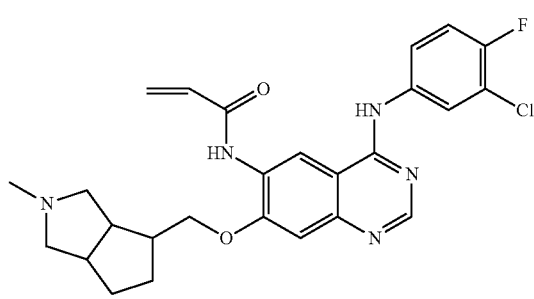 [SMILES: C=CC(=O)Nc1cc2c(Nc3ccc(F)c(Cl)c3)ncnc2cc1OCC1CCC2CN(C)CC12]

(1) Preparation of N-(4-(3-chloro-4-fluorophenyl))-7-((2-methyloctahydrocyclopenta[c]pyrrol-4-yl)methoxy)-6-nitroquinazolin-4-amine

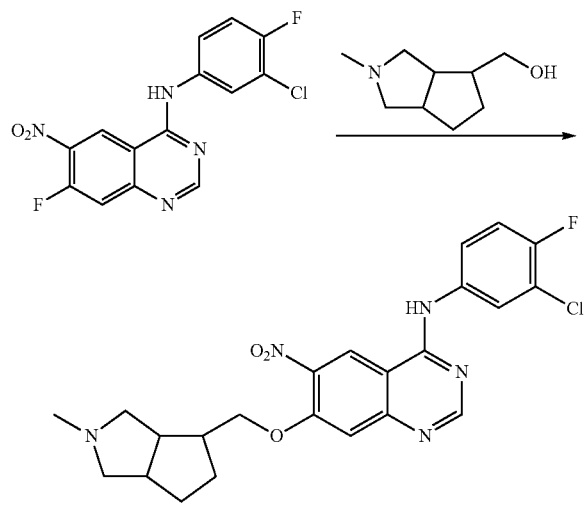

(2-methyloctahydrocyclopenta[c]pyrrol-4-yl)methanol (380 mg, 2.45 mmol) was dissolved in DMF (20 mL). 60% sodium hydride (1.6 g, 40 mmol) was added in batch in an ice bath under an atmosphere of N$_2$. The mixture was moved to an atmosphere of room temperature and stirred for 1 h. N-(4-(3-chloro-4-fluorophenyl))-7-fluoro-6-nitroquinazolin-4-amine (1.08 g, 3.2 mmol) was added. The mixture was stirred at 50° C. overnight. After the completion of reaction, water (50 mL) was added. The mixture was extracted with EA. The organic layer was rotary-evaporated to dryness under a reduced pressure to produce N-(4-(3-chloro-4-fluorophenyl))-7-((2-methyloctahydrocyclopenta[c]pyrrol-4-yl)methoxy)-6-nitroquinazolin-4-amine (318 mg) in a yield of 28%.

(2) N-(4-(3-chloro-4-fluorophenyl))-7-((2-methyloctahydrocyclopenta[c]pyrrol-4-yl)methoxy)quinazolin-4,6-diamine

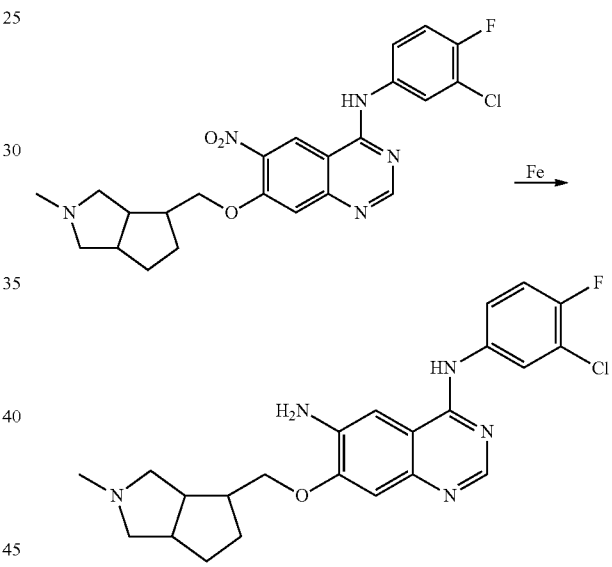

N-(4-(3-chloro-4-fluorophenyl))-7-((2-methyloctahydrocyclopenta[c]pyrrol-4-yl)methoxy)-6-nitroquinazolin-4-amine (318 mg, 0.68 mmol) was dissolved in a mixed solvent (8 mL) of acetic acid and ethanol (CH$_3$COOH/EtOH=1/3). To the mixture was added Fe powder (200 mg, 3.57 mmol). The mixture was warmed up to 70° C. and stirred for 1.5 h. After the completion of reaction, the mixture was rotary-evaporated under a reduced pressure to remove EtOH. Water (30 mL) was added. The mixture was adjusted with 1 mol/L NaOH solution until it became basic. The mixture was extracted with EA. The organic layer was rotary-evaporated to dryness under a reduce pressure. The residue was purified by a silica gel column chromatography (eluted with dichloromethane/methanol=15/1) to produce N-(4-(3-chloro-4-fluorophenyl))-7-((2-methyloctahydrocyclopenta[c]pyrrol-4-yl)methoxy)quinazolin-4,6-diamine (90 mg) in a yield of 30%.

(3) Preparation of N-[4-(3-chloro-4-fluorophenylamino)-7-((2-methyloctahydrocyclopenta[c]pyrrol-4-yl)methoxy)quinazolin-6-yl]-acrylamide

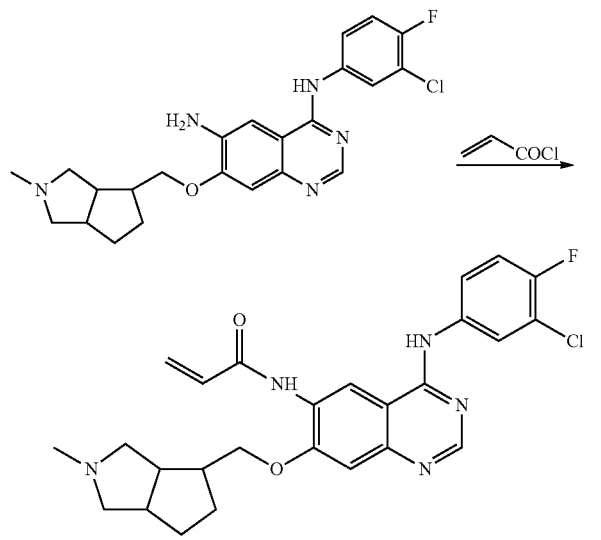

N-(4-(3-chloro-4-fluorophenyl))-7-((2-methyloctahydrocyclopenta[c]pyrrol-4-yl)methoxy)quinazolin-4,6-diamine (80 mg, 0.18 mmol) was dissolved in dichloromethane (30 mL). Triethylamine (40 mg) was added. Acryloyl chloride (16 mg, 0.18 mmol) was added dropwise under an ice bath. The mixture was stirred at room temperature for 0.5 h. After the completion of reaction, water (50 mL) was added. The mixture was extracted with EA. The organic layer was rotary-evaporated to dryness under a reduced pressure. The resulting residue was purified by a silica gel column chromatography (eluted with dichloromethane/methanol=20/1) to produce N-[4-(3-chloro-4-fluorophenylamino)-7-((2-methyloctahydrocyclopenta[c]pyrrol-4-yl)methoxy)-acrylamide 20 mg) in a yield of 22%.

Molecular formula: $C_{26}H_{27}ClFN_5O_2$

Mass spectrum (m/e): 496.3 (M+1), 248.7 (M/2)

$^1$HNMR (400 MHz, CDCl$_3$) δ8.79 (s, 1H), 8.56 (s, 1H), 7.96 (d, 1H), 7.61 (d, 1H), 7.29 (s, 1H), 7.15 (m, 1H), 6.70 (m, 1H), 6.51 (d, 1H), 5.85 (d, 1H), 4.18 (m, 1H), 4.10 (m, 1H), 3.41-3.95 (m, 2H), 3.38 (d, 1H), 3.03-3.12 (m, 4H), 2.82 (s, 3H), 2.15 (s, 3H), 1.22 (m, 3H).

Example 10 Preparation of N-[4-(3-chloro-4-fluorophenylamino)-7-((7-methyl-7-azabicyclo[2.2.1]heptan-2-yl)methoxy)quinazolin-6-yl]-acrylamide (Compound 10)

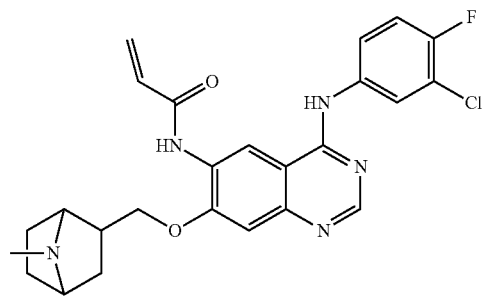 [SMILES: C=CC(=O)Nc1cc2c(Nc3ccc(F)c(Cl)c3)ncnc2cc1OCC1CC2CCC1N2C]

(1) Preparation of N-(4-(3-chloro-4-fluorophenyl))-7-((7-methyl-7-azabicyclo[2.2.1]heptan-2-yl)methoxy)-6-nitroquinazolin-4-amine

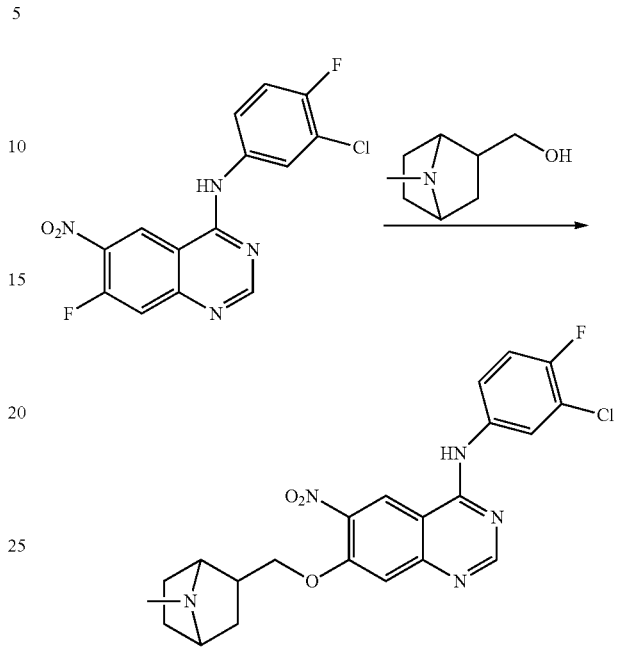

(7-methyl-7-azabicyclo[2.2.1]heptan-2-yl)methanol (283 mg, 2.0 mmol) was dissolved in DMF (10 mL). 60% sodium hydride (160 g, 4.0 mmol) was added in batch in an ice bath under an atmosphere of N2. The mixture was moved to an atmosphere of room temperature and stirred for 1 h. N-(4-(3-chloro-4-fluorophenyl))-7-fluoro-6-nitroquinazolin-4-amine (1.13 g, 3.0 mmol) was added. The mixture was stirred at 50° C. overnight. After the completion of reaction, water (50 mL) was added. The mixture was extracted with EA. The organic layer was rotary-evaporated to dryness under a reduced pressure. The resulting residue was purified by a silica gel column chromatography (eluted with dichloromethane/methanol=8/1) to produce N-(4-(3-chloro-4-fluorophenyl))-7-((7-methyl-7-azabicyclo[2.2.1]heptan-2-yl)methoxy)-6-nitroquinazolin-4-amine (427 mg) in a yield of 47%.

(2) Preparation of N-(4-(3-chloro-4-fluorophenyl))-7-((7-methyl-7-azabicyclo[2.2.1]heptan-2-yl)methoxy)quinazolin-4,6-diamine

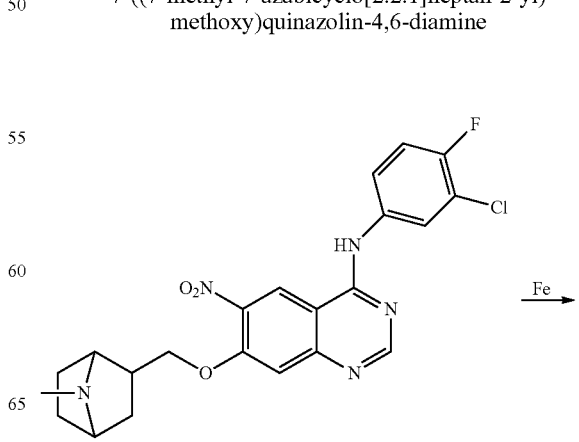

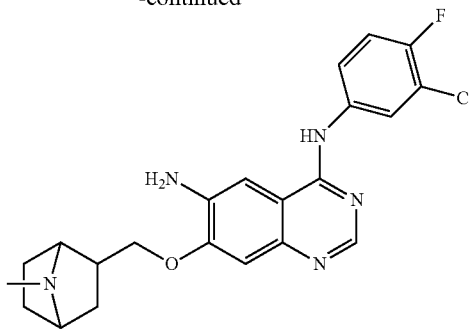

N-(4-(3-chloro-4-fluorophenyl))-7-((7-methyl-7-azabicyclo[2.2.1]heptan-2-yl)methoxy)-6-nitroquinazolin-4-amine (427 mg, 0.93 mmol) was dissolved in a mixed solvent (28 mL) of acetic acid and ethanol ($CH_3COOH/EtOH=1/3$). To the mixture was added Fe powder (312 mg, 5.58 mmol). The mixture was warm up to 70° C. and stirred for 1 h. After the completion of reaction, the mixture was rotary-evaporated under a reduced pressure to remove EtOH. Water (30 mL) was added. The mixture was adjusted with 1 mol/L NaOH solution until it became basic. The mixture was extracted with EA. The organic layer was rotary-evaporated to dryness under a reduced pressure to produce N-(4-(3-chloro-4-fluorophenyl))-7-((7-methyl-7-azabicyclo[2.2.1]heptan-2-yl)methoxy)quinazolin-4,6-diamine (157 mg) in a yield of 40%.

(3) Preparation of N-[4-(3-chloro-4-fluorophenylamino)-7-((7-methyl-7-azabicyclo[2.2.1]heptan-2-yl)methoxy)quinazolin-6-yl]-acrylamide

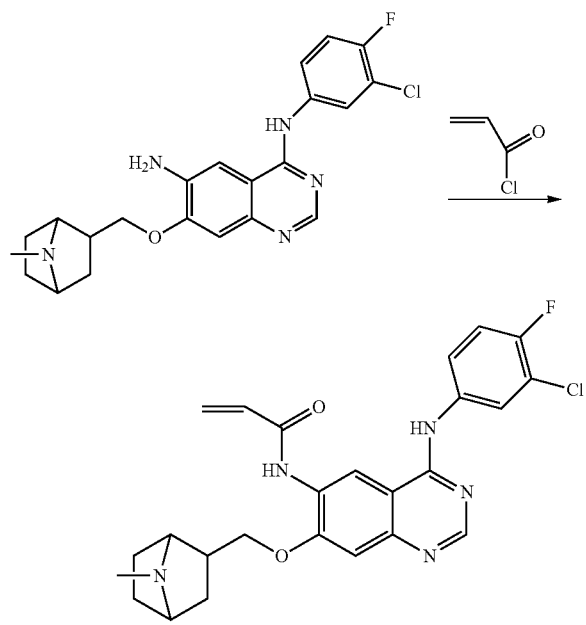

N-(4-(3-chloro-4-fluorophenyl))-7-((7-methyl-7-azabicyclo[2.2.1]heptan-2-yl)methoxy)quinazolin-4,6-diamine (157 mg, 0.37 mmol) was dissolved in dichloromethane (10 mL). Triethylamine (111 mg, 1.10 mmol) and acryloyl chloride (33 mg, 0.37 mmol) were added under an ice bath. The mixture was stirred at room temperature overnight. After the completion of reaction, water (50 mL) was added. The mixture was extracted with EA. The organic layer was rotary-evaporated to dryness under a reduced pressure. The resulting residue was purified by a silica gel column chromatography (eluted with dichloromethane/methanol=15/1) to produce N-[4-(3-chloro-4-fluorophenylamino)-7-((7-methyl-7-azabicyclo[2.2.1]heptan-2-yl)methoxy)quinazolin-6-yl]-acrylamide 20 mg) in a yield of 11%.

Molecular formula: $C_{25}H_{25}ClFN_5O_2$

Mass spectrum (m/e): 482.2 (M+1), 241.7 (M/2)

$^1$HNMR (400 MHz, $CDCl_3$) δ9.08 (s, 1H), 8.64 (s, 1H), 8.16 (s, 1H), 7.88 (m, 2H), 7.51 (d, 1H), 7.24 (s, 1H), 7.10 (t, 1H), 6.48 (d, 1H), 6.38 (m, 1H), 5.88 (d, 1H), 4.22 (m, 1H), 4.10 (t, 1H), 3.56 (s, 1H), 3.44 (s, 1H), 2.94 (m, 1H), 2.46 (s, 3H), 2.25 (m, 1H), 1.99 (m, 1H), 1.70 (m, 1H), 1.68 (m, 1H), 1.41 (m, 1H), 1.05 (m, 1H).

Example 11 Preparation of N-[4-(3-chloro-4-fluorophenylamino)-7-(2-(3-methyl-3-azabicyclo[3.2.1]octan-8-yl)ethoxy)quinazolin-6-yl]-acrylamide (Compound 11)

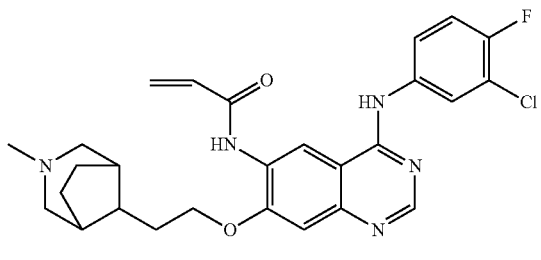 [SMILES: C=CC(=O)Nc1cc2c(Nc3ccc(F)c(Cl)c3)ncnc2cc1OCCC1C2CCC1CN(C)C2]

(1) Preparation of N-(4-(3-chloro-4-fluorophenyl))-7-(2-(3-methyl-3-azabicyclo[3.2.1]octan-8-yl)ethoxy)-6-nitroquinazolin-4-amine

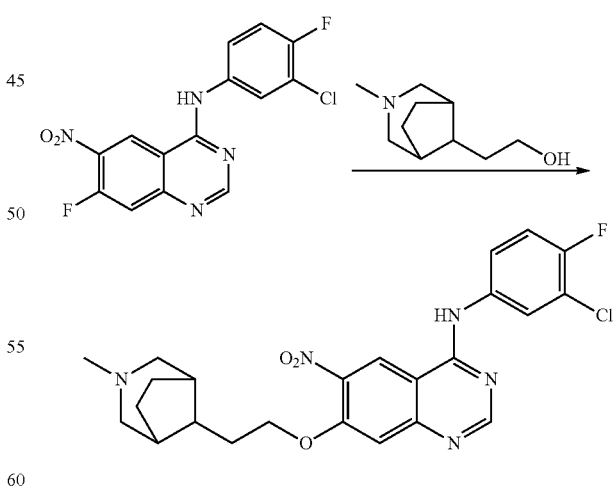

2-(3-methyl-3-azabicyclo[3.2.1]octan-8-yl)ethanol (338 mg, 2 mmol) was dissolved in DMF (20 mL). 60% sodium hydride (0.4 g, 10 mmol) was added in batch in an ice bath under an atmosphere of $N_2$. The mixture was moved to an atmosphere of room temperature and stirred for 1 h. N-(4-(3-chloro-4-fluorophenyl))-7-fluoro-6-nitroquinazolin-4-amine (1.12 g, 3.3 mmol) was added. The mixture was stirred at 50° C. overnight. After the completion of reaction, water (50 mL) was added. The mixture was extracted with EA. The organic layer was rotary-evaporated to dryness under a reduced pressure to produce N-(4-(3-chloro-4-fluorophenyl))-7-(2-(3-methyl-3-azabicyclo[3.2.1]octan-8-yl)ethoxy)-6-nitroquinazolin-4-amine (560 mg) in a yield of 58%.

(2) Preparation of N-(4-(3-chloro-4-fluorophenyl))-7-(2-(3-methyl-3-azabicyclo[3.2.1]octan-8-yl)ethoxy)quinazolin-4,6-diamine

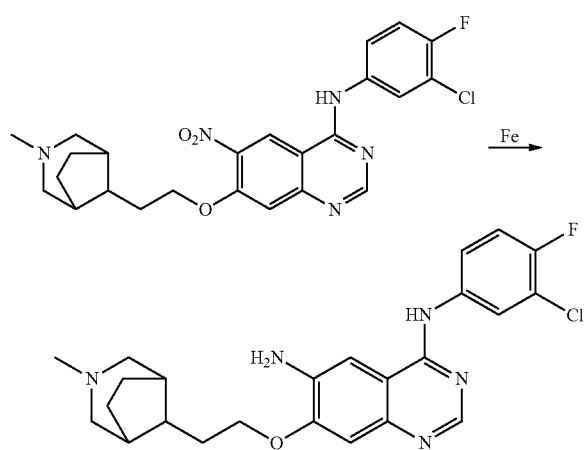

N-(4-(3-chloro-4-fluorophenyl))-7-(2-(3-methyl-3-azabicyclo[3.2.1]octan-8-yl)ethoxy)-6-nitroquinazolin-4-amine (560 mg, 1.15 mmol) was dissolved in a mixed solvent (20 mL) of acetic acid and ethanol (CH$_3$COOH/EtOH=1/3). To the mixture was added Fe powder (343 mg, 6.12 mmol). The mixture was warmed up to 70° C. and stirred for 1 h. After the completion of reaction, the mixture was rotary-evaporated under a reduced pressure to remove EtOH. Water (30 mL) was added. The mixture was adjusted with 1 mol/L NaOH solution until it became basic. The mixture was extracted with EA. The organic layer was rotary-evaporated to dryness under a reduced pressure to produce N-(4-(3-chloro-4-fluorophenyl))-7-(2-(3-methyl-3-azabicyclo[3.2.1]octan-8-yl)ethoxy)quinazolin-4,6-diamine (360 mg) in a yield of 69%.

(3) Preparation of N-[4-(3-chloro-4-fluorophenylamino)-7-(2-(3-methyl-3-azabicyclo[3.2.1]octan-8-yl)ethoxy)quinazolin-6-yl]-acrylamide

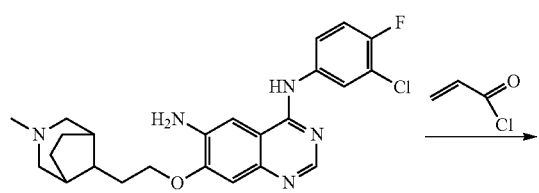

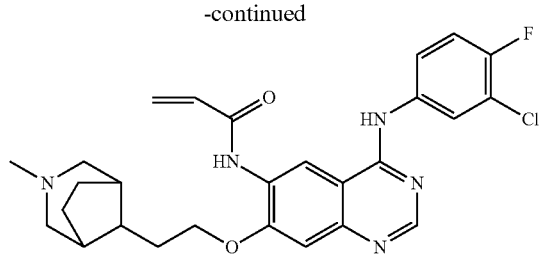

N-(4-(3-chloro-4-fluorophenyl))-7-(2-(3-methyl-3-azabicyclo[3.2.1]octan-8-yl)ethoxy)quinazolin-4,6-diamine (360 mg, 0.79 mmol) and triethylamine (112 mg) were dissolved in dichloromethane (20 mL). Acryloyl chloride (71 mg, 0.79 mmol) was added dropwise. The mixture was stirred at room temperature for 1 h. After the completion of reaction, water (50 mL) was added. The mixture was extracted with EA, and rotary-vaporated to dryness under a reduced pressure. The residue was washed with diethyl ether to produce N-[4-(3-chloro-4-fluorophenylamino)-7-(2-(3-methyl-3-azabicyclo[3.2.1]octan-8-yl)ethoxy)quinazolin-6-yl]-acrylamide (34 mg) in a yield of 8%.

Molecular formula: $C_{27}H_{29}ClFN_5O_2$

Mass spectrum (m/e): 510.3 (M+1), 255.8 (M/2)

$^1$HNMR (400 MHz, CDCl$_3$) δ9.13 (s, 1H), 8.67 (s, 1H), 8.15 (s, 1H), 7.94 (d, 1H), 7.61 (s, 1H), 7.53 (d, 1H), 7.15 (t, 1H), 6.50 (d, 1H), 6.34 (m, 1H), 5.90 (d, 1H), 4.29 (m, 2H), 2.69 (t, 1H), 2.66 (d, 1H), 2.50 (s, 3H), 1.27-2.35 (m, 11H).

Example 12 Preparation of N-[4-(3-chloro-4-fluorophenylamino)-7-((5-methyl-5-azaspiro[2.4]heptan-1-yl)methoxy)quinazolin-6-yl]-acrylamide (Compound 12)

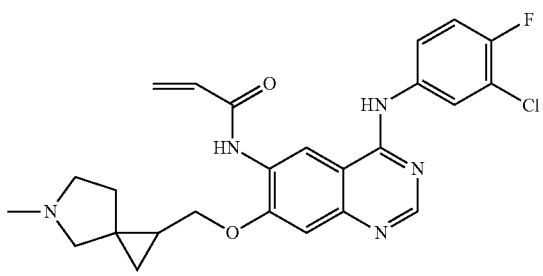 [SMILES: C=CC(=O)Nc1cc2c(Nc3ccc(F)c(Cl)c3)ncnc2cc1OCC1CC12CCN(C)C2]

(1) Preparation of N-(4-(3-chloro-4-fluorophenyl))-7-((5-methyl-5-azaspiro[2.4]heptan-1-yl)methoxy)-6-nitroquinazolin-4-amine

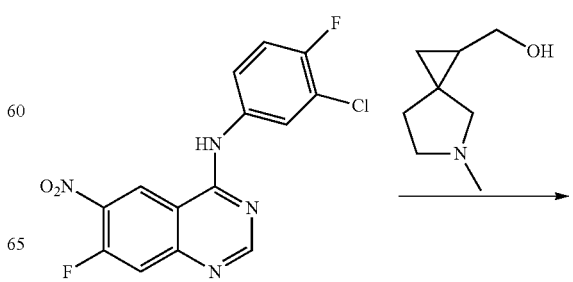

-continued

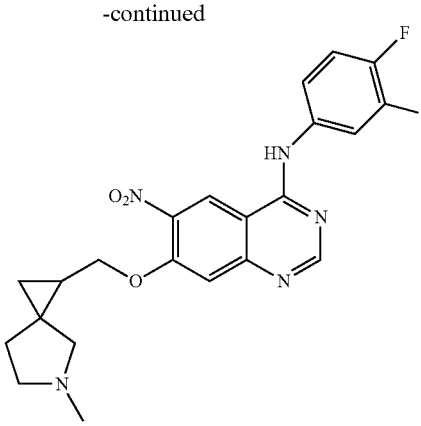

(5-methyl-5-azaspiro[2.4]heptan-1-yl)methanol (370 mg, 2.62 mmol) was dissolved in DMF (20 mL). 60% sodium hydride (157 mg, 3.93 mmol) was added in batch in an ice bath under an atmosphere of N2. The mixture was moved to an atmosphere of room temperature and stirred for 1 h. N-(4-(3-chloro-4-fluorophenyl))-7-fluoro-6-nitroquinazolin-4-amine (588 mg, 1.75 mmol) was added. The mixture was stirred at room temperature overnight. After the completion of reaction, water (20 mL) was added. The mixture was filtered. The filtered cake was dried in vacuum to produce N-(4-(3-chloro-4-fluorophenyl))-7-((5-methyl-5-azaspiro [2.4]heptan-1-yl)methoxy)-6-nitroquinazolin-4-amine (690 mg) in a yield of 86%.

(2) Preparation of N-(4-(3-chloro-4-fluorophenyl))-7-((5-methyl-5-azaspiro[2.4]heptan-1-yl)methoxy) quinazolin-4,6-diamine

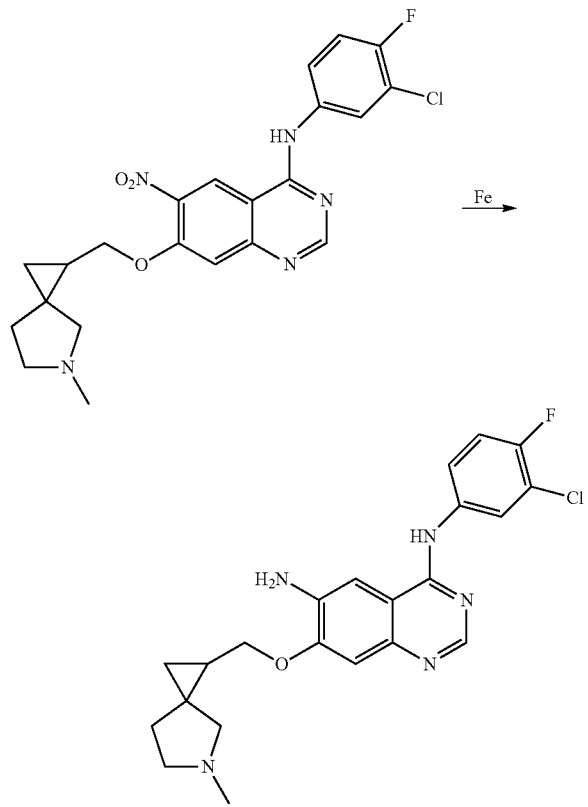

N-(4-(3-chloro-4-fluorophenyl))-7-((5-methyl-5-azaspiro [2.4]heptan-1-yl)methoxy)-6-nitroquinazolin-4-amine (69 mg, 1.51 mmol) was dissolved in a mixed solvent (60 mL) of acetic acid and ethanol (CH$_3$COOH/EtOH=1/3). To the mixture was added Fe powder (507 mg, 9.06 mmol). The mixture was warm up to 30° C. and stirred for 12 h. After the completion of reaction, the mixture was rotary-evaporated under a reduced pressure to remove EtOH. Water (30 mL) was added. The mixture was adjusted with 1 mol/L NaOH solution until it became basic. The mixture was extracted with EA. The organic layer was rotary-evaporated to dryness under a reduce pressure. The resulting residue was purified by a silica gel column chromatography (eluted with dichloromethane/methanol=10/1) to produce N-(4-(3-chloro-4-fluorophenyl))-7-((5-methyl-5-azaspiro[2.4]heptan-1-yl) methoxy)quinazolin-4,6-diamine (100 mg) in a yield of 15%.

(3) Preparation of N-[4-(3-chloro-4-fluorophenylamino)-7-((5-methyl-5-azaspiro[2.4]heptan-1-yl) methoxy)quinazolin-6-yl]-acrylamide

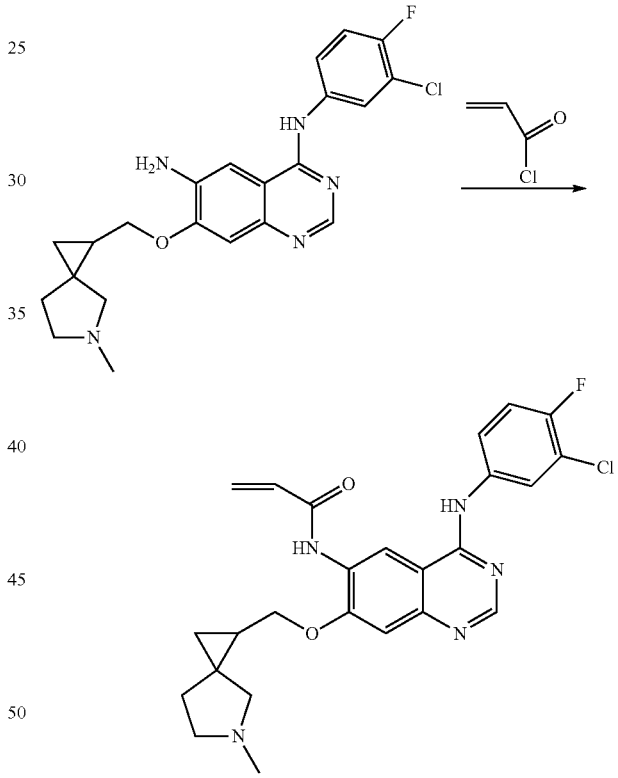

N-(4-(3-chloro-4-fluorophenyl))-7-((5-methyl-5-azaspiro [2.4]heptan-1-yl)methoxy)quinazolin-4,6-diamine (100 mg, 0.23 mmol) was dissolved in DCM (10 mL). Triethylamine (46 mg, 0.46 mmol) was added. Acryloyl chloride (19 mg, 0.21 mmol) was added dropwise in an ice-water bath. The mixture was stirred at room temperature for 30 min. After the completion of reaction, water (50 mL) was added. The mixture was extracted with EA, and rotary-evaporated to dryness under a reduce pressure. The resulting residue was purified by a silica gel column chromatography (eluted with dichloromethane/methanol=15/1) to produce N-[4-(3-chloro-4-fluorophenylamino)-7-((5-methyl-5-azaspiro[2.4] heptan-1-yl)methoxy)quinazolin-6-yl]-acrylamide (14 mg) in a yield of 14%.

Molecular formula: $C_{25}H_{25}ClFN_5O_2$

Mass spectrum (m/e): 482.3 (M+1), 241.6 (M/2)

$^1$HNMR (400 MHz, CDCl$_3$) δ9.35 (s, 1H), 9.00 (s, 1H), 8.60 (s, 1H), 7.98 (s, 1H), 7.78 (d, 1H), 7.54 (d, 1H), 6.95 (m, 2H), 6.52 (m, 2H), 5.83 (m, 1H), 4.57 (m, 1H), 3.65 (m, 1H), 0.68-3.23 (m, 12H).

Example 13 Preparation of N-[4-(3-chloro-4-fluorophenylamino)-7-((6-methyl-6-azaspiro[2.5]octan-1-yl)methoxy)quinazolin-6-yl]-acrylamide (Compound 13)

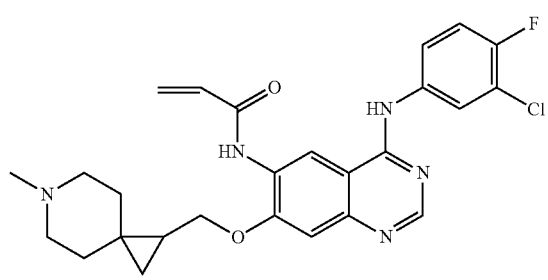 [SMILES: C=CC(=O)Nc1cc2c(Nc3ccc(F)c(Cl)c3)ncnc2cc1OCC1CC12CCN(C)CC2]

(1) Preparation of N-(4-(3-chloro-4-fluorophenyl))-7-((6-methyl-6-azaspiro[2.5]octan-1-yl)methoxy)-6-nitro quinazolin-4-amine

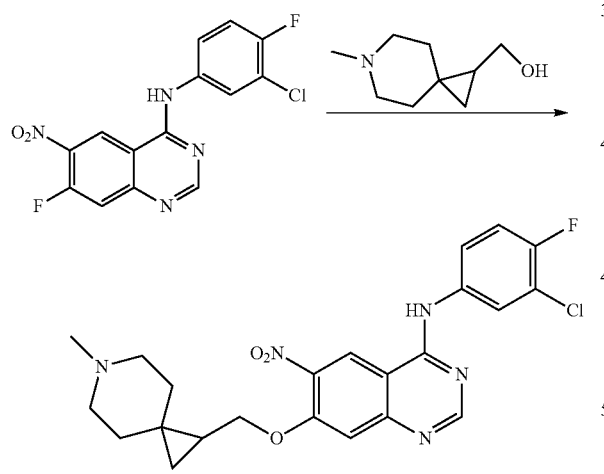

(6-methyl-6-azaspiro[2.5]octan-1-yl)methanol (400 mg, 2.58 mmol) was dissolved in DMF (20 mL). 60% sodium hydride (230 mg, 3.87 mmol) was added in batch in an ice bath under an atmosphere of N$_2$. The mixture was moved to an atmosphere of room temperature and stirred for 1 h. N-(4-(3-chloro-4-fluorophenyl))-7-fluoro-6-nitroquinazolin-4-amine (954 mg, 2.83 mmol) was added. The mixture was stirred at room temperature overnight. After the completion of reaction, water (20 mL) was added. The mixture was filtered. The filtered cake was dried in vacuum to produce N-(4-(3-chloro-4-fluorophenyl))-7-((6-methyl-6-azaspiro[2.5]octan-1-yl)methoxy)-6-nitro quinazolin-4-amine (300 mg) in a yield of 25%.

(2) Preparation of N-(4-(3-chloro-4-fluorophenyl))-7-((6-methyl-6-azaspiro[2.5]octan-1-yl)methoxy)quinazolin-4,6-diamine

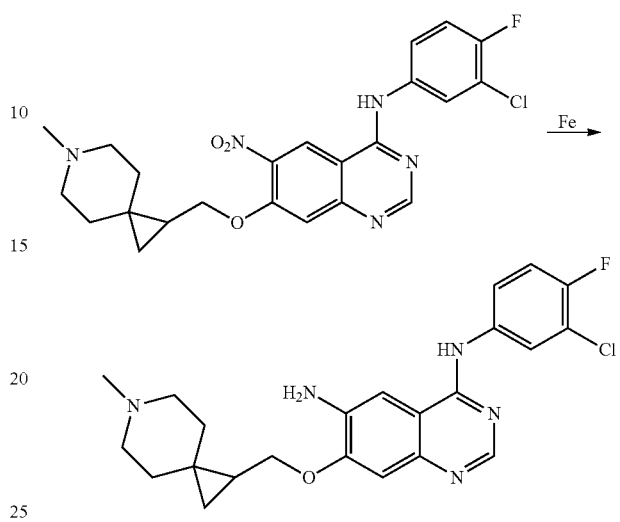

N-(4-(3-chloro-4-fluorophenyl))-7-((6-methyl-6-azaspiro[2.5]octan-1-yl)methoxy)-6-nitro quinazolin-4-amine (300 mg, 0.64 mmol) was dissolved in a mixed solvent (60 mL) of acetic acid and ethanol (CH$_3$COOH/EtOH=1/3). To the mixture was added Fe powder (177 mg, 3.18 mmol). The mixture was warmed up to 30° C. and stirred for 12 h. After the completion of reaction, the mixture was rotary-evaporated under a reduced pressure to remove EtOH. Water (30 mL) was added. The mixture was adjusted with 1 mol/L NaOH solution until it became basic. The mixture was extracted with EA. The organic layer was rotary-evaporated to dryness under a reduced pressure to produce N-(4-(3-chloro-4-fluorophenyl))-7-((6-methyl-6-azaspiro[2.5]octan-1-yl)methoxy)quinazolin-4,6-diamine (200 mg) in a yield of 71%.

(3) Preparation of N-[4-(3-chloro-4-fluorophenylamino)-7-((6-methyl-6-azaspiro[2.5]octan-1-yl)methoxy)quinazolin-6-yl]-acrylamide

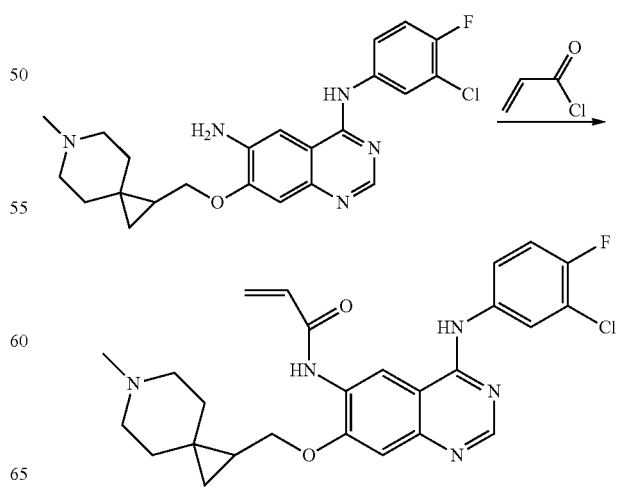

N-(4-(3-chloro-4-fluorophenyl))-7-((6-methyl-6-azaspiro[2.5]octan-1-yl)methoxy)quinazolin-4,6-diamine (200 mg, 0.45 mmol) was dissolved in DCM (10 mL). Triethylamine (46 mg, 0.46 mmol) was added. Acryloyl chloride (39 mg, 0.43 mmol) was added dropwise in an ice-water bath. The mixture was stirred at room temperature for 30 min. After the completion of reaction, water (50 mL) was added. The mixture was extracted with EA. The organic layer was rotary-evaporated to dryness under a reduced pressure. The resulting residue was purified by a silica gel column chromatography (eluted with dichloromethane/methanol=15/1) to produce N-[4-(3-chloro-4-fluorophenylamino)-7-((6-methyl-6-azaspiro[2.5]octan-1-yl)methoxy)quinazolin-6-yl]-acrylamide 25 mg) in a yield of 12%.

Molecular formula: $C_{26}H_{27}ClFN_5O_2$

Mass spectrum (m/e): 496.2 (M+1), 248.6 (M/2)

$^1$HNMR (400 MHz, CDCl$_3$) δ9.13 (s, 1H), 8.66 (s, 1H), 8.32 (s, 1H), 7.97 (d, 1H), 7.66 (s, 1H), 7.55 (d, 1H), 7.25 (s, 1H), 7.17 (t, 1H), 6.52 (d, 1H), 6.42 (m, 1H), 5.90 (d, 1H), 4.39 (m, 1H), 4.07 (t, 1H), 2.69 (m, 2H), 2.55 (m, 2H), 2.40 (s, 3H), 2.04 (s, 1H), 1.80 (m, 2H), 1.56 (m, 2H), 1.30 (m, 2H).

Example 14 Preparation of N-[4-(3-chloro-4-fluorophenylamino)-7-(2-(6-methyl-6-azaspiro[2.5]octan-1-yl)ethoxy)quinazolin-6-yl]-acrylamide (Compound 14)

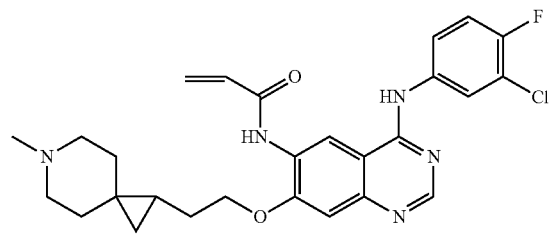 [SMILES: C=CC(=O)Nc1cc2c(Nc3ccc(F)c(Cl)c3)ncnc2cc1OCCC1CC12CCN(C)CC2]

(1) Preparation of N-(4-(3-chloro-4-fluorophenyl))-7-(2-(6-methyl-6-azaspiro[2.5]octan-1-yl)ethoxy)-6-nitroquinazolin-4-amine

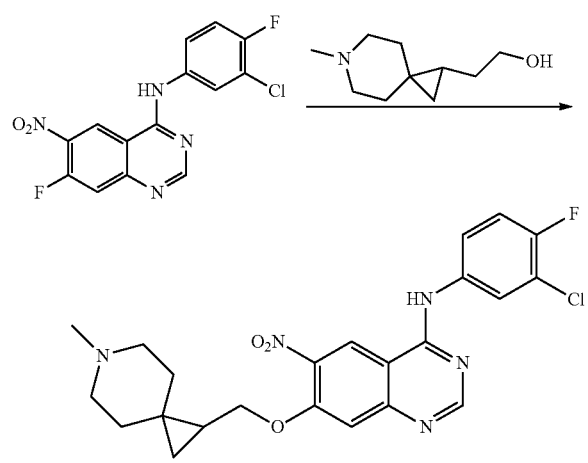

2-(6-methyl-6-azaspiro[2,5]octan-1-yl)ethanol (9 g, 53 mmol) was dissolved in DMF (200 mL). 60% sodium hydride (10 g, 0.25 mol) was added in batch in an ice bath under an atmosphere of N$_2$. The mixture was moved to an atmosphere of room temperature and stirred for 1 h. N-(4-(3-chloro-4-fluorophenyl))-7-fluoro-6-nitroquinazolin-4-amine (18 g, 53 mmol) was added. The mixture was stirred at room temperature overnight. After the completion of reaction, water (20 mL) was added. The mixture was filtered. The filtered cake was purified by a silica gel column chromatography (eluted with dichloromethane/methanol=20/1) to produce N-(4-(3-chloro-4-fluorophenyl))-7-(2-(6-methyl-6-azaspiro[2.5]octan-1-yl)ethoxy)-6-nitroquinazolin-4-amine (17.0 g) in a yield of 66%.

(2) Preparation of N-(4-(3-chloro-4-fluorophenyl))-7-(2-(6-methyl-6-azaspiro[2.5]octan-1-yl)ethoxy)quinazolin-4,6-diamine

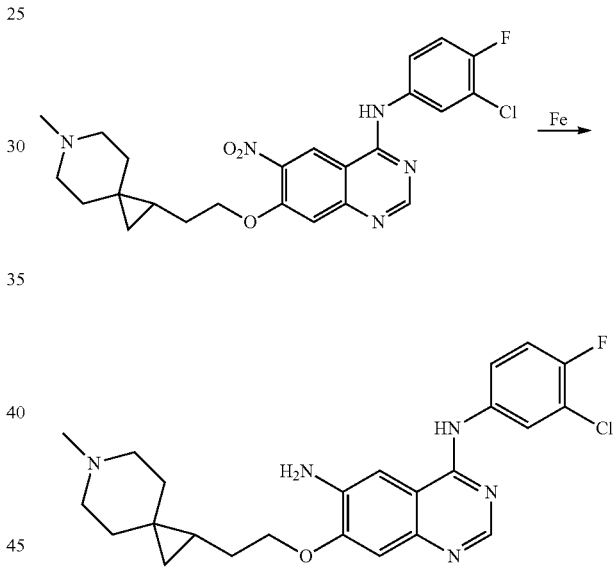

N-(4-(3-chloro-4-fluorophenyl))-7-(2-(6-methyl-6-azaspiro[2.5]octan-1-yl)ethoxy)-6-nitroquinazolin-4-amine (17 g, 35 mmol) was dissolved in a mixed solvent (300 mL) of acetic acid and ethanol (CH$_3$COOH/EtOH=1/3). To the mixture was added Fe powder (13.6 g, 243 mmol). The mixture was stirred at room temperature for 12 h. After the completion of reaction, the mixture was rotary-evaporated under a reduced pressure to remove EtOH. Water (30 mL) was added. The mixture was adjusted with 1 mol/L NaOH solution until it became basic. The mixture was extracted with EA. The organic layer was rotary-evaporated to dryness under a reduce pressure. The resulting residue was purified by a silica gel column chromatography (eluted with dichloromethane/methanol=20/1) to produce N-(4-(3-chloro-4-fluorophenyl))-7-(2-(6-methyl-6-azaspiro[2.5]octan-1-yl)ethoxy)quinazolin-4,6-diamine (8.2 g) in a yield of 51%.

(3) Preparation of N-[4-(3-chloro-4-fluorophenylamino)-7-(2-(6-methyl-6-azaspiro[2.5]octan-1-yl)ethoxy)quinazolin-6-yl]-acrylamide

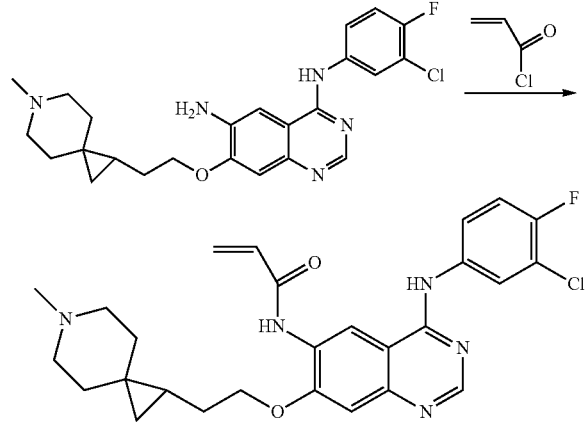

N-(4-(3-chloro-4-fluorophenyl))-7-(2-(6-methyl-6-azaspiro[2.5]octan-1-yl)ethoxy)quinazolin-4,6-diamine (300 mg, 6.6 mmol) was dissolved in DCM (50 mL). Triethylamine (2.0 g, 145 mmol) was added. Acryloyl chloride (600 mg, 6.7 mmol) was added dropwise in an ice-water bath. The mixture was stirred at room temperature for 30 min. After the completion of reaction, water (50 mL) was added. The mixture was extracted with EA. The organic layer was rotary-evaporated to dryness under a reduced pressure. The resulting residue was purified by a silica gel column chromatography (eluted with dichloromethane/methanol=30/1) to produce N-[4-(3-chloro-4-fluorophenylamino)-7-(2-(6-methyl-6-azaspiro[2.5]octan-1-yl)ethoxy)quinazolin-6-yl]-acrylamide 0.5 g) in a yield of 15%.

Molecular formula: $C_{27}H_{29}ClFN_5O_2$

Mass spectrum (m/e): 510.2 (M+1), 255.9 (M/2)

$^1$H NMR (400 MHz, CDCl$_3$) δ9.14 (s, 1H), 8.69 (s, 1H), 8.24 (s, 1H), 7.99 (d, 1H), 7.55 (m, 1H), 7.53 (m, 1H), 7.27 (s, 1H), 7.19 (t, 1H), 6.52 (d, 1H), 6.41 (m, 1H), 5.90 (d, 1H), 4.34 (m, 2H), 2.82 (m, 2H), 2.80 (m, 2H), 2.38 (s, 3H), 0.62-2.19 (m, 9H).

Example 15 Preparation of (E)-N-[4-(3-chloro-4-fluorophenylamino)-7-(2-((1R,5S,6S)-3-methyl-3-azabicyclo[3.1.0]hexan-6-yl)ethoxy)quinazolin-6-yl]-2-butenamide (Compound 15)

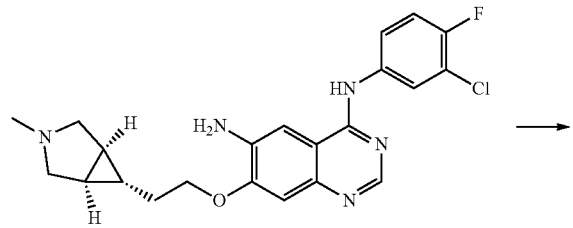

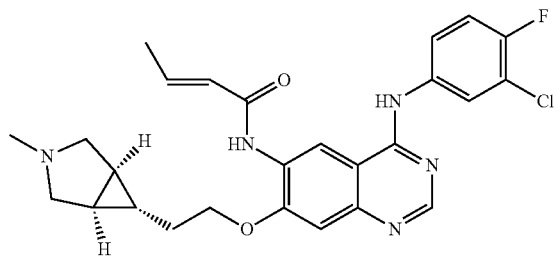

N-(4-(3-chloro-4-fluorophenyl))-7-(2-((1R,5S,6S)-3-methyl-3-azabicyclo[3.1.0]hexan-6-yl)ethoxy)quinazolin-4,6-diamine was prepared according to steps (1) and (2) of Example 8.

Trans-2-butenoic acid (0.12 g, 1.2 mmol) was dissolved in DMF (5 mL). Then HATU (0.05 g, 1.32 mmol), triethylamine (0.5 mL) and N-(4-(3-chloro-4-fluorophenyl))-7-(2-((1R,5S,6S)-3-methyl-3-azabicyclo[3.1.0]hexan-6-yl)ethoxy)quinazolin-4,6-diamine (500 mg, 1.2 mmol) were added. The mixture was stirred at room temperature for 12 h. After the completion of reaction, water (50 mL) was added. The reaction was extracted with dichloromethane. The organic layer was rotary-evaporated to dryness under a reduced pressure. The resulting residue was purified by a silica gel column chromatography (eluted with dichloromethane/methanol=10/1-5/1) to produce (E)-N-[4-(3-chloro-4-fluorophenylamino)-7-(2-((1R,5S,6S)-3-methyl-3-azabicyclo[3.1.0]hexan-6-yl)ethoxy)quinazolin-6-yl]-acrylamide (30 mg) in a yield of 5%.

Molecular formula: $C_{26}H_{27}ClFN_5O_2$

Mass spectrum (m/e): 496.2 (M+1), 248.6 (M/2)

$^1$H NMR (400 MHz, DMSO-d$_6$) δ 10.45 (br s, 1H), 9.40 (br s, 1H), 8.97 (s, 1H), 8.69 (s, 1H), 8.05 (s, 1H), 7.72 (m, 1H), 7.46 (t, 1H), 7.29 (m, 1H), 6.98 (m, 1H), 6.47 (d, 1H), 4.26 (m, 2H), 3.54 (m, 2H), 3.34 (m, 3H), 2.76 (s, 3H), 1.74-1.91 (m, 6H), 1.23 (m, 1H).

Example 16 Preparation of (E)-N-[4-(3-chloro-4-fluorophenylamino)-7-((7-methyl-7-azaspiro[3.5]nonan-2-yl)methoxy)quinazolin-6-yl]-2-butenamide (Compound 16)

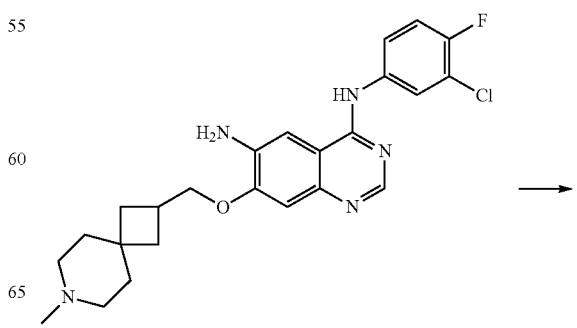

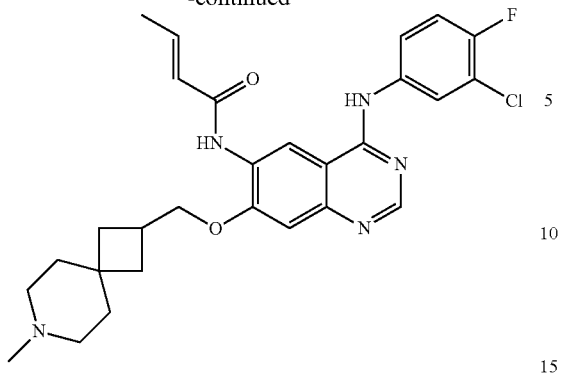

N-(4-(3-chloro-4-fluorophenyl))-7-((7-methyl-7-azaspiro[3.5]nonan-2-yl)methoxy)quinazolin-4,6-diamine was prepared according to steps (1) and (2) of Example 18.

Trans-2-butenoic acid (98 mg, 1.1 mmol) was dissolved in DMF (10 mL). Then HATU (563 g, 1.32 mmol), DIEA (441 mg, 3.4 mmol) and N-(4-(3-chloro-4-fluorophenyl)-7-((7-methyl-7-azaspiro[3.5]nonan-2-yl))methoxy)quinazolin-4,6-diamine (400 mg, 0.88 mmol) were added. The mixture was stirred at room temperature for 12 h. After the completion of reaction, water (50 mL) was added. The reaction was extracted with dichloromethane. The organic layer was rotary-evaporated to dryness under a reduced pressure. The resulting residue was purified by a silica gel column chromatography (eluted with dichloromethane/methanol=10/1-5/1) to produce (E)-N-[4-(3-chloro-4-fluorophenylamino)-7-((7-methyl-7-azaspiro[3.5]nonan-2-yl))methoxy)quinazolin-6-yl]-2-butenamide 30 mg) in a yield of 7%.

Molecular formula: $C_{28}H_{31}ClFN_5O_2$ MW: 524

Mass spectrum (m/e): 524.2 (M+1), 262.6 (M/2)

$^1$H NMR (400 MHz, CDCl$_3$) δ9.08 (s, 1H), 8.65 (s, 1H), 8.03 (s, 1H), 7.96 (d, 1H), 7.52 (d, 1H), 7.23 (s, 1H), 7.15 (t, 1H), 7.06 (m, 1H), 5.99 (d, 1H), 4.17 (d, 2H), 2.84 (m, 1H), 2.27 (m, 4H), 2.26 (s, 3H), 2.00 (m, 2H), 1.97 (d, 3H), 1.62-1.82 (m, 6H).

Example 17 Preparation of (E)-N-[4-(3-chloro-4-fluorophenylamino)-7-((7-methyl-7-azaspiro[3.5]nonan-2-yl)methoxy)quinazolin-6-yl]-2-pentenamide (Compound 17) and its hydrochloride

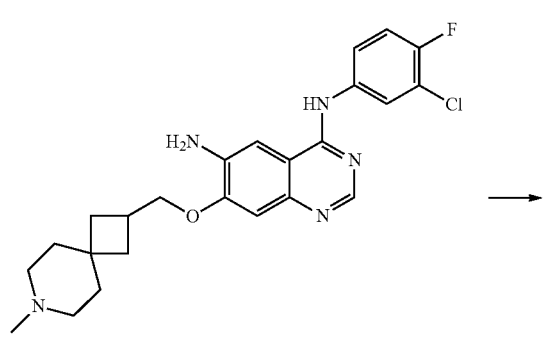

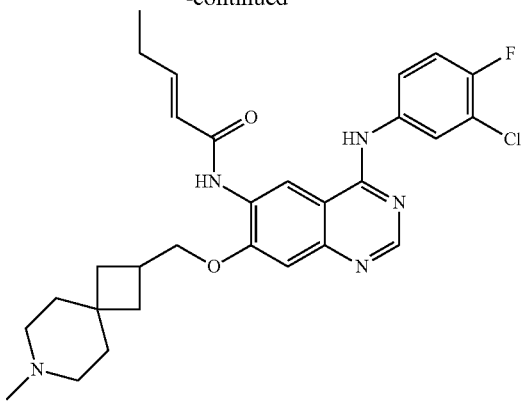

(1) Preparation of N-(4-(3-chloro-4-fluorophenyl))-7-((7-methyl-7-azaspiro[3.5]nonan-2-yl)methoxy)quinazolin-4,6-diamine N-(4-(3-chloro-4-fluorophenyl))-7-((7-methyl-7-azaspiro[3.5]nonan-2-yl)methoxy)quinazolin-4,6-diamine was prepared according to steps (1) and (2) of Example 18.

(2) Preparation of (E)-N-[4-(3-chloro-4-fluorophenylamino)-7-((7-methyl-7-azaspiro[3.5]nonan-2-yl)methoxy)quinazolin-6-yl]-2-pentenamide Trans-2-pentenoic acid (86 mg, 0.86 mmol) was dissolved in DMF (10 mL). Then HATU (425 g, 1.12 mmol), DIEA (333 mg, 2.6 mmol) and N-(4-(3-chloro-4-fluorophenyl))-7-((7-methyl-7-azaspiro[3.5]nonan-2-yl)methoxy)quinazoline-4,6-diamine (300 mg, 0.66 mmol) were added. The mixture was stirred at room temperature for 12 h. After the completion of reaction, water (50 mL) was added. The reaction was extracted with dichloromethane. The organic layer was rotary-evaporated to dryness under a reduced pressure. The resulting residue was purified by a silica gel column chromatography (eluted with dichloromethane/methanol=10/1-5/1) to produce (E)-N-[4-(3-chloro-4-fluorophenylamino)-7-((7-methyl-7-azaspiro[3.5]nonan-2-yl)methoxy)quinazolin-6-yl]-2-pentenamide 30 mg) in a yield of 8%.

(3) Preparation of (E)-N-[4-(3-chloro-4-fluorophenylamino)-7-((7-methyl-7-azaspiro[3.5]nonan-2-yl)methoxy)quinazolin-6-yl]-2-pentenamide (Compound 17) hydrochloride (E)-N-[4-(3-chloro-4-fluorophenylamino)-7-((7-methyl-7-azaspiro[3.5]nonan-2-yl)methoxy)quinazolin-6-yl]-2-pentenamide (58 mg, 0.11 mmol) was dissolved in methanol (10 mL). HCl was added dropwise at room temperature. The reaction was conducted for 2 h under stirring, and then the solvent was evaporated off to produce a yellow solid (E)-N-[4-(3-chloro-4-fluorophenylamino)-7-((7-methyl-7-azaspiro[3.5]nonan-2-yl)methoxy)quinazolin-6-yl]-2-pentenamide hydrochloride 61 mg) in a yield of 100%.

Molecular formula: $C_{29}H_{34}O_2FN_5O_2$

Mass spectrum (m/e): 538.1 (M+1), 269.6 (M/2)

$^1$H NMR (400 MHz, DMSO-d$_6$) δ11.0 (br s, 1H), 9.41 (s, 1H), 9.01 (s, 1H), 8.94 (s, 1H), 8.82 (s, 1H), 7.98 (d, 1H), 7.65 (d, 1H), 7.52 (t, 1H), 7.26 (s, 1H), 5.67 (m, 2H), 4.24 (d, 2H), 3.28 (d, 2H), 2.80 (m, 2H), 2.74 (s, 3H), 1.63-1.98 (m, 14H).

Example 18 Preparation of N-[4-(3-chloro-4-fluorophenylamino)-7-((7-methyl-7-azaspiro[3.5]nonan-2-yl)methoxy)quinazolin-6-yl]-acrylamide (Compound 18)

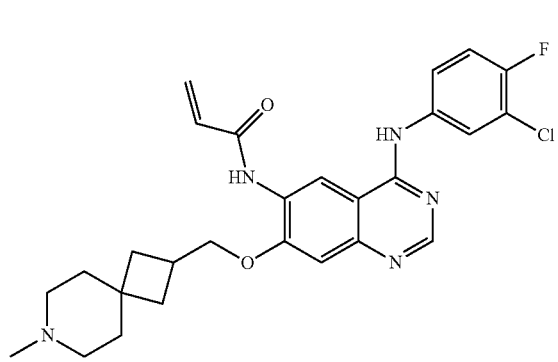 [SMILES: C=CC(=O)Nc1cc2c(Nc3ccc(F)c(Cl)c3)ncnc2cc1OCC1CC2(CCN(C)CC2)C1]

(1) Preparation of N-(4-(3-chloro-4-fluorophenyl))-7-((7-methyl-7-azaspiro[3.5]nonan-2-yl)methoxy)-6-nitroquinazolin-4-amine

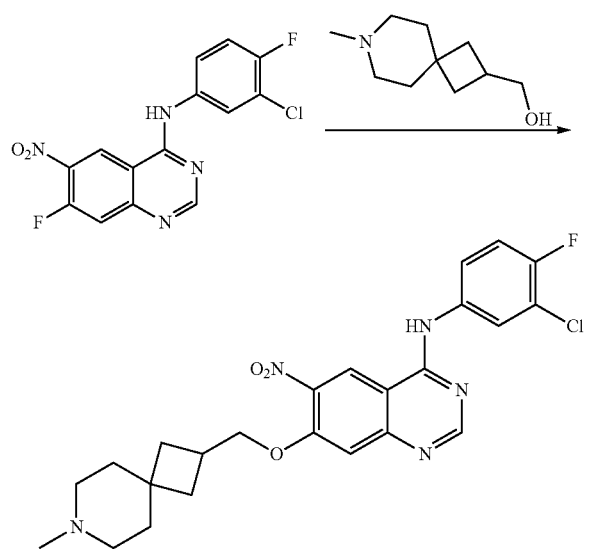

(7-methyl-7-azaspiro[3.5]nonan-2-yl)methanol (9 g, 53 mmol) was dissolved in DMF (20 mL). 60% sodium hydride (10 g, 0.25 mol) was added in batch in an ice bath under an atmosphere of $N_2$. The mixture was moved to an atmosphere of room temperature and stirred for 1 h. N-(4-(3-chloro-4-fluorophenyl))-7-fluoro-6-nitroquinazolin-4-amine (18 g, 53 mmol) was added. The mixture was stirred at room temperature overnight. After the completion of reaction, water (20 mL) was added. The mixture was filtered. The filtered cake was dried in vacuum to produce N-(4-(3-chloro-4-fluorophenyl))-7-((7-methyl-7-azaspiro[3.5]nonan-2-yl)methoxy)-6-nitroquinazolin-4-amine (17 g) in a yield of 66%.

(2) Preparation of N-(4-(3-chloro-4-fluorophenyl))-7-((7-methyl-7-azaspiro[3.5]nonan-2-yl)methoxy)quinazolin-4,6-diamine

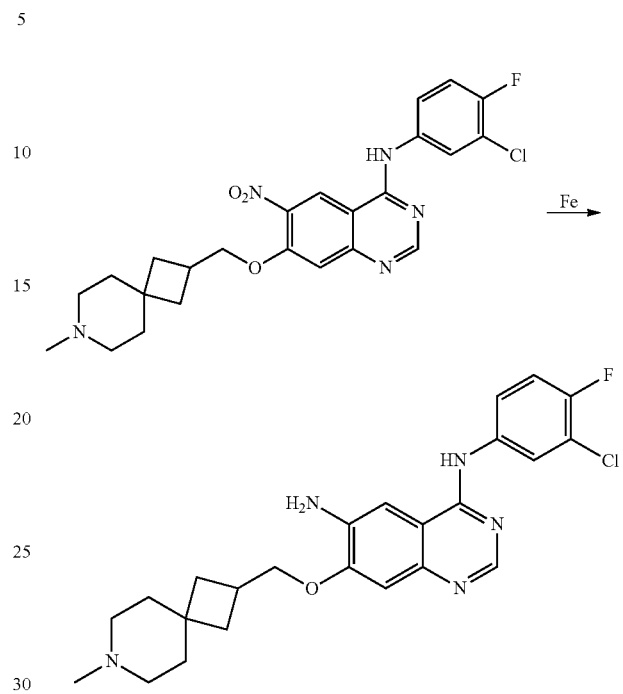

N-(4-(3-chloro-4-fluorophenyl))-7-((7-methyl-7-azaspiro[3.5]nonan-2-yl)methoxy)-6-nitroquinazolin-4-amine (17 g, 35 mmol) was dissolved in a mixed solvent (60 mL) of acetic acid and ethanol ($CH_3COOH/EtOH=1/3$). To the mixture was added Fe powder (13.6 g, 243 mmol). The mixture was stirred at room temperature for 12 h. After the completion of reaction, the mixture was rotary-evaporated under a reduced pressure to remove EtOH. Water (30 mL) was added. The mixture was adjusted with 1 mol/L NaOH solution until it became basic. The mixture was extracted with EA. The organic layer was rotary-evaporated to dryness under a reduce pressure. The resulting residue was purified by a silica gel column chromatography (eluted with dichloromethane/methanol=10/1) to produce N-(4-(3-chloro-4-fluorophenyl))-7-((7-methyl-7-azaspiro[3.5]nonan-2-yl)methoxy)quinazolin-4,6-diamine 10 g) in a yield of 63%.

(3) Preparation of N-[4-(3-chloro-4-fluorophenylamino)-7-((7-methyl-7-azaspiro[3.5]nonan-2-yl)methoxy)quinazolin-6-yl]-acrylamide

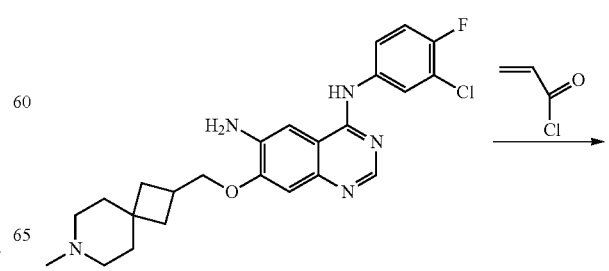

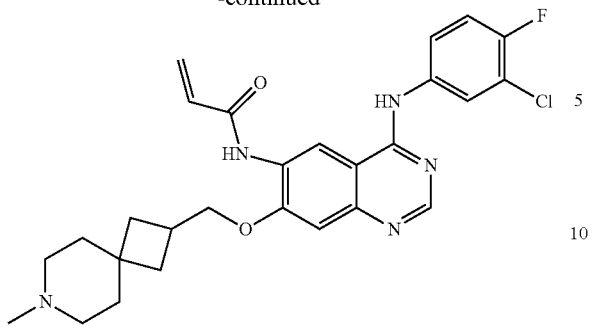

N-(4-(3-chloro-4-fluorophenyl))-7-((7-methyl-7-azaspiro[3.5]nonan-2-yl)methoxy)quinazolin-4,6-diamine (3 g, 6.6 mmol) was dissolved in DCM (10 mL). Triethylamine (2 g, 19.8 mmol) was added. Acryloyl chloride (600 mg, 6.6 mmol) was added dropwise in an ice-water bath. The mixture was stirred at room temperature for 30 min. After the completion of reaction, water (50 mL) was added. The mixture was extracted with EA, and rotary-evaporated to dryness under a reduce pressure. The resulting residue was purified by a silica gel column chromatography (eluted with dichloromethane/methanol=15/1) to produce N-[4-(3-chloro-4-fluorophenylamino)-7-((7-methyl-7-azaspiro[3.5]nonan-2-yl)methoxy)quinazolin-6-yl]-acrylamide (1.26 g) in a yield of 37%.

Molecular formula: $C_{27}H_{29}ClFN_5O_2$

Mass spectrum (m/e): 510.2 (M+1), 255.8 (M/2)

$^1$H NMR (400 MHz, CDCl$_3$) δ9.12 (s, 1H), 8.67 (s, 1H), 8.18 (s, 1H), 7.98 (d, 1H), 7.55 (m, 1H), 7.52 (s, 1H), 7.26 (s, 1H), 7.17 (t, 1H), 6.50 (d, 1H), 6.34 (m, 1H), 5.88 (d, 1H), 4.21 (d, 2H), 2.86 (m, 1H), 2.21-2.50 (m, 7H), 2.07 (t, 2H), 1.82 (m, 2H), 1.63-1.71 (m, 4H).

Example 19 Preparation of N-[4-(3-chloro-4-fluorophenylamino)-7-(2-(7-methyl-7-azaspiro[3.5]nonan-2-yl)ethoxy)quinazolin-6-yl]-acrylamide (Compound 19) and its hydrochloride

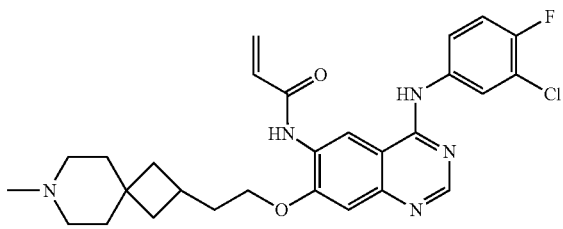 [SMILES: C=CC(=O)Nc1cc2c(Nc3ccc(F)c(Cl)c3)ncnc2cc1OCCC1CC2(CCN(C)CC2)C1]

(1) Preparation of N-(4-(3-chloro-4-fluorophenyl))-7-(2-(7-methyl-7-azaspiro[3.5]nonan-2-yl)ethoxy)-6-nitroquinazolin-4-amine

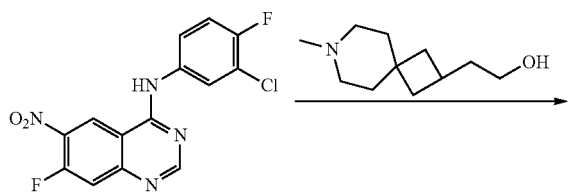

2-(7-methyl-7-azaspiro[3.5]nonan-2-yl)ethanol (2.7 g, 14.8 mmol) was dissolved in DMF (20 mL). 60% sodium hydride (1.78 g, 44.5 mmol) was added in batch in an ice bath under an atmosphere of N$_2$. The mixture was moved to an atmosphere of room temperature and stirred for 1 h. N-(4-(3-chloro-4-fluorophenyl))-7-fluoro-6-nitroquinazolin-4-amine (4.95 g, 14.7 mmol) was added. The mixture was stirred at room temperature overnight. After the completion of reaction, water (20 mL) was added. The mixture was filtered. The filtered cake was dried in vacuum to produce N-(4-(3-chloro-4-fluorophenyl))-7-(2-(7-methyl-7-azaspiro[3.5]nonan-2-yl)ethoxy)-6-nitroquinazolin-4-amine (5.0 g) in a yield of 68%.

(2) Preparation of N-(4-(3-chloro-4-fluorophenyl))-7-(2-(7-methyl-7-azaspiro[3.5]nonan-2-yl)ethoxy)quinazolin-4,6-diamine

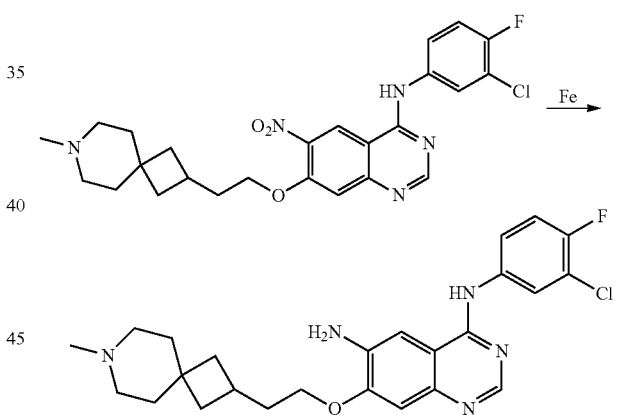

N-(4-(3-chloro-4-fluorophenyl))-7-(2-(7-methyl-7-azaspiro[3.5]nonan-2-yl)ethoxy)-6-nitroquinazolin-4-amine (5 g, 10 mmol) was dissolved in a mixed solvent (250 mL) of acetic acid and ethanol (CH$_3$COOH/EtOH=1/3). To the mixture was added Fe powder (1.96 g, 35 mmol). The mixture was warmed up to 30° C. and stirred for 12 h. After the completion of reaction, the mixture was rotary-evaporated under a reduced pressure to remove EtOH. Water (30 mL) was added. The mixture was adjusted with 1 mol/L NaOH solution until it became basic. The mixture was extracted with EA. The organic layer was rotary-evaporated to dryness under a reduce pressure. The resulting residue was purified by a silica gel column chromatography (eluted with dichloromethane/methanol=10/1) to produce N-(4-(3-chloro-4-fluorophenyl))-7-(2-(7-methyl-7-azaspiro[3.5]nonan-2-yl)ethoxy)quinazolin-4,6-diamine 2.5 g) in a yield of 53%.

(3) Preparation of N-[4-(3-chloro-4-fluorophenylamino)-7-(2-(7-methyl-7-azaspiro[3.5]nonan-2-yl)ethoxy)quinazolin-6-yl]-acrylamide

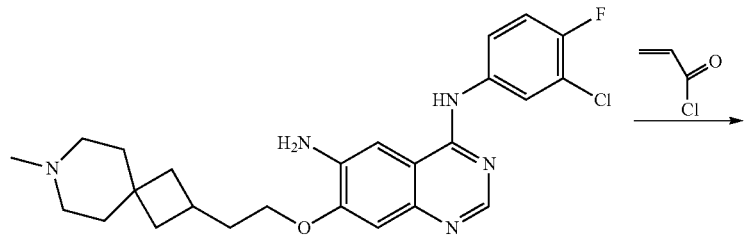

N-(4-(3-chloro-4-fluorophenyl))-7-(2-(7-methyl-7-azaspiro[3.5]nonan-2-yl)ethoxy)quinazolin-4,6-diamine (300 mg, 0.64 mmol) was dissolved in DCM (10 mL). Triethylamine (194 mg, 1.92 mmol) was added. Acryloyl chloride (60 mg, 0.67 mmol) was added dropwise in an ice-water bath. The mixture was stirred at room temperature for 30 min. After the completion of reaction, water (50 mL) was added. The mixture was extracted with EA. The organic layer was rotary-evaporated to dryness under a reduced pressure. The resulting residue was purified by a silica gel column chromatography (eluted with dichloromethane/methanol=15/1) to produce N-[4-(3-chloro-4-fluorophenylamino)-7-(2-(7-methyl-7-azaspiro[3.5]nonan-2-yl)ethoxy)quinazolin-6-yl]-acrylamide 100 mg) in a yield of 30%.

(4) Preparation of N-[4-(3-chloro-4-fluorophenylamino)-7-(2-(7-methyl-7-azaspiro[3.5]nonan-2-yl)ethoxy)quinazolin-6-yl]-acrylamide (Compound 19) hydrochloride N-[4-(3-chloro-4-fluorophenylamino)-7-(2-(7-methyl-7-azaspiro[3.5]nonan-2-yl)ethoxy)quinazolin-6-yl]-acrylamide (100 mg, 0.19 mmol) was dissolved in methanol (10 mL). A HCl gas was introduced under an ice-water bath. The reaction was conducted for 30 min under stirring, and then the solvent was evaporated off to produce a white solid N-[4-(3-chloro-4-fluorophenylamino)-7-(2-(7-methyl-7-azaspiro[3.5]nonan-2-yl)ethoxy)quinazolin-6-yl]-acrylamide hydrochloride (105 mg) in a yield of 97%.

Molecular formula: $C_{28}H_{32}Cl_2FN_5O_2$
Mass spectrum (m/e): 524.0 (M+1), 262.5 (M/2)

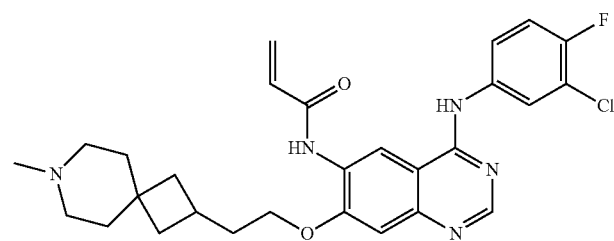

$^1$HNMR (400 MHz, DMSO-$d_6$) δ10.72 (br s, 1H), 9.77 (br s, 1H), 9.73 (s, 1H), 9.00 (s, 1H), 8.75 (s, 1H), 8.03 (d, 1H), 7.52 (d, 1H), 7.49 (t, 1H), 7.36 (s, 1H), 6.73 (m, 1H), 6.30 (d, 1H), 5.83 (m, 1H), 4.18 (t, 2H), 2.81 (m, 1H), 2.77 (m, 1H), 2.68 (s, 3H), 1.52-2.08 (m, 13H).

Example 20 Preparation of (E)-N-(4-(3-chloro-4-fluorophenylamino)-7-((7-methyl-7-azaspiro[3.5]nonan-2-yl)methoxy)quinazolin-6-yl)-4-dimethylamino-2-butenamide (Compound 20)

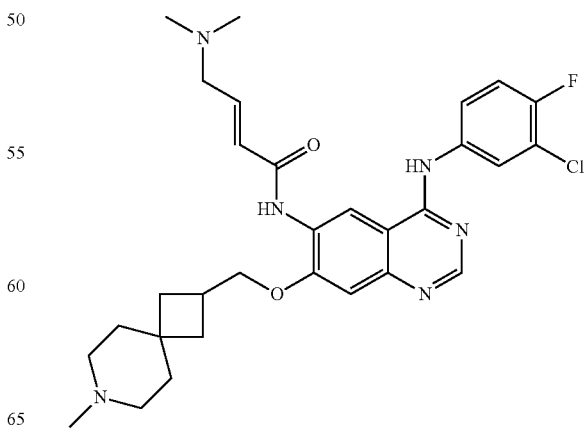

(1) Preparation of (E)-N-(4-(3-chloro-4-fluorophenylamino)-7-((7-methyl-7-azaspiro[3.5]nonan-2-yl)methoxy)quinazolin-6-yl)-4-bromo-2-butenamide

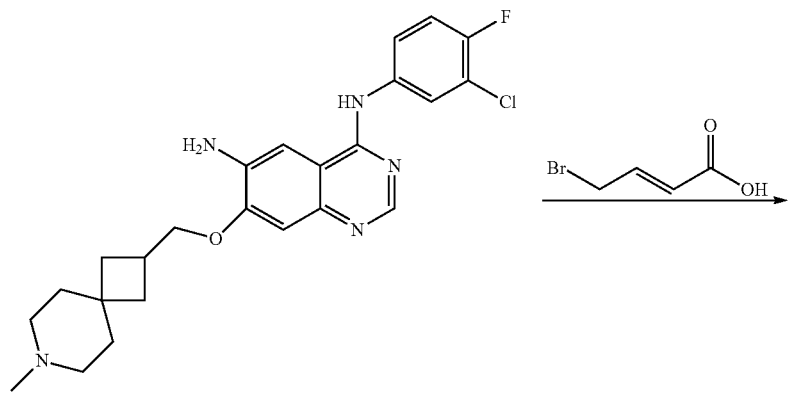

N-(4-(3-chloro-4-fluorophenyl))-7-((7-methyl-7-azaspiro[3.5]nonan-2-yl)methoxy)quinazolin-4,6-diamine was prepared according to steps (1) and (2) of Example 18.

4-bromocrotonic acid (900 mg, 5.5 mmol) was dissolved in THF (10 mL) under nitrogen. DCC (1130 mg, 5.5 mmol) was added under an ice bath. The mixture was stirred for 0.5 h. Then a solution of N-(4-(3-chloro-4-fluorophenyl))-7-((7-methyl-7-azaspiro[3.5]nonan-2-yl)methoxy)quinazolin-4,6-diamine (500 mg, 1.1 mmol) in DMF (10 mL) was added. The mixture was stirred for 40 min, and then a crude product of (E)-N-(4-(3-chloro-4-fluorophenylamino)-7-((7-methyl-7-azaspiro[3.5]nonan-2-yl)methoxy)quinazolin-6-yl)-4-bromo-2-butenamide was obtained. This crude product was directly used in the next step with purification.

(2) Preparation of (E)-N-(4-(3-chloro-4-fluorophenylamino)-7-((7-methyl-7-azaspiro[3.5]nonan-2-yl)methoxy)quinazolin-6-yl)-4-dimethylamino-2-butenamide

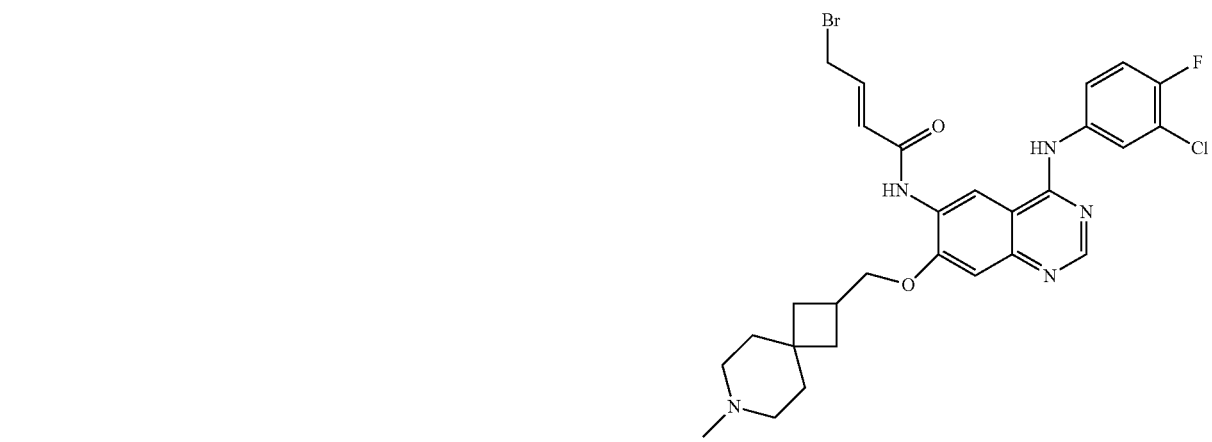

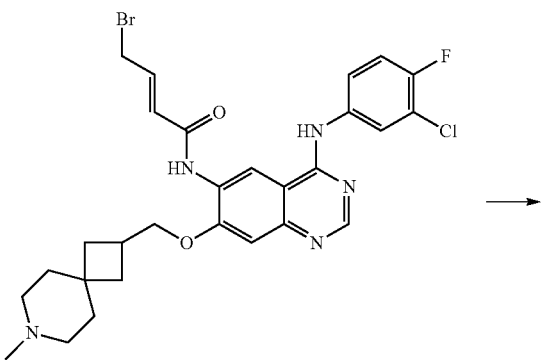

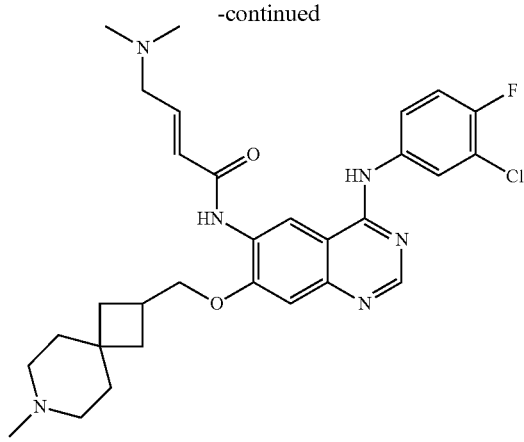

To the product in the previous step, i.e. (E)-N-(4-(3-chloro-4-fluorophenylamino)-7-((7-methyl-7-azaspiro[3.5]nonan-2-yl)methoxy)quinazolin-6-yl)-4-bromo-2-butenamide, were successively added dimethylamine hydrochloride (1.25 g, 15.3 mmol) and DIEA (2.68 mL, 15.4 mmol). The mixture was continuously stirred for 2 h under an ice bath. The mixture was moved to an atmosphere of room temperature and stirred overnight. To the reaction was added a saturated sodium bicarbonate solution. The reaction was extracted with ethyl acetate. The organic layer was dried over anhydrous sodium sulphate and concentrated. Then, the concentrate was separated by a reverse-phase preparative column ($C_{18}$, ODS-AQ 40-60 um, mobile phase: methanol/water=50/50) to produce (E)-N-(4-(3-chloro-4-fluorophenylamino)-7-((7-methyl-7-azaspiro[3.5]nonan-2-yl)methoxy)quinazolin-6-yl)-4-dimethylamino-2-butenamide (120 mg) in a yield of 19.2%.

Molecular formula: $C_{30}H_{36}ClFN_6O_2$

Mass spectrum (m/e): 567 (M+1)

$^1$HNMR (400 MHz, DMSO-$d_6$) δ9.79 (s, 1H), 9.46 (s, 1H), 8.80 (s, 1H), 8.54 (s, 1H), 8.13-8.17 (m, 1H), 7.79-7.83 (m, 1H), 7.39-7.46 (m, 1H), 7.27 (s, 1H), 6.77 (dd, 1H), 6.51 (d, 1H), 4.17 (d, 2H), 3.08 (d, 2H), 2.70-2.82 (m, 1H), 2.21 (m, 10H), 2.11 (s, 3H), 1.88 (t, 2H), 1.71 (t, 2H), 1.22-1.51 (m, 4H).

Example 21 Preparation of (E)-N-[4-(3-chloro-4-fluorophenylamino)-7-((2-(3-methyl-3-aza-bicyclo[3.1.0]-6-hexyl)-ethoxy)quinazolin-6-yl)-4-dimethylamino]-crotonamide (Compound 21)

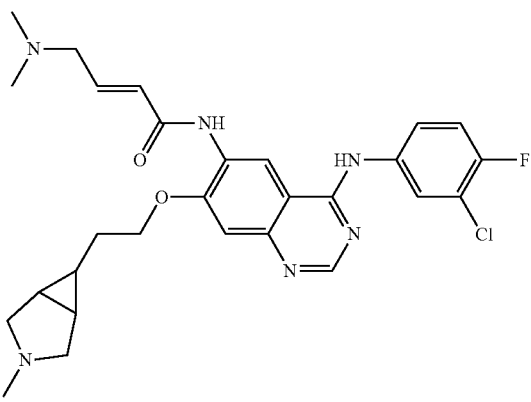 [SMILES: CN(C)C/C=C/C(=O)Nc1cc2c(Nc3ccc(F)c(Cl)c3)ncnc2cc1OCCC1C2CN(C)CC12]

(1) Preparation of N-(4-(3-chloro-4-fluorophenyl))-7-(2-(3-methyl-3-azabicyclo[3.1.0]-6-hexyl)-ethoxy)-6-nitroquinazolin-4-amine

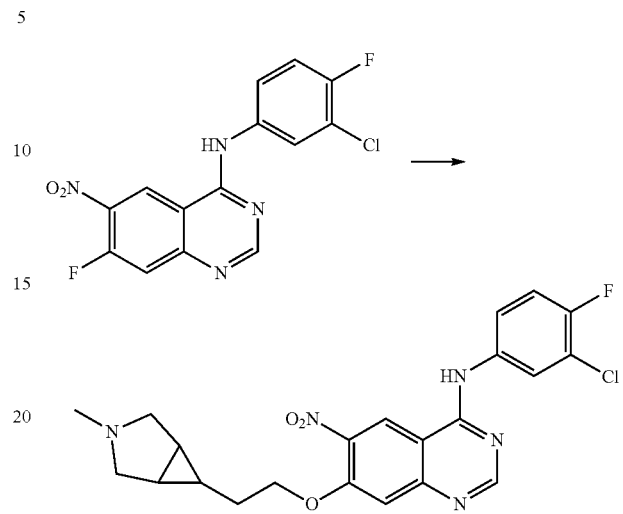

2-(3-methyl-3-aza-bicyclo[3.1.0]-6-hexyl)-ethanol (7.5 g, 53 mmol) was dissolved in DMF (20 mL). 60% sodium hydride (10 g, 0.25 mol) was added in batch in an ice bath under an atmosphere of $N_2$. The mixture was moved to an atmosphere of room temperature and stirred for 1 h. N-(4-(3-chloro-4-fluorophenyl))-7-fluoro-6-nitroquinazolin-4-amine (18 g, 53 mmol) was added. The mixture was stirred at room temperature overnight. After the completion of reaction, water (20 mL) was added. The mixture was filtered. The filtered cake was dried in vacuum to produce N-(4-(3-chloro-4-fluorophenyl))-7-(2-(3-methyl-3-aza-bicyclo[3.1.0]-6-hexyl)-ethoxy)-6-nitroquinazolin-4-amine (14.8 g) in a yield of 61%.

(2) Preparation of N-(4-(3-chloro-4-fluorophenyl))-7-(2-(3-methyl-3-aza-bicyclo[3.1.0]-6-hexyl)-ethoxy)quinazolin-4,6-diamine

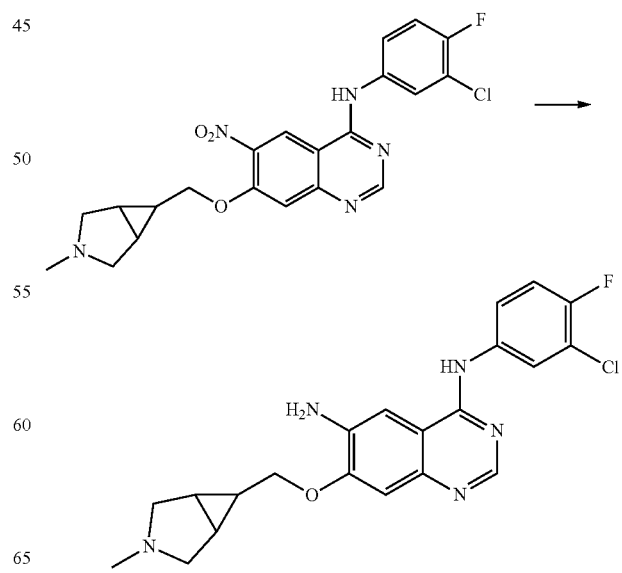

N-(4-(3-chloro-4-fluorophenyl))-7-(2-(3-methyl-3-aza-bicyclo[3.1.0]-6-hexyl)-ethoxy))-6-nitroquinazolin-4-amine (14.8 g, 32 mmol) was dissolved in a mixed solvent (60 mL) of acetic acid and ethanol (CH₃COOH/EtOH=1/3). To the mixture was added Fe powder (13.6 g, 243 mmol). The mixture was stirred at room temperature for 12 h. After the completion of reaction, the rotary-evaporation was conducted to remove EtOH. Water (30 mL) was added. The mixture was adjusted with 1 mol/L NaOH solution until it became basic. The mixture was extracted with EA. The organic layer was rotary-evaporated to dryness under a reduce pressure. The resulting residue was purified by a silica gel column chromatography (eluted with dichloromethane/methanol=10/1) to produce N-(4-(3-chloro-4-fluorophenyl))-7-(2-(3-methyl-3-aza-bicyclo[3.1.0]-6-hexyl)-ethoxy))quinazolin-4,6-diamine (8.3 g) in a yield of 62%.

(3) Preparation of (E)-N-[4-(3-chloro-4-fluorophenylamino)-7-((2-(3-methyl-3-aza-bicyclo[3.1.0]-6-hexyl)-ethoxy)-quinazolin-6-yl-4-chloro)]-crotonamide

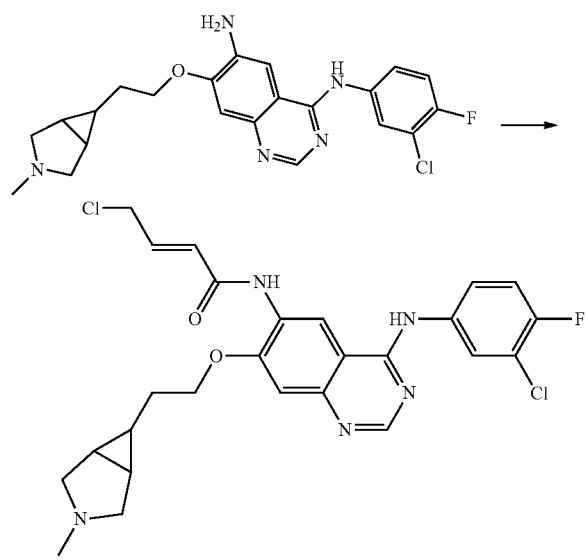

N-(4-(3-chloro-4-fluorophenyl))-7-(2-(3-methyl-3-aza-bicyclo[3.1.0]-6-hexyl)-ethoxy))quinazolin-4,6-diamine (2.73 g, 6.6 mmol) was dissolved in DCM (10 mL). Triethylamine (2 g, 19.8 mmol) was added. (E)-4-chloro-crotonyl chloride (600 mg, 6.6 mmol) was added dropwise in an ice-water bath. The mixture was stirred at room temperature for 30 min. After the completion of reaction, water (50 mL) was added. The mixture was extracted with EA. The organic layer was rotary-evaporated to dryness under a reduce pressure. The resulting residue was purified by a silica gel column chromatography (eluted with dichloromethane/methanol=15/1) to produce (E)-N-[4-(3-chloro-4-fluorophenylamino)-7-((2-(3-methyl-3-aza-bicyclo[3.1.0]-6-hexyl)-ethoxy)-quinazolin-6-yl-4-chloro)]-crotonamide (2.81 g) in a yield of 81%.

(4) Preparation of N-[4-(3-chloro-4-fluorophenylamino)-7-(2-(3-methyl-3-aza-bicyclo[3.1.0]-6-hexyl)-ethoxy)-quinazolin-6-((E)-4-dimethylamino)]-crotonamide

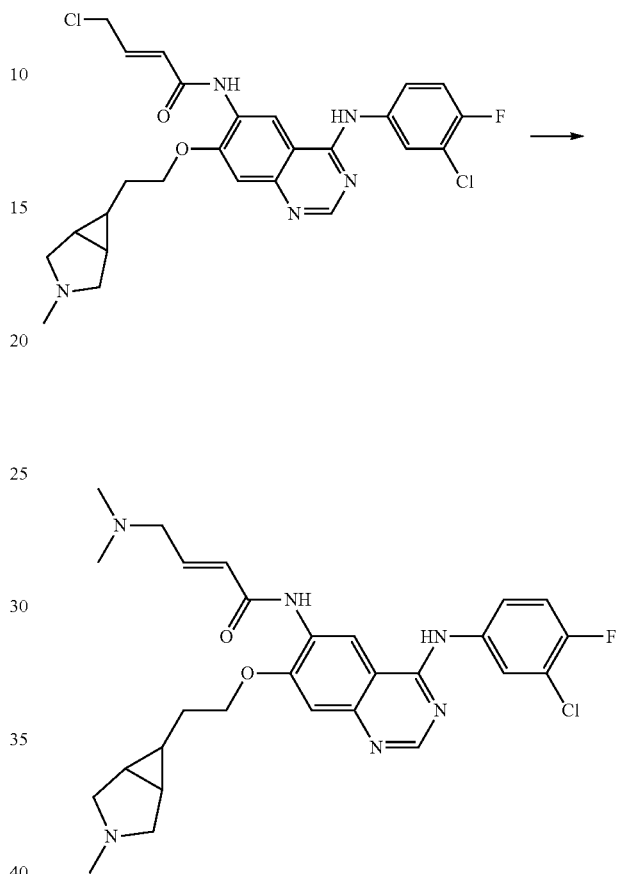

N-[4-(3-chloro-4-fluorophenylamino)-7-(2-(3-methyl-3-aza-bicyclo[3.1.0]-6-hexyl)-ethoxy)-quinazolin-6-((E)-4-chloro)]-crotonamide (0.23 g, 0.4 mmol) was dissolved in acetonitrile (30 mL). Methylamine hydrochloride (0.32 g, 4 mmol) and cesium carbonate (2.6 g, 8 mmol) were added under the nitrogen gas protection. The mixture was heated to reflux and filtered. The filtrate was rotary-evaporated to dryness under a reduce pressure. Then the resulting residue was directly separated by a reverse phase preparative column (C18, ODS-AQ 40-60 um, mobile phase: methanol/water=50/50) to produce a compound named (E)-N-[4-(3-chloro-4-fluorophenylamino)-7-((2-(3-methyl-3-aza-bicyclo[3.1.0]-6-hexyl)-ethoxy)quinazolin-6-yl)-4-dimethylamino]-crotonamide (0.14 g) in a yield of 37%.

Molecular formula: $C_{28}H_{32}ClFN_6O_2$

Mass spectrum (m/e): 539.2 (M+1), 270 (M/2)

¹HNMR (400 MHz, CD₃OD) δ 9.20 (s, 1H), 8.76 (s, 1H), 7.94 (d, 1H), 7.68-7.64 (m, 1H), 7.40-7.35 (m, 2H), 7.11-7.00 (m, 2H), 4.44-4.41 (m, 2H), 4.08 (d, 2H), 3.73 (d, 2H), 3.36 (s, 4H), 3.00-2.67 (m, 8H), 1.96-1.92 (m, 2H), 1.82-1.75 (m, 3H).

Example 22 Preparation of (E)-N-[4-(3-chloro-4-fluorophenylamino)-7-(((spiro[3.5]octan-2-yl)methoxy)quinazolin-6-yl)-4-dimethylamino]-crotonamide (Compound 22)

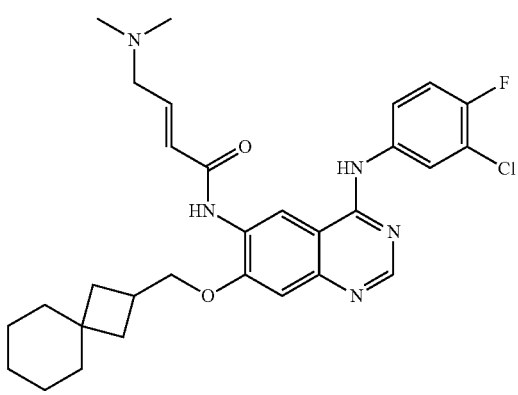 [SMILES: CN(C)C/C=C/C(=O)Nc1cc2c(Nc3ccc(F)c(Cl)c3)ncnc2cc1OCC1CC2(CCCCC2)C1]

(1) Preparation of N-(4-(3-chloro-4-fluorophenyl))-7-((spiro[3.5]octan-2-yl)methoxy)-6-nitroquinazolin-4-amine

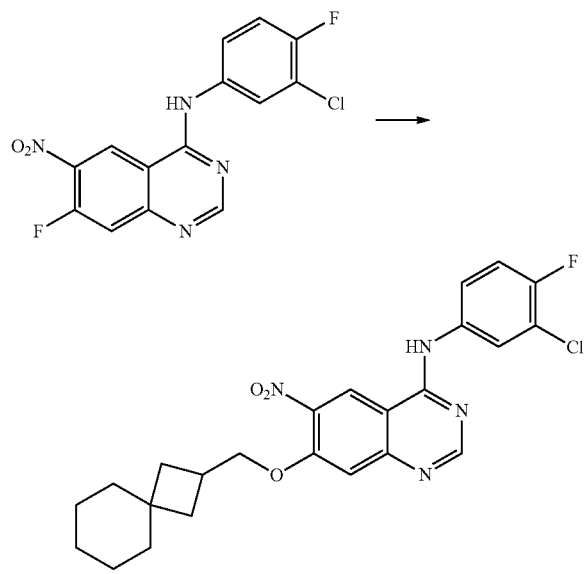

(Spiro[3.5]octan-2-yl)methanol (8.16 g, 53 mmol) was dissolved in DMF (20 mL). 60% sodium hydride (10 g, 0.25 mol) was added in batch in an ice bath under an atmosphere of $N_2$. The mixture was moved to an atmosphere of room temperature and stirred for 1 h. N-(4-(3-chloro-4-fluorophenyl))-7-fluoro-6-nitroquinazolin-4-amine (18 g, 53 mmol) was added. The mixture was stirred at room temperature overnight. After the completion of reaction, water (20 ml) was added. The mixture was filtered. The filtered cake was dried in vacuum to produce N-(4-(3-chloro-4-fluorophenyl))-7-((spiro[3.5]octan-2-yl)methoxy)-6-nitroquinazolin-4-amine (18.68 g) in a yield of 75%.

(2) Preparation of N-(4-(3-chloro-4-fluorophenyl))-7-((spiro[3.5]octan-2-yl)methoxy)-quinazolin-4,6-diamine

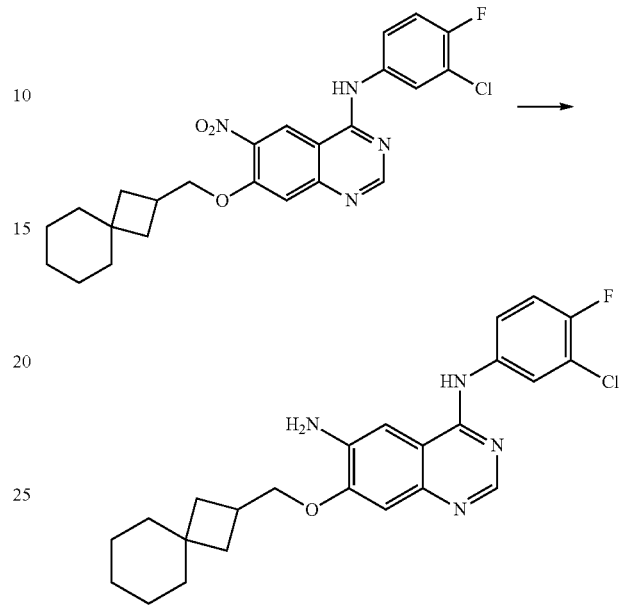

N-(4-(3-chloro-4-fluorophenyl))-7-((spiro[3.5]octan-2-yl)methoxy)-6-nitroquinazolin-4-amine (16.45 g, 35 mmol) was dissolved in a mixed solvent (60 mL) of acetic acid and ethanol ($CH_3COOH/EtOH=1/3$). To the mixture was added Fe powder (13.6 g, 243 mmol). The mixture was stirred at room temperature for 12 h. After the completion of reaction, the mixture was rotary-evaporated under a reduced pressure to remove EtOH. Water (30 mL) was added. The mixture was adjusted with 1 mol/L NaOH solution until it became basic. The mixture was extracted with EA. The organic layer was rotary-evaporated to dryness under a reduce pressure. The resulting residue was purified by a silica gel column chromatography (dichloromethane/methanol=10/1, V/V) to produce N-(4-(3-chloro-4-fluorophenyl))-7-((spiro[3.5]octan-2-yl)methoxy)quinazolin-4,6-diamine (10 g) in a yield of 63%.

(3) Preparation of ((E)-4-dimethylamino)-crotonyl chloride hydrochloride

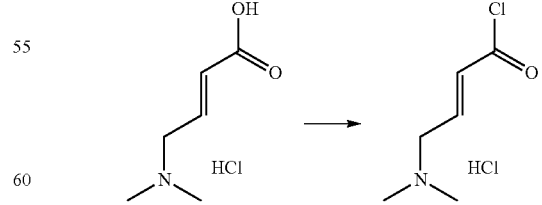

((E)-4-dimethylamino)-crotonic acid hydrochloride (1.65 g, 10 mmol) was dissolved in THF (50 ml). DMF (0.1 mL) was added. The mixture was cooled to 0° C., and $SOCl_2$ (5 mL) was slowly added dropwise. The reaction was warmed up to room temperature. After 0.5 h, the mixture was heated to reflux, stirred for 3 h under reflux, then cooled down to room temperature, and evaporated off the excess of SOCl₂ under the nitrogen gas protection. The resulting product was directly used in the next step.

(4) Preparation of (E)-N-[4-(3-chloro-4-fluorophenylamino)-7-(((spiro[3.5]octan-2-yl)methoxy)quinazolin-6-yl)-4-dimethylamino]-crotonamide

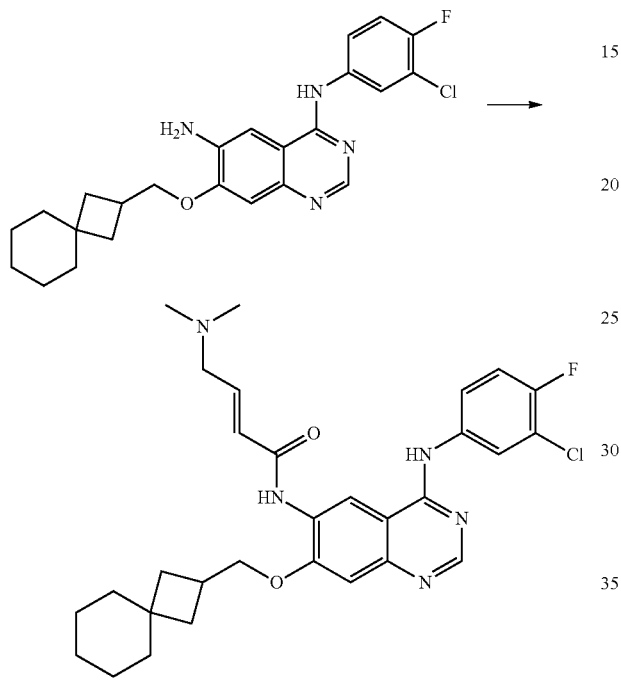

N-(4-(3-chloro-4-fluorophenyl))-7-((spiro[3.5]octan-2-yl)methoxy)quinazolin-4,6-diamine (3 g, 6.6 mmol) was dissolved in DCM (10 mL). Triethylamine (2 g, 19.8 mmol) was added. 6-((E)-4-dimethylamino)]-crotonyl chloride (600 mg, 6.6 mmol) was added dropwise in an ice-water bath. The mixture was stirred at room temperature for 30 min. After the completion of reaction, water (50 mL) was added. The mixture was extracted with EA. The organic layer was rotary-evaporated to dryness under a reduced pressure. The resulting residue was purified by a silica gel column chromatography (eluted with dichloromethane/methanol=15/1) to produce (E)-N-[4-(3-chloro-4-fluorophenylamino)-7-(((spiro[3.5]octan-2-yl)methoxy)quinazolin-6-yl)-4-dimethylamino]-crotonamide (1.26 g) in a yield of 38%.

Molecular formula: $C_{30}H_{35}ClFN_5O_2$

Mass spectrum (m/e): 552.2 (M+1), 256.2 (M/2)

¹HNMR (400 MHz, CD₃OD) δ 9.21 (s, 1H), 8.79 (s, 1H), 7.96 (d, 1H), 7.69-7.68 (m, 1H), 7.42 (d, 1H), 7.34 (s, 1H), 7.04 (t, 1H), 6.84 (d, 1H), 4.37 (d, 2H), 4.09 (d, 2H), 3.0-2.96 (m, 7H), 2.10-2.05 (m, 5H), 1.77-1.63 (m, 7H), 1.37-1.33 (m, 3H).

Example 23 Preparation of (E)-N-(7-(bicyclo[3.1.0]hexan-6-ylmethoxy)-4-(3-chloro-4-fluorophenylamino)quinazolin-6-yl)-4-(dimethylamino)but-2-enamide (Compound 23)

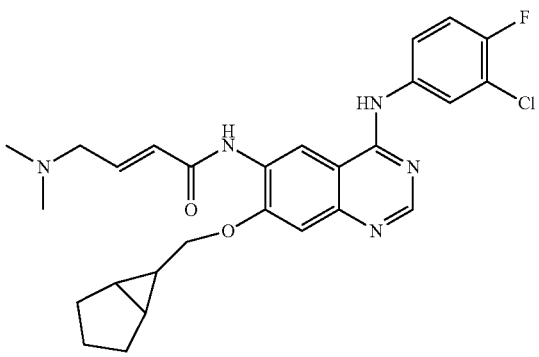 [SMILES: CN(C)C/C=C/C(=O)Nc1cc2c(Nc3ccc(F)c(Cl)c3)ncnc2cc1OCC1C2CCCC21]

(1) Preparation of 7-(bicyclo[3.1.0]hexan-6-ylmethoxy)-N-(4-(3-chloro-4-fluorophenyl))-6-nitroquinazolin-4-amine

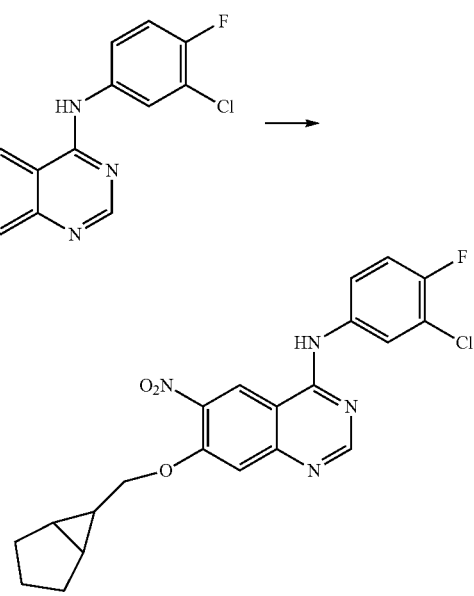

To dioxane (50 ml) were added bicyclo[3.1.0]hexan-6-ylmethanol (3.36 g, 30 mmol), potassium carbonate (4.14 g, 30 mmol) and 7-fluoro-4-(3-chloro-4-fluorophenylamine)-6-nitroquinazoline (3.36 g, 10 mmol). The mixture was stirred at room temperature for 24 hr. After the completion of reaction, water was added. The mixture was extracted with ethyl acetate. The organic layer was dried over anhydrous sodium sulphate. The resulting residue was purified with a silica gel column chromatography (petroleum ether/ethyl acetate=1/1) to produce a product (7.57 g) in a yield of 59%.

91

(2) Preparation of 7-(bicyclo[3.1.0]hexan-6-yl-methoxy)-N-(4-(3-chloro-4-fluorophenyl))quinazolin-4,6-diamine

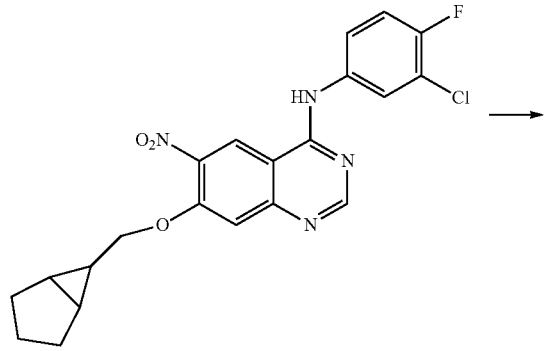

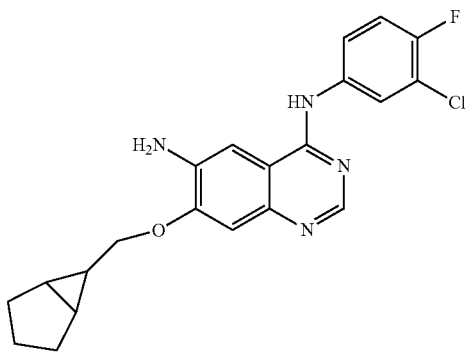

7-(bicyclo[3.1.0]hexan-6-ylmethoxy)-N-(4-(3-chloro-4-fluorophenyl))-6-nitroquinazolin-4-amine (1.71 g, 4 mmol) and Pd/C (0.2 g) were added to tetrahydrofuran (30 mL). The mixture was stirred at room temperature overnight. After the completion of reaction, water was added. The mixture was extracted with ethyl acetate. The organic layer was evaporated to dryness to produce a product (1.40 g) in a yield of 88%.

92

(3) Preparation of (E)-N-(7-(bicyclo[3.1.0]hexan-6-ylmethoxy)-4-(3-chloro-4-fluorophenylamino)quinazolin-6-yl)-4-(dimethylamino)but-2-enamide

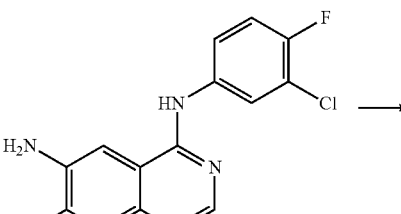

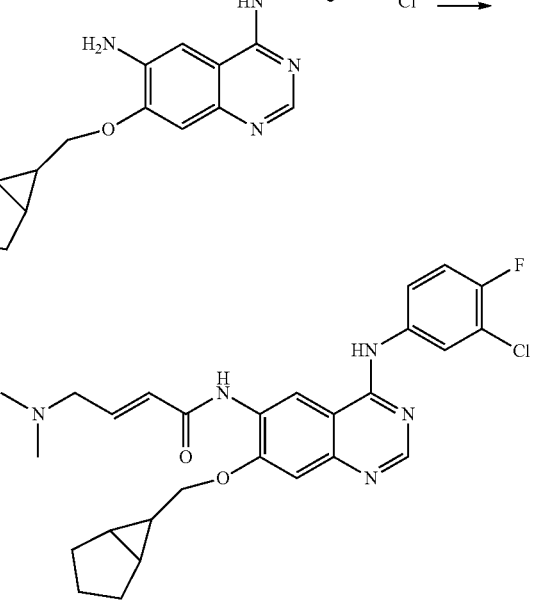

4-(dimethylamino)but-2-enoic acid (0.52 g, 4 mmol) was added to dichloroethane (20 mL). Thionyl chloride (0.95 g, 8 mmol) was added dropwise under an ice bath. The mixture was heated to reflux for 2 hr. After the completion of reaction, the reaction was evaporated to dryness. The resulting residue was dissolved in acetonitrile (50 mL). A solution of triethylamine (0.3 g, 3 mmol) and 7-(bicyclo[3.1.0]hexan-6-ylmethoxy)-N-(4-(3-chloro-4-fluorophenyl)quinazolin-4,6-diamine (1.19 g, 3 mmol) in tetrahydrofuran (100 mL) was added dropwise. The mixture was stirred for 12 hr, and water was added. The reaction was extracted with dichloromethane. The organic layer was dried over anhydrous sodium sulphate. The resulting residue was purified by a preparative liquid chromatography ($C_{18}$, ODS-AQ 40-60 um, mobile phase: methanol/water=50/50) to produce (E)-N-(7-(bicyclo[3.1.0]hexan-6-ylmethoxy)-4-(3-chloro-4-fluorophenylamino)quinazolin-6-yl)-4-(dimethylamino)but-2-enamide (0.168 g) in a yield of 11%.

Molecular formula: $C_{27}H_{29}ClFN_5O_2$

Mass spectrum (m/e): 510 (M+1), 255.7 (M/2)

$^1$HNMR (400 MHz, DMSO-$d_6$) δ 9.78 (s, 1H), 951-9.54 (m, 1H), 8.86 (s, 1H), 8.51-8.52 (m, 1H), 8.11-8.13 (m, 1H), 7.78-7.80 (m, 1H), 7.41 (t, 1H), 7.23 (s, 1H), 6.77-6.81 (m, 1H), 6.54-6.57 (m, 1H), 4.21-4.23 (m, 1H), 4.05-4.07 (m, 1H), 3.08-3.09 (m, 2H), 2.19 (s, 6H), 1.95-2.01 (m, 1H), 1.83-1.91 (m, 2H), 1.88 (m, 2H), 1.71-1.73 (m, 2H), 1.36 (m, 1H), 1.04 (m, 1H).

Compounds 1-16, 18 and 20-23 can be prepared into salts according to the salt-formation methods described for Compound 17 and Compound 19.

The following compounds can also be prepared according to the above-mentioned methods.

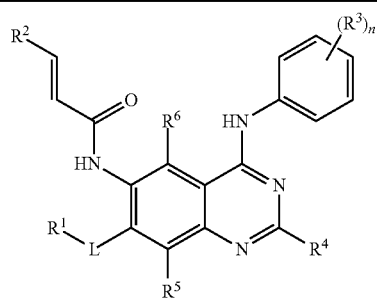
| No. | R¹ | R² | (R³)n | L |
|-----|-----|-----|-------|---|
| 24 | | H | 3'-Cl, 4'-F | O |
| 25 | | H | 3'-Cl, 4'-F | O |
| 26 | | H | 3'-Cl, 4'-F | O |
| 27 | | H | 3'-Cl, 4'-F | O |
| 28 | | H | 3'-Cl, 4'-F | O |
| 29 | | H | 3'-Cl, 4'-F | O |
| 30 | | H | 3'-Cl, 4'-F | O |
| 31 | | —CH₂CH₃ | 3'-Cl, 4'-F | O |

-continued

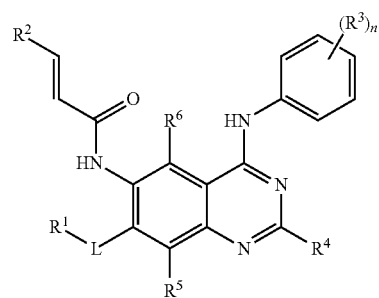

| No. | R¹ | R² | (R³)n | L |
|---|---|---|---|---|
| 32 | (2-methyl-2-azaspiro[3.5]nonyl-ethyl) | —CH$_2$CH$_3$ | 3'-Cl, 4'-F | O |
| 33 | (2-methyl-2-azaspiro[3.5]nonyl-ethyl) | —CH$_2$N(CH$_3$)$_2$ | 3'-Cl, 4'-F | O |
| 34 | (2-methyl-2-azaspiro[3.5]nonyl-ethyl) | —CH$_2$OCH$_3$ | 3'-Cl, 4'-F | O |
| 35 | (1-oxa-8-azaspiro[4.5]decyl-ethyl) | —CH$_3$ | 3'-Cl, 4'-F | O |
| 36 | (1-oxa-8-azaspiro[4.5]decyl-ethyl) | —CH$_3$ | 3'-Cl, 4'-F | O |
| 37 | (3-azabicyclo[3.1.0]hexyl-ethyl) | —CH$_2$-piperidinyl | 3'-Cl, 4'-F | O |
| 38 | (1-oxa-8-azaspiro[4.5]decyl-ethyl) | —CH$_2$N(CH$_3$)$_2$ | 3'-Cl, 4'-F | O |
| 39 | (1-oxa-8-azaspiro[4.5]decyl-ethyl) | —CH$_2$N(CH$_3$)$_2$ | 3'-Cl, 4'-F | O |

-continued

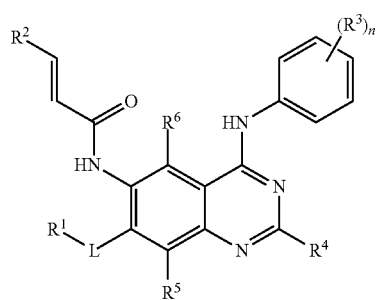

| No. | R¹ | R² | (R³)n | L |
|---|---|---|---|---|
| 40 | [2-ethyl-2-azaspiro[3.5]... piperidine-CH₂-] | H₃C-O-CH₂CH₂- | 3'-Cl, 4'-F | O |
| 41 | [azabicyclic-CH₂-] | H₃C-O-CH₂CH₂- | 3'-Cl, 4'-F | O |
| 42 | [decahydronaphthyl-NHCH₃-CH₂-] | (CH₃)₂N-CH₂- | 3'-Cl, 4'-F | O |
| 43 | [spiro[2.4]heptyl-] | (H₃CCH₂)₂N-CH₂- | 3'-Cl, 4'-F | O |
| 44 | [N-methyl bicyclic pyrrolidine-CH₂-] | (H₃CCH₂)₂N-CH₂- | 3'-Cl, 4'-F | O |
| 45 | [oxabicyclic-] | (H₃CCH₂)₂N-CH₂- | 3'-Cl, 4'-F | O |
| 46 | [2-ethyl-2-azaspiro[3.5]... piperidine-CH₂-] | cyclopropyl-CH₂- | 3'-Cl, 4'-F | O |
| 47 | [N-methyl octahydropyrrolo[3,4-c]pyrrole-] | cyclopropyl-CH₂- | 3'-Cl, 4'-F | O |
| 48 | [N-ethyl diazabicyclic-CH₂-] | cyclopropyl-CH₂- | 3'-Cl, 4'-F | O |

-continued

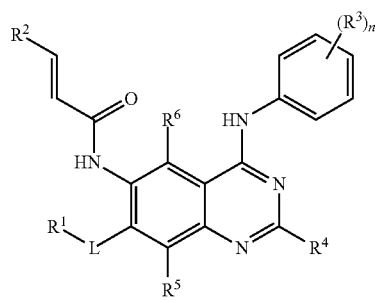

| No. | R¹ | R² | (R³)n | L |
|---|---|---|---|---|
| 49 | piperidine-pyrrolidine spiro with N-CH₃ | cyclopentylmethyl | 3'-Cl, 4'-F | O |
| 50 | 2-oxabicyclic | furan-2-yl methyl | 3'-Cl, 4'-F | O |
| 51 | azabicyclo[2.2.1] methyl | pyrrol-2-yl methyl | 3'-Cl, 4'-F | O |
| 52 | diazabicyclic with N-CH₂CH₃ | thiazol-2-yl methyl | 3'-Cl, 4'-F | O |
| 53 | 2-oxabicyclo[2.2.2]octyl | pyridin-3-yl methyl | 3'-Cl, 4'-F | O |
| 54 | spiro[3.4] dione | pyrimidin-5-yl methyl | 3'-Cl, 4'-F | O |
| 55 | 3-methyl-3-azabicyclo[3.1.0]hexyl | morpholinomethyl | 3'-Cl, 4'-F | O |
| 56 | 3-methyl-3-azabicyclo[3.1.0]hexyl | piperidin-1-yl methyl | 3'-Cl, 4'-F | O |

-continued

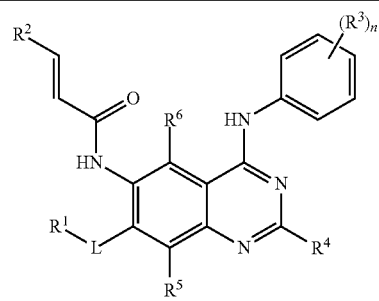

| No. | R¹ | R² | (R³)n | L |
|-----|----|----|-------|---|
| 57 | (bicyclic thiaheterocycle) | (morpholinomethyl) | 3'-Cl, 4'-F | S |
| 58 | (N-methyl octahydrocyclopenta[c]pyrrole) | (morpholinomethyl) | 3'-Cl, 4'-F | O |
| 59 | (N-methyl octahydrocyclopenta[c]pyrrole) | (piperidinomethyl) | 3'-Cl, 4'-F | S |
| 60 | (N-methyl octahydrocyclopenta[c]pyrrole) | (piperidinomethyl) | 3'-Cl, 4'-F | O |
| 61 | (bicyclic sulfone) | (morpholinomethyl) | 3'-Cl, 4'-F | O |
| 62 | (decahydronaphthalenyl-N-methylamino) | (piperidinomethyl) | 3'-Cl, 4'-F | NH |
| 63 | (spiro[2.4]heptanyl) | (morpholinomethyl) | 3'-Cl, 4'-F | NH |
| 64 | (spiro dione) | (morpholinomethyl) | 3'-Cl, 4'-F | O |
| 65 | (N-ethyl spiro azaspiro) | (morpholinomethyl) | 3'-Cl, 4'-F | O |

-continued

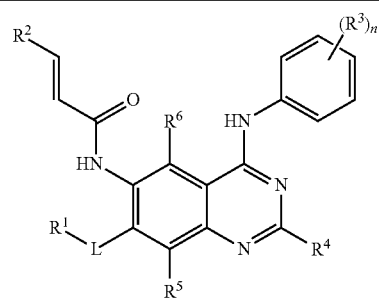

| No. | R¹ | R² | (R³)n | L |
|---|---|---|---|---|
| 66 | (2-spiro[3.5]azaspiro with N-ethyl) | piperidinyl-CH₂ | 3'-Cl, 4'-F | O |
| 67 | (2-spiro[3.5]azaspiro with N-methyl, CH₂ linker) | morpholinyl-CH₂ | 3'-Cl, 4'-F | O |
| 68 | (diazaspiro with N-CH₃) | morpholinyl-CH₂ | 3'-Cl, 4'-F | O |
| 69 | (oxabicyclic) | morpholinyl-CH₂ | 3'-Cl, 4'-F | O |
| 70 | (oxabicyclic) | piperidinyl-CH₂ | 3'-Cl, 4'-F | O |
| 71 | (azabicyclic-CH₂) | morpholinyl-CH₂ | 3'-Cl, 4'-F | O |
| 72 | (diazabicyclic with N-ethyl) | morpholinyl-CH₂ | 3'-Cl, 4'-F | O |
| 73 | (diazabicyclic with N-ethyl) | piperidinyl-CH₂ | 3'-Cl, 4'-F | S |
| 74 | (oxabicyclic) | piperidinyl-CH₂ | 3'-Cl, 4'-F | O |

-continued

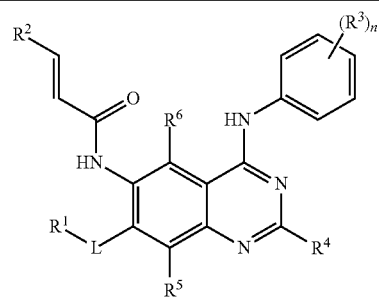

| No. | R¹ | R² | (R³)n | L |
|---|---|---|---|---|
| 75 | [1-methyl-azabicyclo-CH₂-] | [morpholine-CH₂-] | 3'-Cl, 4'-F | O |
| 76 | [1-methyl-azabicyclo-CH₂-] | [piperidine-CH₂-] | 3'-Cl, 4'-F | O |
| 77 | [N-methyl bicyclic pyrrolidine] | [piperazine-CH₂-] | 3'-Cl, 4'-F | O |
| 78 | [N-methyl octahydrocyclopenta[c]pyrrole] | [piperazine-CH₂-] | 3'-Cl, 4'-F | O |
| 79 | [spiro cyclobutane-N-ethyl piperidine] | [pyrrolidine-CH₂-] | 3'-Cl, 4'-F | O |
| 80 | [oxabicyclic] | [piperazine-CH₂-] | 3'-Cl, 4'-F | NH |
| 81 | [N-ethyl diazabicyclo] | [pyrrolidine-CH₂-] | 3'-Cl, 4'-F | S |
| 82 | [oxabicyclo] | [pyrrolidine-CH₂-] | 3'-Cl, 4'-F | S |
| 83 | [1-methyl-azabicyclo-CH₂-] | [piperazine-CH₂-] | 3'-Cl, 4'-F | O |
| 84 | [N-methyl octahydrocyclopenta[c]pyrrole] | [N-methyl-piperazine-CH₂-] | 3'-Cl, 4'-F | O |

-continued

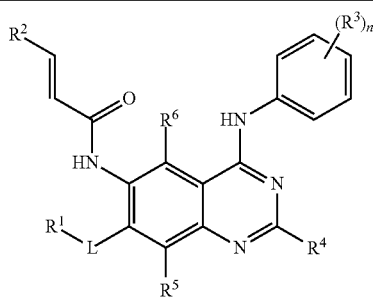

| No. | R¹ | R² | (R³)n | L |
|---|---|---|---|---|
| 85 | (oxabicyclic) | H₃C-N(piperazine)-N- | 3'-Cl, 4'-F | O |
| 86 | (oxabicyclic) | H₃C-O-N(piperazine)-N- | 3'-Cl, 4'-F | O |
| 87 | (N-CH₃ bicyclic pyrrolidine) | (3-fluoromorpholine)-N- | 3'-Cl, 4'-F | O |
| 88 | (oxabicyclic) | (3-dimethylaminopiperidine)-N- with H₃C-N-CH₃ | 3'-Cl, 4'-F | O |
| 89 | (oxabicyclic) | (cyclopentyl-O-CF₃) | 3'-Cl, 4'-F | O |

II. IN VITRO ASSAYS FOR THE ANTINEOPLASTIC ACTIVITIES OF THE PRESENT COMPOUNDS

Hereinafter, the beneficial effects of the present compounds will be illustrated by in vitro enzyme inhibitory activity and in vitro cellular inhibitory activity. However, it should be noted that the beneficial effects of the present compounds are not limited to the effects as illustrated below.

Assay 1
In Vitro Enzyme Inhibitory Activity of the Present Compounds
Samples:
Controls: Gefitinib, erlotinib hydrochloride, purchased from Anqing worldchem Co., LTD.; lapatinib ditosylate, purchased from Taizhou Xingcheng Chempharm Co., Ltd.; CI-1033 hydrochloride, purchased from Shanghai hanxiangchem, Co., Ltd.; and The present compounds: lab-made, their chemical names and structural formulae are shown in the preparation examples.
Assay Procedures:
The abbreviations used in the following assay have the following meanings:
HEPES: hydroxyethyl piperazine ethanesulfonic acid;
Brij-35: polyoxyethylene lauryl ether;
DTT: dithiothreitol;
Coating Reagent #3: #3 coating agent;
EDTA: ethylene diamine tetraacetic acid, purchased from Sigma Co. Ltd.;
FAM labeled peptide: fluorescein labeled peptide 22 (GL Biochem);
ATP: adenosine triphosphate (Sigma);
DMSO: dimethyl sulfoxide;
EGFR: human epidermal growth factor receptor (Carna);

HER2: human epidermal growth factor receptor 2 (Carna);
HER4: human epidermal growth factor receptor 4 (Carna).
1. Formulating the agents to be used in the assay
(1) 1.25-fold MnCl$_2$-free kinase buffer (62.5 mM HEPES, PH 7.5, 0.001875% Brij-35, 12.5 mM MgCl$_2$, 2.5 mM DTT);
(2) 1.25-fold MnCl$_2$-containing kinase buffer (62.5 mM HEPES, pH 7.5, 0.001875% Brij-35, 12.5 mM MgCl$_2$, 12.5 mM MnCl$_2$, 2.5 mM DTT);
(3) Stop buffer (100 mM HEPES, pH 7.5, 0.015% Brij-35, 0.2% Coating Reagent #3, 50 mM EDTA);
(4) 2.5-fold kinase solutions (to the 1.25-fold kinase buffers were added the corresponding kinases to formulate 2.5-fold EGFR, HER2, HER4 kinase solutions);
(5) 2.5-fold peptide solutions (to the 1.25-fold kinase buffers were added FAM labeled peptide and ATP to formulate the peptide solutions);
(6) 5-fold compound solutions (using 100% DMSO to formulate 50-fold compound solutions having different concentration gradients, and diluting with water by 10 times to obtain 5-fold compound solutions having different concentration gradients);
2. Adding 5 μL of a 5-fold compound solution to a 384-well plate;
3. Adding 10 μL of a 2.5-fold kinase solution to incubate for 10 min;
4. Then adding 10 μL of a 2.5-fold peptide solution, and reacting at 28° C. for 1 h; and
5. Finally, adding 25 μL of stop buffer to terminate the reaction, and reading the data with Caliper.
6. Curve fitting to obtain an IC$_{50}$ value.

The calculated inhibition ratio (%)=(the maximum conversion rate–the conversion rate)/(the maximum conversion rate–the minimum conversion rate)×100

The curve fitting was conducted with the Xlfit software to obtain IC$_{50}$ values.
The results are shown below.

TABLE 1

In vitro enzyme inhibitory activity

| Compound | Enzyme inhibitory activity IC$_{50}$ (nM) | | |
| --- | --- | --- | --- |
| | EGFR | HER2 | HER4 |
| Gefitinib | 1.6 | 318 | 7.6 |
| Erlotinib hydrochloride | 1.3 | 454 | 49 |
| Lapatinib ditosylate | 16 | 4.0 | 250 |
| CI-1033 hydrochloride | 0.46 | 4 | 2.2 |
| Compound 6 | 1 | 7.1 | 1.4 |
| Compound 7 | 0.93 | 4.3 | 1.7 |
| Compound 8 | 0.66 | 6.5 | 3.4 |
| Compound 11 | 0.8 | 12 | 8.3 |
| Compound 14 | 0.39 | 2.6 | 1.2 |
| Compound 18 | 1 | 6.5 | 1.9 |
| Compound 19 hydrochloride | 0.56 | 3.1 | 3.7 |

Conclusion:
It can be seen from table 1 that the present compounds have stronger inhibitory activities on EGFR, HER2, HER4 kinases, and are comparable with CI-1033 hydrochloride in activity; the present compounds have a remarkably better inhibitory activity on the HER2 kinase than gefitinib and erlotinib hydrochloride; and the present compounds have a remarkably better inhibitory activity on the HER4 kinase than erlotinib hydrochloride and lapatinib ditosylate.

Assay 2
In Vitro Cellular Inhibitory Activity of the Present Invention
Samples:
Controls: Gefitinib, erlotinib hydrochloride, purchased from Anqing worldchem Co., LTD. Anqing worldchem Co., LTD.; lapatinib ditosylate, purchased from Taizhou Xingcheng Chempharm Co., Ltd.; CI-1033 hydrochloride, purchased from Shanghai hanxiangchem, Co., Ltd.; and
The present compounds: lab-made, their chemical names and structural formulae are shown in the preparation examples.
Assay Procedures:
The abbreviations used in the following assay have the following meanings:
XTT: 3,3'-Sodium [1-(carbaniloyl)-3,4-tetrazolium]-di(4-methoxy-6-nitro)benzene-sulfonate/2,3-Bis-(2-methoxy-4-nitro-5-sulfophenyl]-2H-tetrazolium-5-carboxyanilide salt, purchased from Amresco Ltd.;
RPMI1640: a medium designed by Roswell Park Memorial Institute; purchased from Hyclone Company;
FBS: fetal calf serum, purchased from Hyclone Company;
PBS: phosphate buffer, purchased from Homemade Company.
1. Formulating the Agents and the Compounds
1) Formulating PBS:
NaCl (8 g), KCl (0.2 g), Na$_2$HPO$_4$ (1.44 g), and KH$_2$PO$_4$ (0.24 g) were added to ultrapure water (800 mL). After adjusting the pH to 7.4, ultrapure water was further added until the volume reached 1 L. The mixture was autoclaved for 20 min.
2) Formulating the XTT Working Liquor:
XTT powder (100 mg) was taken and, while being kept in darkness, dissolved into 300 ml of the serum-free RPMI1640 culture medium that was warmed to 50° C. and did not contain phenol red. The mixture was filtered, packaged separately, and used immediately or within one week. It is necessary for all of the processes to be kept in darkness.
3) Formulating Test Compounds
Formulating a Stock Solution of Test Compound:
The compound powder was dissolved into DMSO until a concentration of 10 mM reached.
Formulating Gradient Dilute Solutions of Test Compound:
First, the 10 mM stock solution of test compound was diluted with DMSO in a 4-fold successive gradient for 10 concentrations. 2 μL DMSO-diluted compound was added to 998 μL of the culture medium containing 10% FBS. Therefore, the maximum concentration of the compound is 20 μM, the concentration of DMSO is 0.2%, and there are 10 concentration gradients in total.
2. Culturing Cells
1) Thawing Cells:
A cell-freezing tube was removed from liquid nitrogen, and placed in a water bath of 37° C.-39° C. to thaw the cells quickly.
A freezing-preserving solution was transferred to 15 ml sterile centrifuge tube, to which was added a culture medium in a volume 10 times larger than that of the freezing-preserving solution. The mixture was centrifuged at 1000 rpm at 4° C. for 5 min. The culture medium in the centrifuge tube was discarded, and then a culture medium containing 10% FBS was added. The cells were resuspended and transferred to the culture bottle. On the next day, the solution was changed.
2) Passing Cells
For the logarithmic growth phase cells, the culture medium was discarded and an appropriate volume of PBS was added to wash the cells once. Then an appropriate volume of a digestive juice containing 0.25% pancreatic enzyme and 0.02% EDTA was added. The solution was placed on stand at 37° C. for 2-5 min, and then washed once with PBS after the digestive juice was discarded. An appropriate volume of a culture medium containing 10% FBS was added to terminate the digestion. The pipette was blown and hit slightly, and the cells were digested down to produce a cell suspension for cell passage and further experiment.

3) Freezing and Preserving Cells

For the logarithmic growth phase cells, a digestive juice containing 0.25% pancreatic enzyme and 0.02% EDTA was used to digest cells to produce a cell suspension. The suspension was centrifuged at 1000 rpm at 4° C. for 5 min. The culture medium was discarded and a freezing-preserving solution containing 10% DMSO and 90% FBS was added to resuspend the cells. The cells were packaged separately in the cell-freezing tubes in $2 \times 10^6$ cells/tube. The cell-freezing tubes were placed in a programmed cooling cassette, kept at −80° C. for 24 hours, and then transferred to liquid nitrogen for freezing and preserving.

3. Plating Cells

1) Preparing the Cell Suspension

The culture medium was removed from the culture bottle. The cells were rinsed twice with PBS. The pancreatic enzyme was added to digest cells. The digested cells were collected by centrifuge. The cells were resuspended with a culture medium containing 10% fetal calf serum, counted and adjusted to an appropriate concentration (the cell viability should be over 90%). The cell concentration was $5 \times 10^4$/ml.

2) The cell suspension was added to the 96-well plate, 100 μL per well.

3) The plate was placed in the incubator and incubated at 37° C. under 5% $CO_2$ overnight.

4. Treating with Drugs

Drugs were added to the cell culture plate. The plate was placed in the incubator and incubated at 37° C. under 5% $CO_2$ for 72 hours.

5. Testing the Cell Viability with the XTT Method

The XTT working solution was added to the plate. The plate was placed in the incubator and incubated at 37° C. under 5% $CO_2$ for 2 hr. Then the plate was placed in a microplate reader to read the absorbance at 450 nm.

6. Data Processing

1) The percent inhibition was calculated by the following calculation.

% inhibitor=(Absorbance(medium)−Absorbance (Compound))/(Absorbance(medium)−Absorbance(positive control)×100%;

2) Data were input into GraphPad Prism 5.0 to plot a curve and obtain $IC_{50}$.

Result:

TABLE 2 in vitro cellular inhibitory activities on H1975 (NSCLC, nonsmall-cell lung cancer)
H1975 Cells

| Compound | $IC_{50}$ (nM) |
| --- | --- |
| erlotinib hydrochloride | 3985.0 |
| lapatinib ditosylate | 4534.0 |
| CI-1033 hydrochloride | 157.3 |

TABLE 2-continued in vitro cellular inhibitory activities on H1975 (NSCLC, nonsmall-cell lung cancer)
H1975 Cells

| Compound | $IC_{50}$ (nM) |
| --- | --- |
| Compound 8 | 305.6 |
| Compound 18 | 92.3 |
| Compound 19 hydrochloride | 104.5 |

TABLE 3 in vitro cellular inhibitory activities on Calu-3(NSCLC, nonsmall-cell lung cancer)
Calu-3 Cells

| Compound | $IC_{50}$ (nM) |
| --- | --- |
| erlotinib hydrochloride | 1319.0 |
| lapatinib ditosylate | 94.3 |
| CI-1033 hydrochloride | 685.6 |
| Compound 18 | 38.2 |

TABLE 4 in vitro cellular inhibitory activities on A431(Epidermoid carcinoma)
A431 cells

| Compounds | $IC_{50}$ (nM) |
| --- | --- |
| erlotinib hydrochloride | 1269.0 |
| lapatinib ditosylate | 3282.0 |
| CI-1033 hydrochloride | 402.4 |
| Compound 19 hydrochloride | 114.0 |

Note:
The cells H1975, Calu-3 and A431 used in the above assay were available from Chinese Vendor.

Conclusions:

It can be seen from Table 2 that the cellular proliferation inhibition effect of the present compounds on H1975 (NSCLC, nonsmall-cell lung cancer) is remarkably superior to erlotinib hydrochloride and lapatinib ditosylate.

It can be seen from Table 3 that the cellular proliferation inhibition effect of the present compounds on Calu-3 (NSCLC, nonsmall-cell lung cancer) is superior to lapatinib ditosylate, and remarkably superior to erlotinib hydrochloride and CI-1033 hydrochloride.

It can be seen from Table 4 that the cellular proliferation inhibition effect of the present compounds on A431 (Epidermoid carcinoma) is superior to CI-1033 hydrochloride, and remarkably superior to erlotinib hydrochloride and lapatinib ditosylate.

The invention claimed is:

1. A compound represented by a general formula (I), a pharmaceutically acceptable salt thereof or a stereoisomer thereof:

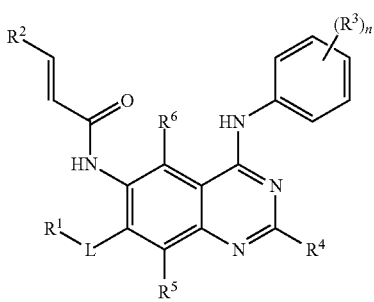

(I)

wherein

R¹ is selected from the group consisting of

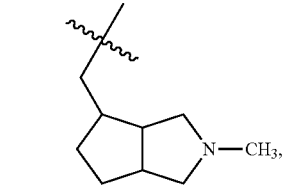

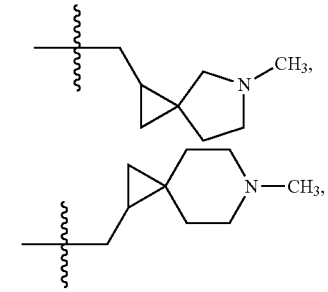

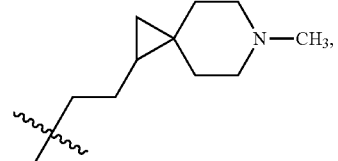

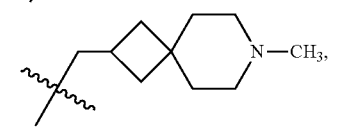

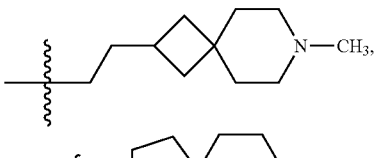

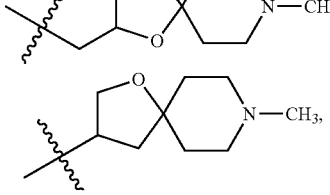

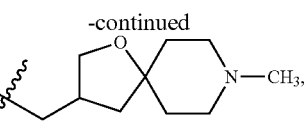

-continued

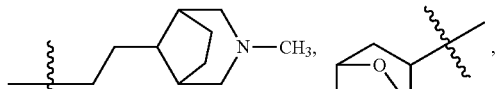

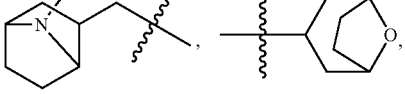

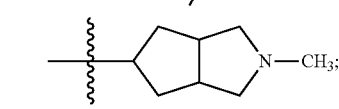

R² is selected from the group consisting of hydrogen and a $C_{1-4}$alkyl group that is unsubstituted or substituted by 1-2 $Q_2$ substituents, $Q_2$ is selected from the group consisting of a di($C_{1-4}$alkyl) amino group and a saturated 5-8 membered heterocyclyl group, R³ is selected from the group consisting of fluoro, chloro, and bromo;

R⁴, R⁵ and R⁶ are each hydrogen;

L is O;

n is 1, 2 or 3.

2. A compound according to claim 1, a pharmaceutically acceptable salt thereof or a stereoisomer thereof, wherein R¹ is selected from the group consisting of:

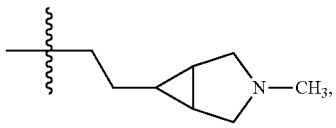

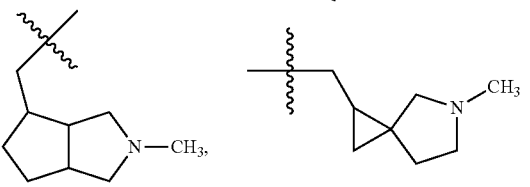

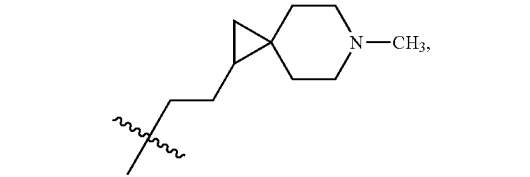

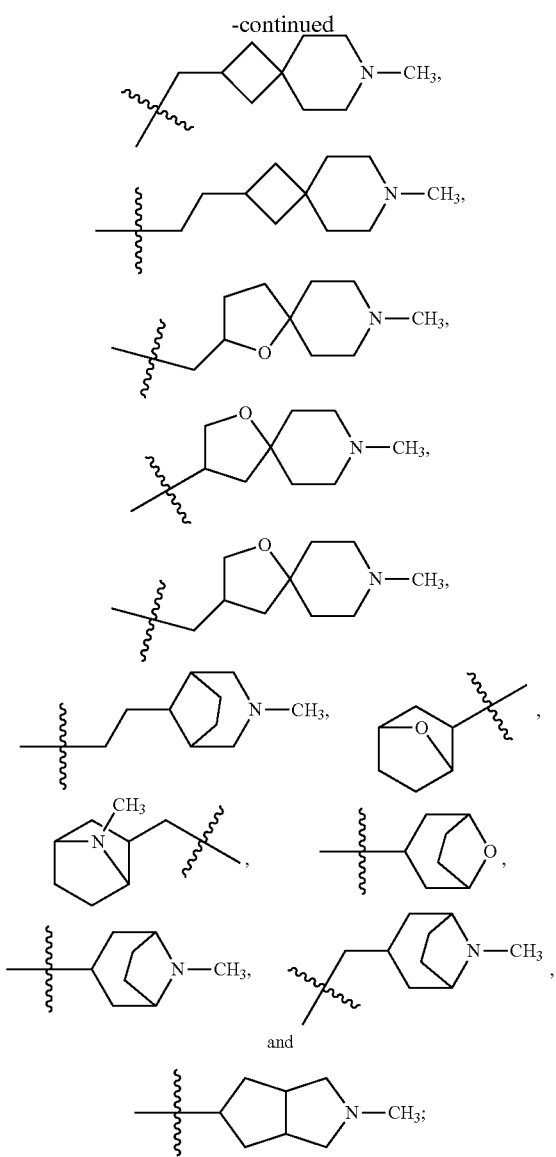

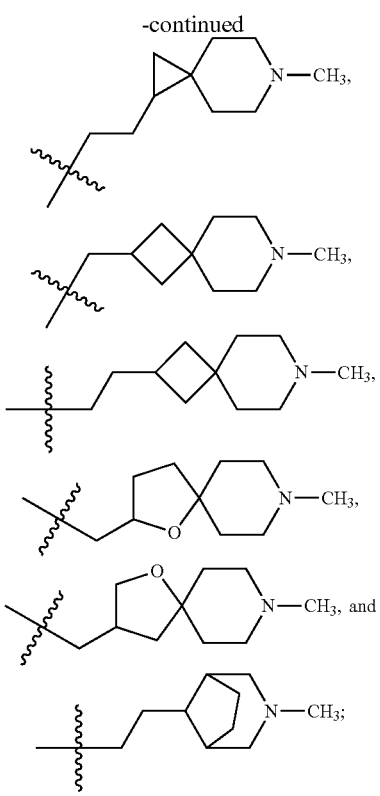

R² is selected from the group consisting of hydrogen, methyl that is unsubstituted or substituted by 1-2 Q₂ substituents, and ethyl that is unsubstituted or substituted by 1-2 Q₂ substituents, Q₂ is selected from the group consisting of:
(1) a di($C_{1-4}$alkyl)amino group,
(2) piperidinyl, piperazinyl, morpholinyl, and pyrrolidinyl;

R³ is selected from the group consisting of fluoro and chloro;

R⁴, R⁵ and R⁶ are hydrogen;

L is O; and n is 2.

3. A compound according to claim 1, a pharmaceutically acceptable salt thereof or a stereoisomer thereof, wherein R¹ is selected from the group consisting of:

R² is hydrogen;

R³ is selected from the group consisting of fluoro and chloro;

R⁴, R⁵ and R⁶ are hydrogen;

L is O; and n is 2.

4. A compound, a pharmaceutically acceptable salt thereof or a stereoisomer thereof, wherein the compound is selected from the group consisting of:

(E)-N-[7-(8-oxabicyclo[3.2.1]octan-3-yloxy)-4-(3-chloro-4-fluorophenylamino)quinazolin-6-yl]-4-(piperidin-1-yl)-2-butenamide, (E)-N-[7-(7-oxabicyclo[2.2.1]heptan-2-yloxy)-4-(3-chloro-4-fluorophenylamino)quinazolin-6-yl]-4-(piperidin-1-yl)-2-butenamide, N-[4-(3-chloro-4-fluorophenylamino)-7-(8-methyl-8-azabicyclo[3.2.1]octan-3-yloxy)quinazolin-6-yl]-acrylamide, N-[4-(3-chloro-4-fluorophenylamino)-7-(8-methyl-1-oxa-8-azaspiro[4.5]decan-3-yloxy)quinazolin-6-yl]-acrylamide, N-[4-(3-chloro-4-fluorophenylamino)-7-((8-methyl-1-oxa-8-azaspiro[4.5]decan-3-yl)methoxy)quinazolin-6-yl]-acrylamide, N-[4-(3-chloro-4-fluorophenylamino)-7-(8-methyl-1-oxa-8-azaspiro[4.5]decan-2-ylmethoxy)quinazolin-6-yl]-acrylamide, N-[4-(3-chloro-4-fluorophenylamino)-7-(2-(1R,5S,6S)-3-methyl-3-azabicyclo[3.1.0]hexan-6-ylethoxy)quinazolin-6-yl]-acrylamide, N-[4-(3-chloro-4-fluorophenylamino)-7-((2-methyloctahydrocyclopenta[c]pyrrol-4-yl)methoxy)quinazolin-6-yl]-acrylamide, N-[4-(3-chloro-4-fluorophenylamino)-7-((7-methyl-7-azabicyclo[2.2.1]heptan-2-yl)methoxy)quinazolin-6-yl]-acrylamide, N-[4-(3-chloro-4-fluorophenylamino)-7-(2-(3-methyl-3-azabicyclo[3.2.1]octan-8-yl)ethoxy)quinazolin-6-yl]-acrylamide,
N-[4-(3-chloro-4-fluorophenylamino)-7-((5-methyl-5-azaspiro[2.4]heptan-1-yl)methoxy)quinazolin-6-yl]-acrylamide,
N-[4-(3-chloro-4-fluorophenylamino)-7-((6-methyl-6-azaspiro[2.5]octan-1-yl)methoxy)quinazolin-6-yl]-acrylamide,
N-[4-(3-chloro-4-fluorophenylamino)-7-(2-(6-methyl-6-azaspiro[2.5]octan-1-yl)ethoxy)quinazolin-6-yl]-acrylamide,
(E)-N-[4-(3-chloro-4-fluorophenylamino)-7-((7-methyl-7-azaspiro[3.5]nonan-2-yl)methoxy)quinazolin-6-yl]-2-butenamide,
(E)-N-[4-(3-chloro-4-fluorophenylamino)-7-((7-methyl-7-azaspiro[3.5]nonan-2-yl)methoxy)quinazolin-6-yl]-2-pentenamide,
N-[4-(3-chloro-4-fluorophenylamino)-7-((7-methyl-7-azaspiro[3.5]nonan-2-yl)methoxy)quinazolin-6-yl]-acrylamide,
N-[4-(3-chloro-4-fluorophenylamino)-7-(2-(7-methyl-7-azaspiro[3.5]nonan-2-yl)ethoxy)quinazolin-6-yl]-acrylamide,
(E)-N-(4-(3-chloro-4-fluorophenylamino)-7-((7-methyl-7-azaspiro[3.5]nonan-2-yl)methoxy)quinazolin-6-yl)-4-dimethylamino-2-butenamide,
(E)-N-[4-(3-chloro-4-fluorophenylamino)-7-((2-(3-methyl-3-aza-bicyclo[3.1.0]-hexan-6-yl)-ethoxy)quinazolin-6-yl)]-4-dimethylamino-crotonamide,
(E)-N-[4-(3-chloro-4-fluorophenylamino)-7-(((spiro[3.5]nonan-2-yl)methoxy)quinazolin-6-yl)-4-dimethylamino]-crotonamide, and
(E)-N-(7-(bicyclo[3.1.0]hexan-6-ylmethoxy)-4-(3-chloro-4-fluorophenylamino)quinazolin-6-yl)-4-(dimethylamino)but-2-enamide.

5. A process for preparing a compound of general formula (I) according to claim 1, comprising the steps of:
Reaction Procedure:

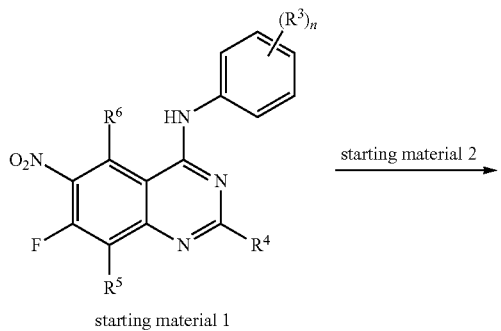

starting material 1

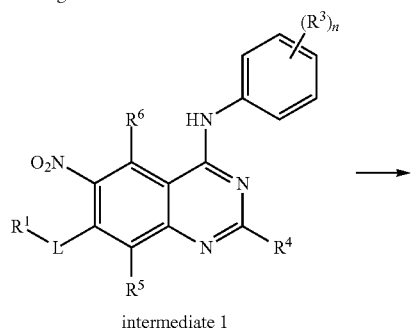

intermediate 1

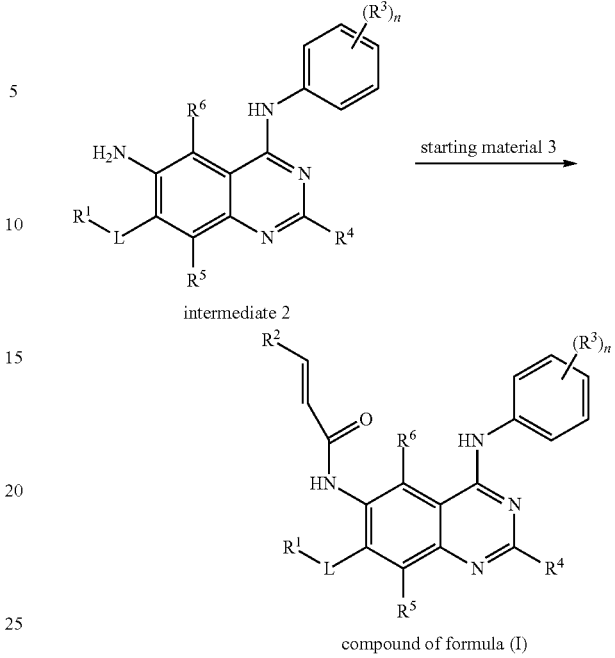

intermediate 2 compound of formula (I)

wherein, $R^1$, $R^2$, $R^3$, $R^4$, $R^5$, $R^6$, L and n are as defined in claim 1; the starting material 2=$R^1$-LH; the starting material 3=$R^2$CH=CH—C(O)Cl or $R^2$CH=CH—COOH, (1) Dissolving the starting material 2 in a non-protonic polar solvent, and reacting with the starting material 1 in the presence of a base to produce the Intermediate 1;
(2) Reacting the Intermediate 1 with a reducing agent optionally in the presence of an acid to produce the Intermediate 2; and
(3) Dissolving the Intermediate 2 in an organic solvent, and reacting with the starting material 3 in the presence of an organic base to produce the compound of formula (I).

6. A pharmaceutical composition, which contains a compound according to claim 1, a pharmaceutically acceptable salt thereof or a stereoisomer thereof.

7. A pharmaceutical composition according to claim 6, which further contains a second therapeutical agent selected from the group consisting of an antimetabolite, a growth factor inhibitor, an antibody, a mitotic inhibitor, an antineoplastic hormone, an alkylating agent, carboplatin, cisplatin, and oxaliplatin; a topoismerase inhibitor, and an immunosuppressant.

8. A pharmaceutical formulation containing a compound according to claim 1, a pharmaceutically acceptable salt thereof or a stereoisomer thereof and one or more pharmaceutically acceptable carriers, which formulation is in a form of any pharmaceutically acceptable dosage form.

9. The pharmaceutical composition according to claim 7, wherein the second therapeutical agent is selected from the group consisting of capecitabine, gemcitabine, pazopanib, imatinib, Herceptin, bevacizumab, paclitaxel, vinorelbine, docetaxel, doxorubicin, letrozole, tamoxifen, fulvestrant, cyclophosphamide, carmustine topotecan, and everolimus.

* * * * *